US007060789B1

(12) United States Patent
Braun et al.

(10) Patent No.: US 7,060,789 B1
(45) Date of Patent: Jun. 13, 2006

(54) RICIN-LIKE TOXINS FOR TREATMENT OF CANCER

(75) Inventors: Curtis Braun, Surrey (CA); Admir Purac, Burnaby (CA); Thor Borgford, Burnaby (CA)

(73) Assignee: Twinstrand Therapeutics Inc., British Columbia (CA)

( * ) Notice: Subject to any disclaimer, the term of this patent is extended or adjusted under 35 U.S.C. 154(b) by 421 days.

(21) Appl. No.: 10/089,058

(22) PCT Filed: Oct. 4, 2000

(86) PCT No.: PCT/CA00/01162

§ 371 (c)(1), (2), (4) Date: Sep. 19, 2002

(87) PCT Pub. No.: WO01/25267

PCT Pub. Date: Apr. 12, 2001

Related U.S. Application Data

(60) Provisional application No. 60/197,409, filed on Apr. 14, 2000, provisional application No. 60/157,807, filed on Oct. 4, 1999.

(51) Int. Cl.
*C07K 1/00* (2006.01)
*A61K 39/00* (2006.01)

(52) U.S. Cl. .................... 530/300; 530/350; 424/184.1

(58) Field of Classification Search ................ 530/300, 530/350; 424/184.1
See application file for complete search history.

(56) References Cited

U.S. PATENT DOCUMENTS

| | | | | |
|---|---|---|---|---|
| 4,869,903 | A | 9/1989 | Lifson et al. | |
| 5,101,025 | A | 3/1992 | Piatak, Jr. et al. | |
| 5,128,460 | A | 7/1992 | Piatak, Jr. et al. | |
| 5,820,866 | A * | 10/1998 | Kappler et al. | 424/192.1 |
| 6,333,303 | B1 * | 12/2001 | Borgford | 514/2 |
| 6,531,125 | B1 * | 3/2003 | Borgford | 424/94.3 |
| 6,803,358 | B1 * | 10/2004 | Borgford | 514/8 |

FOREIGN PATENT DOCUMENTS

| | | |
|---|---|---|
| EP | 466222 | 6/1985 |
| EP | 145111 | 1/1992 |
| WO | WO89/04839 | 6/1989 |
| WO | WO94/18332 | 8/1994 |
| WO | WO97/41233 | 11/1997 |
| WO | WO98/49311 | 11/1998 |

OTHER PUBLICATIONS

Abad-Zapatero, C. et al., *Protein Sci.* 5:640-652 (1996).
Allured, V.S. et al., *Proc. Natl. Acad. Sci. USA* 83:1320-1324 (1986).
Bever Jr., C.T., Panitch, H.S., and Johnson, K.P. (1994) Neurology 44(4), 745-8.
Blackman, M.J. et al. (*Mol. Biochem. Parasitol.* 62:103-114 1993.
Blaha, I. et al., *FEBS Lett.* 309:389-393 (1992).
Blum, J.S. et al., *J. Biol. Chem.* 266: 22091-22095 (1991).
Bonifacino, J.S., *Nature* 384: 405-406 (1996).
Carvalho, K. et al., *Biochem. Biophys. Res. Comm.* 191:172-179 (1993).
Chirgwin et al., *Biochemistry* 18, 5294-5299 (1979).
Cohen, P., Graves, H.C., Peehl, D.M., Kamarei, M., Guidice, L.C., and Rosenfeld, R.G. (1992) Journal of Clinal Endocrinology and Metabolism 75(4), 1046-53.
Collier, R.J. & Kandel, J., *J. Biol. Chem.* 246:1496-1503 (1971).
Collier, R.J. et al., *J. Biol. Chem.* 257:5283-5285 (1982).
Columblatti, M. et al., *J. Biol. Chem.* 261:3030-3035 (1986).
Conover, C.A. and De Leon, D.D., *J. Biol. Chem.* 269(10), 7076-80 (1994).
Cook, J.P. et al., *Bioconjugate Chem.* 4, 440-447 (1993).
Cooper, J.A. and Bujard, H. (*Mol. Biochem. Parasitol.* 56:151-160 (1992).
Cutfield, S.M. et al., *Biochemistry* 35:398-410 (1995).
Demeure, M.J. et al., *World J. Surg.* 16:770-776 (1992).
DiIannit, 1990, J. Biol. Chem. 285: 17345-17354 (1990).
Emmanuel, F. et al., Anal. *Biochem.* 173:134-141 (1988).
Endo, Y. & Tsurugi, K. J., *Biol. Chem.* 262:8128 (1987).
Fiani, M.L. et al., *Arch. Biochem. Biophys.* 307: 225-230 (1993).
Funmatsu et al., *Jap. J. Med. Sci. Biol.* 23:264-267 (1970).
Fusek, M. et al. (*FEBS Lett.* 327:108-112 (1993).
Garred, O. et al. (*J. Biol. Chem.* 270:10817-10821 (1995).
Gluzman, Y. (1975) Cell, 23, 175-182).
Goldberg, D.E. et al. (*J. Exp. Med.* 173:961-969 (1991).
Gray, G.L. et al., *Proc. Natl. Acad. Sci. USA* 81:2645-2649 (1984).
Greenfield, L. et al., *Proc. Natl. Acad. Sci. USA* 80:6853-6857 (1983).
Halling, K. et al. *Nucleic Acids Res.* 13:8019 (1985).
Hansen, G., Schuster, A., Zubrod, C., and Wahn, V. (1995) Respiration 62(3), 117-24.

*Primary Examiner*—Mark Navarro
(74) *Attorney, Agent, or Firm*—Micheline Gravelle Bereskin & Parr

(57) ABSTRACT

The present invention provides a protein having chain of a ricin-like toxin, a B chain of a ricin-like toxin and a novel heterologous linker amino acid sequence, linking the A and B chains. The linker sequence contains a cleavage recognition site for a specific protease such as those found in inflammatory cells and cancer cells. The invention also relates to a nucleic acid molecule encoding the protein and to expression vectors incorporating the nucleic acid molecule. Also provided is a method of inhibiting or destroying cells having a specific protease, such as cancer cells or inflammatory cells utilizing the nucleic acid molecules and proteins of the invention and pharmaceutical compositions for treating human inflammation and cancer.

11 Claims, 94 Drawing Sheets

OTHER PUBLICATIONS

Hirowatari, Y. et al., *Arch. Virol.* 133:349-356 (1993).
Hirowatari, Y. et al., *Anal.Biochem.* 225:113-120 (1995).
Holmberg, K. and Myer, R., *Scand. J. Infect. Dis.* 18:179-192 (1986).
Honn, K.V. et al. (*Biochem. Pharmacol.* 34:235-241 (1985).
Jewell, D.A. et al., *Biochemistry* 31:7862-7869 (1992).
Krane, S.M., *Ann: N.Y. Acad. Sci.* 732:1-10 (1994).
Lamb and Lord, *Eur. J. Biochem.* 14:265-270 (1985).
Leppla, S.H. et al. (Bacterial Protein Toxins zbl.bakt.suppl. 24:431-442 (1994).
Liu F. & Roizman, B: (*J. Virol.* 65:5149-5156 (1991).
Long, A.C. et al., *FEBS Lett.* 258:75-78 (1989).
Lord, J.M., *Eur. J. Biochem.* 146:411-416 (1985).
Lord, J.M., *Eur. J. Biochem.* 146:403-409 (1985).
Lord, J.M. et al., *FASAB Journal* 8:201-208 (1994).
Mackay, A.R. et al. *Lab. Invest.* 70:800-806 (1994).
May, M.J. et al. Embo. Journal, 8:301-308 at 302-303 (1989).
McKerrow, J.H. et al., *J. Biol. Chem.* 260:3703-3707 (1985).
McPherson, R.A. et al. (*Mol. Biochem. Parasitol.* 62:233-242 (1993).
Mikkelsen, T. et al. J. *Neurosurge*, 83:285-290 (1995).
Moore, D.H. et al. *Gynecol. Oncol.* 65:78-82 (1997).
Muller, H.L., Oh, Y., Gargosky, S.E., Lehrnbecher, T., Hintz, R.L., and Rosenfeld, R.G. (1993) Journal of Clinical Endocrinology and Metabolism 77(5), 1113-9.
Nakano et al. (1995) J. of Neurosurgery 83(2), 298-307.
Nwagwu, M. et al. (*Exp. Parasitol.* 75:399-414 (1992).
O'Dea, K.P. et al., *Mol. Biochem. Parasitol.* 72:111-119 (1995).
Ogata, M. et al., *J. Biol. Chem.* 267:25396-25401 (1992).
Olsnes, S. & Phil, A. in Molecular action of toxins and viruses (eds. Cohen, P. & vanHeyningen, S.) 51-105 Elsevier Biomedical Press, Amsterdam, 1982).
Olson et al., *AIDS Res. and Human Retroviruses* 7:1025-1030 (1991).
Panchal, R.G. et al., *Nature Biotechnology* 14:852-857 (1996).
Pastan et al., *Annals New York Academy of Sciences* 758:345-353 (1995).
Pastan, I. et al., *Annu. Rev. Biochem.* 61:331-354 (1992).
Peng, K-W, et al. *Human Gene Therapy*, 8:729-738 (1997).
Pettit, S.C. et al., *J. Biol. Chem.* 266:14539-14547 (1991).
Ray, T.L. and Payne, C.D. (*Infect. Immunol.* 58:508-514 (1990).
Remold, H.H. et al. (*Biochim. Biophys. Acta* 167:399-406 (1968).
Richardson, P.T. et al., *FEBS Lett.* 255:15-20 (1989).
Rosenthal, P.J. et al. (*J. Clin. Invest.* 91:1052-1056 (1993).
Ruchel, R. et al, *Zentralbl. Bakteriol. Mikrobiol Hyg. I Abt. Orig. A.* 255:537-548 (1983).
Rutenber, E. et al. *Proteins* 10:240-250 (1991).
Sandvig, K. et al., *Biochem. Soc. Trans.* 21:707-711 (1993).
Sandvig, K. & van Deurs, B., *FEBS Lett.* 346: 99-102 (1994).
Scarborough, P.E. et al., *Protein Sci.* 2:264-276 (1993).
Schreiber, B, et al., *Diagn. Microbiol. Infect. Dis.* 3:1-5 (1985).
Schwartz, M.K., *Clin. Chim. Acta* 237:67-78 (1995).
Shi, Y.E. et al., *Cancer Res.* 53:1409-1415 (1993).
Simmons et al., *Biol. Chem.* 261:7912 (1986).
Sloane, B.F. et al. (*Proc. Natl. Acad. Sci. USA* 83:2483-2487 (1986).
Spiess, E. et al., *J. Histochem. Cytochem.* 42:917-929 (1994).
Spooner et al., *Mol. Immunol.* 31:117-125, (1994).
Thompson, E.W. et al., *Breast Cancer Res. Treatment* 31:357-370 (1994).
Vasil, M.L. et al., *Infect. Immunol.* 16:353-361 (1977).
Vitetta et al., *Science* 238:1098-1104(1987).
Vitetta & Thorpe, *Seminars in Cell Biology* 2:47-58 (1991).
Vitetta et al., *Immunology Today* 14:252-259 (1993).
Weidner, J.R. et al. (*Arch. Biochem. Biophys.* 286:402-408 (1991).
Welch, A.R. et al. (*Arch. Biochem. Biophys.* 324:59-64 (1995).
Welch, A.R. (*Proc. Natl. Acad. Sci. USA* 88:10792-10796 (1991).
Wellner, R.B. et al. *J. Toxicol. Toxin Reviews*, 14(4), 483-522 (1995).
Westby et al., *Bioconjugate Chem.* 3:377-382 (1992).
Weston et al., *Mol. Biol.* 244:410-422 (1994).
Wiertz, E.J. et al., *Nature* 384: 432-438 (1996).
Woessner, J.F., *Ann. N.Y. Acad. Sci.* 732:11-21 (1994).
Young, T.N. et al. *Gynecol. Oncol.* 62:89-99 (1996).

* cited by examiner

FIGURE 1A

Sequence of pAP301 (MMP-9) Linker Region

WT preproricin linker

```
                                                         primer 301-3'
                                            5'- ATGTGGGGACAACGAAATTTTAATGCTGAT -3'
                                                  * *** ****  *
-CTCATGGTGTATAGATGCGCACCTCCACCATCGTCACAGTTTTCTTTGCTTATA|AGGCCAGTGGTACCAAATTTTAATGCTGATGTTTGTATGGATCCTGAGCCC-
-GAGTACCACATATCTACGCGTGGAGGTGGTAGCAGTGTCAAAAGAAACGAATAT|TCCGGTCACCATGGTTTAAAATTACGACTACAAACATACCTAGGACTCGGG-
                                     ** ***   ***
                 3'- GGTGGTAGCAGTGTCAAACCAGGAGAACCG -5'
                          primer 301-5'
```

1) PCR mutagenesis

2) Ligate with pVL1393 pAP301 linker
(MMP-9 variant)

```
GCACCTCCACCATCGTCACAGTTTGGTCCTCTTGGC|ATGTGGGGACAACGAAATTTTAATGCTGATGTT
CGTGGAGGTGGTAGCAGTGTCAAACCAGGAGAACCG|TACACCCCTGTTGCTTTAAAATTACGACTACAA
```

Note: Nucleotides in bold are found within the preproricin linker region. The '-' symbol within the linker designate deleted nucleotides.

FIGURE 1B (P1)

Sequence of pAP301 insert

```
                10         20         30         40         50
                 |          |          |          |          |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGAAATACCAGTGTTGCCAA
    AGCAAATTGTTGACCTCGACTACACTCTGTACTTTATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 1B (P2)

```
701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGCACCTCCACCA
     ATAATTAGGGATAGTATCGAGAGTACCACATATCTACGCGTGGAGGTGGT

901  TCGTCACAGTTTGGTCCTCTTGGCATGTGGGGACAACGAAATTTTAATGC
     AGCAGTGTCAAACCAGGAGAACCGTACACCCCTGTTGCTTTAAAATTACG

951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 1B (P3)

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGGTTGGTGTTAGAT
     AGTTCTTACTACCTTGGTAAAATTTAAACATATCACCCAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1855.

Sequence name: pAP301

Note: Nucleotides in bold are found within the mutant preproricin linker region. The '-' symbol within the linker region designate deleted nucleotides.

FIGURE 1C

Amino acid sequence Comparison of Mutant Preproricin Linker Region of PAP301 (MMP-9) to Wild Type

```
Wild type ricin linker:     A chain- C A P P P S S Q F S L L I R P V V P N F N A D V C M D P E -B chain

PAP301 (MMP-9) linker:      A chain- C A P P P S S Q F G P L G M W G Q R N F N A D V C M D P E -B chain
```

Note: Amino acids in bold are found within the preproricin linker region. The '-' symbol within the linker designate deleted amino acids.

FIGURE 2A

Sequence of pAP302 (MMP-9) Linker Region

WT preproricin linker

```
                                                               primer 302-3'
                                                     5'- GGGCAG--------------------TGTATGGATCCTGAGCCC -3'
                                                           * ***
-CTCATGGTGTATAGATGCGCACCTCCACCATCGTCACAGTTTTCTTTGCTTATAAGGCCA|GTGGTACCAAATTTTAATGCTGATGTTTGTATGGATCCTGAGCCC-
-GAGTACCACATATCTACGCGTGGAGGTGGTAGCAGTGTCAAAAGAAACGAATATTCCGGT|CACCATGGTTTAAAATTACGACTACAAACATACCTAGGACTCGGG-
                                            **   ****   ***
                             3'- AGCAGTGTCAAAAGAGGCGTTCCTTAACGT -5'
                                         primer 302-5'
```

1) PCR mutagenesis

2) Ligate with pVL1393 pAP302 linker
(MMP-9 variant)

```
GCACCTCCACCATCGTCACAGTTTTCTCCGCAAGGAATTGCA|GGGCAG
CGTGGAGGTGGTAGCAGTGTCAAAAGAGGCGTTCCTTAACGT|CCCGTC
```

Note: Nucleotides in bold are found within the preproricin linker region. The '-' symbol within the linker designate deleted nucleotides.

FIGURE 2B (P1)

Sequence of pAP302 insert

```
        10        20        30        40        50
         |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGAAATACCAGTGTTGCCAA
    AGCAAATTGTTGACCTCGACTACACTCTGTACTTTATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 2B (P2)

```
701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGCACCTCCACCA
     ATAATTAGGGATAGTATCGAGAGTACCACATATCTACGCGTGGAGGTGGT

901  TCGTCACAGTTTTCTCCGCAAGGAATTGCAGGGCAG--------------
     AGCAGTGTCAAAAGAGGCGTTCCTTAACGTCCCGTC--------------

951  -------TGTATGGATCCTGAGCCCATAGTGCGTATCGTAGGTCGAAATG
     -------ACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 2B (P3)

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGGTTGGTGTTAGAT
     AGTTCTTACTACCTTGGTAAAATTTAAACATATCACCCAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1834.

Sequence name: pAP302

Note: Nucleotides in bold are found within the mutant preproricin linker region. The '-' symbol within the linker region designate deleted nucleotides.

FIGURE 2C

Amino acid sequence Comparison of Mutant Preproricin Linker Region of PAP302 (MMP-9) to Wild Type

| | | |
|---|---|---|
| Wild type ricin linker: | A chain- | C A P P P S S Q F S L L I R P V V P N F N A D V C M D P E -B chain |
| PAP302 (MMP-9) linker: | A chain- | C A P P P S S Q F S P Q G I A G Q - - - - - - - - C M D P E -B chain |

Note: Amino acids in bold are found within the preproricin linker region. The '-' symbol within the linker designate deleted amino acids.

FIGURE 3A

Sequence of pAP303 (MMP-9) Linker Region

WT preproricin linker

```
                                                                          primer 303-3'
                                                              5'- GGGCAGCGAAATTTTAATGCTGAT -3'
                                                                   * *** *
    -CTCATGGTGTATAGATGCGCACCTCCACCATCGTCACAGTTTTCTTTGCTTATAAGGCCA|GTGGTACCAAATTTTAATGCTGATGTTTGTATGGATCCTGAGCCC-
    -GAGTACCACATATCTACGCGTGGAGGTGGTAGCAGTGTCAAAAGAAACGAATATTCCGGT|CACCATGGTTTAAAATTACGACTACAAACATACCTAGGACTCGGG-
                                                **   ****   ***
3'  -GAGTACCACATATCTACG------------------------AGAGGCGTTCCTTAACGT -5'
                             primer 303-5'
```

1) PCR mutagenesis

2) Ligate with pVL1393 pAP303 linker
(MMP-9 variant)

```
TCTCCGCAAGGAATTGCA|GGGCAGCGAAATTTTAATGCTGATGTT
AGAGGCGTTCCTTAACGT|CCCGTCGCTTTAAAATTACGACTACAA
```

Note: Nucleotides in bold are found within the preproricin linker region. The '-' symbol within the linker designate deleted nucleotides.

FIGURE 3B (P1)

Sequence of pAP303 insert

```
              10         20         30         40         50
              |          |          |          |          |
  1  GAATTCATGAAACCGGGAGGAAATACTATTGTAATATGGATGTATGCAGT
     CTTAAGTACTTTGGCCCTCCTTTATGATAACATTATACCTACATACGTCA

 51  GGCAACATGGCTTTGTTTTGGATCCACCTCAGGGTGGTCTTTCACATTAG
     CCGTTGTACCGAAACAAAACCTAGGTGGAGTCCCACCAGAAAGTGTAATC

101  AGGATAACAACATATTCCCCAAACAATACCCAATTATAAACTTTACCACA
     TCCTATTGTTGTATAAGGGGTTTGTTATGGGTTAATATTTGAAATGGTGT

151  GCGGGTGCCACTGTGCAAAGCTACACAAACTTTATCAGAGCTGTTCGCGG
     CGCCCACGGTGACACGTTTCGATGTGTTTGAAATAGTCTCGACAAGCGCC

201  TCGTTTAACAACTGGAGCTGATGTGAGACATGAAATACCAGTGTTGCCAA
     AGCAAATTGTTGACCTCGACTACACTCTGTACTTTATGGTCACAACGGTT

251  ACAGAGTTGGTTTGCCTATAAACCAACGGTTTATTTTAGTTGAACTCTCA
     TGTCTCAACCAAACGGATATTTGGTTGCCAAATAAAATCAACTTGAGAGT

301  AATCATGCAGAGCTTTCTGTTACATTAGCGCTGGATGTCACCAATGCATA
     TTAGTACGTCTCGAAAGACAATGTAATCGCGACCTACAGTGGTTACGTAT

351  TGTGGTCGGCTACCGTGCTGGAAATAGCGCATATTTCTTTCATCCTGACA
     ACACCAGCCGATGGCACGACCTTTATCGCGTATAAAGAAAGTAGGACTGT

401  ATCAGGAAGATGCAGAAGCAATCACTCATCTTTTCACTGATGTTCAAAAT
     TAGTCCTTCTACGTCTTCGTTAGTGAGTAGAAAAGTGACTACAAGTTTTA

451  CGATATACATTCGCCTTTGGTGGTAATTATGATAGACTTGAACAACTTGC
     GCTATATGTAAGCGGAAACCACCATTAATACTATCTGAACTTGTTGAACG

501  TGGTAATCTGAGAGAAAATATCGAGTTGGGAAATGGTCCACTAGAGGAGG
     ACCATTAGACTCTCTTTTATAGCTCAACCCTTTACCAGGTGATCTCCTCC

551  CTATCTCAGCGCTTTATTATTACAGTACTGGTGGCACTCAGCTTCCAACT
     GATAGAGTCGCGAAATAATAATGTCATGACCACCGTGAGTCGAAGGTTGA

601  CTGGCTCGTTCCTTTATAATTTGCATCCAAATGATTTCAGAAGCAGCAAG
     GACCGAGCAAGGAAATATTAAACGTAGGTTTACTAAAGTCTTCGTCGTTC

651  ATTCCAATATATTGAGGGAGAAATGCGCACGAGAATTAGGTACAACCGGA
     TAAGGTTATATAACTCCCTCTTTACGCGTGCTCTTAATCCATGTTGGCCT
```

FIGURE 3B (P2)

701 GATCTGCACCAGATCCTAGCGTAATTACACTTGAGAATAGTTGGGGGAGA
CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
AGTTGACGTTTCTGCATTACCAAGGTTTAAGTCACACATGCTACACTCAT

851 TATTAATCCCTATCATAGCTCTCATGGTGTATAGATGC------------
ATAATTAGGGATAGTATCGAGAGTACCACATATCTACG------------

901 ------------TCTCCGCAAGGAATTGCAGGGCAGCGAAATTTTAATGC
------------AGAGGCGTTCCTTAACGTCCCGTCGCTTTAAAATTACG

951 TGATGTTTGTATGGATCCTGAGCCCATAGTGCGTATCGTAGGTCGAAATG
ACTACAAACATACCTAGGACTCGGGTATCACGCATAGCATCCAGCTTTAC

1001 GTCTATGTGTTGATGTTAGGGATGGAAGATTCCACAACGGAAACGCAATA
CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
GTCAACACCGGTACGTTCAGATTATGTCTACGTTTAGTCGAGACCTGAAA

1101 GAAAAGAGACAATACTATTCGATCTAATGGAAAGTGTTTAACTACTTACG
CTTTTCTCTGTTATGATAAGCTAGATTACCTTTCACAAATTGATGAATGC

1151 GGTACAGTCCGGGAGTCTATGTGATGATCTATGATTGCAATACTGCTGCA
CCATGTCAGGCCCTCAGATACACTACTAGATACTAACGTTATGACGACGT

1201 ACTGATGCCACCCGCTGGCAAATATGGGATAATGGAACCATCATAAATCC
TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
AATGTCACGTTTGGTTGTAAATACGGCAATCAGTTCCAACCGAAGGATGA

1351 AATAATACACAACCTTTTGTTACAACCATTGTTGGGCTATATGGTCTGTG
TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
GAACGTTCGTTTATCACCTGTTCATACCTATCTCCTGACATCGTCACTTT

FIGURE 3B (P3)

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGGTTGGTGTTAGAT
     AGTTCTTACTACCTTGGTAAAATTTAAACATATCACCCAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1831.

Sequence name: pAP303

Note: Nucleotides in bold are found within the mutant preproricin linker region. The '-' symbol within the linker region designate deleted nucleotides.

FIGURE 3C

Amino acid sequence Comparison of Mutant Preproricin Linker Region of PAP303 (MMP-9) to Wild Type

```
Wild type ricin linker:      A chain- C A P P P S S Q F S L L I R P V V P N F N A D V C M D P E -B chain

PAP303 (MMP-9) linker:       A chain- C - - - - - - - - S P Q G I A G Q R N F N A D V C M D P E -B chain
```

Note: Amino acids in bold are found within the preproricin linker region. The '-' symbol within the linker designate deleted amino acids.

FIGURE 4A

Sequence of pAP304 (MMP-9) Linker Region

WT preproricin linker

```
                                                                            primer 304-3'
                                                                5'- GGGCAG---------------------TGTATGGATCCTGAGCCC -3'
                                                                      * ***
   -CTCATGGTGTATAGATGCGCACCTCCACCATCGTCACAGTTTTCTTTGCTTATAAGGCCA|GTGGTACCAAATTTTAATGCTGATGTTTGTATGGATCCTGAGCCC-
   -GAGTACCACATATCTACGCGTGGAGGTGGTAGCAGTGTCAAAAGAAACGAATATTCCGGT|CACCATGGTTTAAAATTACGACTACAAACATACCTAGGACTCGGG-
                                                 **  ****  ***
3' -GAGTACCACATATCTACG------------------------AGAGGCGTTCCTTAACGT -5'
                         primer 304-5'
```

1) PCR mutagenesis

2) Ligate with pVL1393 pAP304 linker
(MMP-9 variant)

```
TCTCCGCAAGGAATTGCA|GGGCAG
AGAGGCGTTCCTTAACGT|CCCGTC
```

Note: Nucleotides in bold are found within the preproricin linker region. The '-' symbol within the linker designate deleted nucleotides.

FIGURE 4B (P1)

Sequence of pAP304 insert

```
          10        20        30        40        50
           |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGAAATACCAGTGTTGCCAA
    AGCAAATTGTTGACCTCGACTACACTCTGTACTTTATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 4B (P2)

```
701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGC------------
     ATAATTAGGGATAGTATCGAGAGTACCACATATCTACG------------

901  ------------TCTCCGCAAGGAATTGCAGGGCAG--------------
     ------------AGAGGCGTTCCTTAACGTCCCGTC--------------

951  -------TGTATGGATCCTGAGCCCATAGTGCGTATCGTAGGTCGAAATG
     -------ACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 4B (P3)

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGGTTGGTGTTAGAT
     AGTTCTTACTACCTTGGTAAAATTTAAACATATCACCCAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1810.

Sequence name: pAP304

Note: Nucleotides in bold are found within the mutant preproricin linker region. The '-' symbol within the linker region designate deleted nucleotides.

FIGURE 4C

Amino acid sequence Comparison of Mutant Preproricin Linker Region of PAP304 (MMP-9) to Wild Type

| | |
|---|---|
| Wild type ricin linker: | A chain- C **A P P P S S Q F S L L I R P V V P N F N A** D V C M D P E -B chain |
| PAP304 (MMP-9) linker: | A chain- C - - - - - - - - **S P Q G I A G Q** - - - - - - - C M D P E -B chain |

Note: Amino acids in bold are found within the preproricin linker region. The '-' symbol within the linker designate deleted amino acids.

FIGURE 5A

Sequence of pAP305 (MMP-9) Linker Region

WT preproricin linker

```
                                                                      primer 305-3'
                                                    5'- GGGCAG----------------------TGTATGGATCCTGAGCCC -3'
                                                         * ***
-CTCATGGTGTATAGATGCGCACCTCCACCATCGTCACAGTTTTCTTTGCTTATAAGGCCA|GTGGTACCAAATTTTAATGCTGATGTTTGTATGGATCCTGAGCCC-
-GAGTACCACATATCTACGCGTGGAGGTGGTAGCAGTGTCAAAAGAAACGAATATTCCGGT|CACCATGGTTTAAAATTACGACTACAAACATACCTAGGACTCGGG-
                                             **  ****  ***
      3'- TCTACGCGTGGAGGTGGT------------AGAGGCGTTCCTTAACGT -5'
                            primer 305-5'
```

1) PCR mutagenesis

2) Ligate with pVL1393 pAP 305 linker
(MMP-9 variant)

```
GCACCTCCACCATCTCCGCAAGGAATTGCA|GGGCAG
CGTGGAGGTGGTAGAGGCGTTCCTTAACGT|CCCGTC
```

Note: Nucleotides in bold are found within the preproricin linker region. The '-' symbol within the linker designate deleted nucleotides.

FIGURE 5B (P1)

Sequence of pAP305 insert

```
          10         20         30         40         50
           |          |          |          |          |
  1  GAATTCATGAAACCGGGAGGAAATACTATTGTAATATGGATGTATGCAGT
     CTTAAGTACTTTGGCCCTCCTTTATGATAACATTATACCTACATACGTCA

 51  GGCAACATGGCTTTGTTTTGGATCCACCTCAGGGTGGTCTTTCACATTAG
     CCGTTGTACCGAAACAAAACCTAGGTGGAGTCCCACCAGAAAGTGTAATC

101  AGGATAACAACATATTCCCCAAACAATACCCAATTATAAACTTTACCACA
     TCCTATTGTTGTATAAGGGGTTTGTTATGGGTTAATATTTGAAATGGTGT

151  GCGGGTGCCACTGTGCAAAGCTACACAAACTTTATCAGAGCTGTTCGCGG
     CGCCCACGGTGACACGTTTCGATGTGTTTGAAATAGTCTCGACAAGCGCC

201  TCGTTTAACAACTGGAGCTGATGTGAGACATGAAATACCAGTGTTGCCAA
     AGCAAATTGTTGACCTCGACTACACTCTGTACTTTATGGTCACAACGGTT

251  ACAGAGTTGGTTTGCCTATAAACCAACGGTTTATTTTAGTTGAACTCTCA
     TGTCTCAACCAAACGGATATTTGGTTGCCAAATAAAATCAACTTGAGAGT

301  AATCATGCAGAGCTTTCTGTTACATTAGCGCTGGATGTCACCAATGCATA
     TTAGTACGTCTCGAAAGACAATGTAATCGCGACCTACAGTGGTTACGTAT

351  TGTGGTCGGCTACCGTGCTGGAAATAGCGCATATTTCTTTCATCCTGACA
     ACACCAGCCGATGGCACGACCTTTATCGCGTATAAAGAAAGTAGGACTGT

401  ATCAGGAAGATGCAGAAGCAATCACTCATCTTTTCACTGATGTTCAAAAT
     TAGTCCTTCTACGTCTTCGTTAGTGAGTAGAAAAGTGACTACAAGTTTTA

451  CGATATACATTCGCCTTTGGTGGTAATTATGATAGACTTGAACAACTTGC
     GCTATATGTAAGCGGAAACCACCATTAATACTATCTGAACTTGTTGAACG

501  TGGTAATCTGAGAGAAAATATCGAGTTGGGAAATGGTCCACTAGAGGAGG
     ACCATTAGACTCTCTTTTATAGCTCAACCCTTTACCAGGTGATCTCCTCC

551  CTATCTCAGCGCTTTATTATTACAGTACTGGTGGCACTCAGCTTCCAACT
     GATAGAGTCGCGAAATAATAATGTCATGACCACCGTGAGTCGAAGGTTGA

601  CTGGCTCGTTCCTTTATAATTTGCATCCAAATGATTTCAGAAGCAGCAAG
     GACCGAGCAAGGAAATATTAAACGTAGGTTTACTAAAGTCTTCGTCGTTC

651  ATTCCAATATATTGAGGGAGAAATGCGCACGAGAATTAGGTACAACCGGA
     TAAGGTTATATAACTCCCTCTTTACGCGTGCTCTTAATCCATGTTGGCCT
```

FIGURE 5B (P2)

```
701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGCACCTCCACCA
     ATAATTAGGGATAGTATCGAGAGTACCACATATCTACGCGTGGAGGTGGT

901  ------------TCTCCGCAAGGAATTGCAGGGCAG--------------
     ------------AGAGGCGTTCCTTAACGTCCCGTC--------------

951  -------TGTATGGATCCTGAGCCCATAGTGCGTATCGTAGGTCGAAATG
     -------ACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 5B (P3)

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGGTTGGTGTTAGAT
     AGTTCTTACTACCTTGGTAAAATTTAAACATATCACCCAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1822.

Sequence name: pAP305

Note: Nucleotides in bold are found within the mutant preproricin linker region. The '-' symbol within the linker region designate deleted nucleotides.

FIGURE 5C

Amino acid sequence Comparison of Mutant Preproricin Linker Region of PAP305 (MMP-9) to Wild Type

| | |
|---|---|
| Wild type ricin linker: | A chain- C **A P P P S S Q F S L L I R P V V P N F N A D V** C M D P E -B chain |
| PAP305 (MMP-9) linker: | A chain- C **A P P P - - - - S P Q G I A G Q - - - - - - - -** C M D P E -B chain |

Note: Amino acids in bold are found within the preproricin linker region. The '-' symbol within the linker designate deleted amino acids.

FIGURE 6A

Sequence of pAP308 (MMP-9) Linker Region

WT preproricin linker

```
                                                                                primer 308-3'
                                                       5'- ATGTGGGACAA----------------------TGTGGTGGCGGAGGGCCCATAGTGCGTATCGTA -3
                                                             * *** ****                      *** ***** *
-CTCATGGTGTATAGATGCGCACCTCCACCATCGTCACAGTTTTCTTTGCTTATA|AGGCCAGTGGTACCAAATTTTAATGCTGATGTTTGTATGGATCCTGAGCCCATAGTGCGTATCGTA-
-GAGTACCACATATCTACGCGTGGAGGTGGTAGCAGTGTCAAAAGAAACGAATAT|TCCGGTCACCATGGTTTAAAATTACGACTACAAACATACCTAGGACTCGGGTATCACGCATAGCAT-
                                              ** ***   ***
         3'- TCTACGCGTGGAGGTGGT------------CCAGGAGAACCG -5'
                                   primer 308-5'
```

1) PCR mutagenesis

2) Ligate with pVL1393 pAP 308 linker
(MMP-9 variant)

```
GCACCTCCACCAGGTCCTCTTGGC|ATGTGGGGACAA
CGTGGAGGTGGTCCAGGAGAACCG|TACACCCCTGTT
```

Note: Nucleotides in bold are found within the preproricin linker region. The '-' symbol within the linker designate deleted nucleotides.

FIGURE 6B (P1)

Sequence of pAP308 insert

```
                10         20         30         40         50
                 |          |          |          |          |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGAAATACCAGTGTTGCCAA
    AGCAAATTGTTGACCTCGACTACACTCTGTACTTTATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 6B (P2)

701 GATCTGCACCAGATCCTAGCGTAATTACACTTGAGAATAGTTGGGGGAGA
CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
AGTTGACGTTTCTGCATTACCAAGGTTTAAGTCACACATGCTACACTCAT

851 TATTAATCCCTATCATAGCTCTCATGGTGTATAGATGCGCACCTCCACCA
ATAATTAGGGATAGTATCGAGAGTACCACATATCTACGCGTGGAGGTGGT

901 ------------GGTCCTCTTGGCATGTGGGGACAA--------------
------------CCAGGAGAACCGTACACCCCTGTT--------------

951 -------TGTGGTGGCGGAGGGCCCATAGTGCGTATCGTAGGTCGAAATG
-------ACACCACCGCCTCCCGGGTATCACGCATAGCATCCAGCTTTAC

1001 GTCTATGTGTTGATGTTAGGGATGGAAGATTCCACAACGGAAACGCAATA
CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
GTCAACACCGGTACGTTCAGATTATGTCTACGTTTAGTCGAGACCTGAAA

1101 GAAAAGAGACAATACTATTCGATCTAATGGAAAGTGTTTAACTACTTACG
CTTTTCTCTGTTATGATAAGCTAGATTACCTTTCACAAATTGATGAATGC

1151 GGTACAGTCCGGGAGTCTATGTGATGATCTATGATTGCAATACTGCTGCA
CCATGTCAGGCCCTCAGATACACTACTAGATACTAACGTTATGACGACGT

1201 ACTGATGCCACCCGCTGGCAAATATGGGATAATGGAACCATCATAAATCC
TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
AATGTCACGTTTGGTTGTAAATACGGCAATCAGTTCCAACCGAAGGATGA

1351 AATAATACACAACCTTTTGTTACAACCATTGTTGGGCTATATGGTCTGTG
TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
GAACGTTCGTTTATCACCTGTTCATACCTATCTCCTGACATCGTCACTTT

FIGURE 6B (P3)

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGGTTGGTGTTAGAT
     AGTTCTTACTACCTTGGTAAAATTTAAACATATCACCCAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1822.

Sequence name: pAP308

Note: Nucleotides in bold are found within the mutant preproricin linker region. The '-' symbol within the linker region designate deleted nucleotides.

FIGURE 6C

Amino acid sequence Comparison of Mutant Preproricin Linker Region of PAP308 (MMP-9) to Wild Type

Wild type ricin linker: A chain- C A P P P S S Q F S L L I R P V V P N F N A D V C M D P E -B chain PAP308 (MMP-9) linker: A chain- C A P P P - - - - G P L G M W G Q - - - - - - - C G G G G -B chain

Note: Amino acids in bold are found within the preproricin linker region. The '-' symbol within the linker designate deleted amino acids.

FIGURE 7A

Sequence of pAP309 (MMP-9) Linker Region

WT preproricin linker

```
                                                                          primer 309-3'
                                                        5'- TTTAATGCTGATGTTTGTGGTGGCGGAGGGCCCATAGTGCGTATCGTA -3
                                                                          *** ***** *
TGGTGTATAGATGCGCACCTCCACCATCGTCACAGTTTTCTTTGCTTATAAGGCCAGTGGTACCAAAT|TTTAATGCTGATGTTTGTATGGATCCTGAGCCCATAGTGCGTATCGTA-
ACCACATATCTACGCGTGGAGGTGGTAGCAGTGTCAAAAGAAACGAATATTCCGGTCACCATGGTTTA|AAATTACGACTACAAACATACCTAGGACTCGGGTATCACGCATAGCAT-
                                  ** ***   *** **********  *
                 3'- GGTGGTAGCAGTGTCAAACCAGGAGAACCGTACACCCCTGTTGCTTTA -5'
                                  primer 309-5'
```

1) PCR mutagenesis

2) Ligate with pVL1393 pAP309 linker
(MMP-9 variant)

```
GCACCTCCACCATCGTCACAGTTTGGTCCTCTTGGCATGTGGGGACAACGAAAT|TTTAATGCTGATGTT
CGTGGAGGTGGTAGCAGTGTCAAACCAGGAGAACCGTACACCCCTGTTGCTTTA|AAATTACGACTACAA
```

Note: Nucleotides in bold are found within the preproricin linker region. The '-' symbol within the linker designate deleted amino acids.

FIGURE 7B (P1)

Sequence of pAP309 insert

```
           10        20        30        40        50
            |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGAAATACCAGTGTTGCCAA
    AGCAAATTGTTGACCTCGACTACACTCTGTACTTTATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 7B (P2)

701 GATCTGCACCAGATCCTAGCGTAATTACACTTGAGAATAGTTGGGGGAGA
CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
AGTTGACGTTTCTGCATTACCAAGGTTTAAGTCACACATGCTACACTCAT

851 TATTAATCCCTATCATAGCTCTCATGGTGTATAGATGCGCACCTCCACCA
ATAATTAGGGATAGTATCGAGAGTACCACATATCTACGCGTGGAGGTGGT

901 TCGTCACAGTTTGGTCCTCTTGGCATGTGGGGACAACGAAATTTTAATGC
AGCAGTGTCAAACCAGGAGAACCGTACACCCCTGTTGCTTTAAAATTACG

951 TGATGTTTGTGGTGGCGGAGGGCCCATAGTGCGTATCGTAGGTCGAAATG
ACTACAAACACCACCGCCTCCCGGGTATCACGCATAGCATCCAGCTTTAC

1001 GTCTATGTGTTGATGTTAGGGATGGAAGATTCCACAACGGAAACGCAATA
CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
GTCAACACCGGTACGTTCAGATTATGTCTACGTTTAGTCGAGACCTGAAA

1101 GAAAAGAGACAATACTATTCGATCTAATGGAAAGTGTTTAACTACTTACG
CTTTTCTCTGTTATGATAAGCTAGATTACCTTTCACAAATTGATGAATGC

1151 GGTACAGTCCGGGAGTCTATGTGATGATCTATGATTGCAATACTGCTGCA
CCATGTCAGGCCCTCAGATACACTACTAGATACTAACGTTATGACGACGT

1201 ACTGATGCCACCCGCTGGCAAATATGGGATAATGGAACCATCATAAATCC
TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
AATGTCACGTTTGGTTGTAAATACGGCAATCAGTTCCAACCGAAGGATGA

1351 AATAATACACAACCTTTTGTTACAACCATTGTTGGGCTATATGGTCTGTG
TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
GAACGTTCGTTTATCACCTGTTCATACCTATCTCCTGACATCGTCACTTT

FIGURE 7B (P3)

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGGTTGGTGTTAGAT
     AGTTCTTACTACCTTGGTAAAATTTAAACATATCACCCAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1855.

Sequence name: pAP309

Note: Nucleotides in bold are found within the mutant preproricin linker region. The '-' symbol within the linker region designate deleted nucleotides.

FIGURE 7C

Amino acid sequence Comparison of Mutant Preproricin Linker Region of PAP309 (MMP-9) to Wild Type

| | |
|---|---|
| Wild type ricin linker: | A chain- C A P P P S S Q F S L L I R P V V P N F N A D V C M D P E -B chain |
| PAP-309 (MMP-9) linker: | A chain- C A P P P S S Q F G P L G M W G Q R N F N A D V C G G G G -B chain |

Note: Amino acids in bold are found within the preproricin linker region. The '-' symbol within the linker designate deleted amino acids.

FIGURE 8A

Sequence of pAP313 (UPA) Linker Region

WT preproricin linker

```
                                                                                     primer 313-3'
                                                5'- GTAGTCGGCGGG------------------------TGTATGGATCCTGAG -3'
                                                     *  ****** *
-CTCATGGTGTATAGATGCGCACCTCCACCATCGTCACAGTTTTCTTTGCTT|ATAAGGCCAGTGGTACCAAATTTTAATGCTGATGTTTGTATGGATCCTGAGCCC-
-GAGTACCACATATCTACGCGTGGAGGTGGTAGCAGTGTCAAAAGAAACGAA|TATTCCGGTCACCATGGTTTAAAATTACGACTACAAACATACCTAGGACTCGGG-
                                          * **** **
3' -TACCACATATCTACG------------------------GGTCCTGCT -5'
                   primer 313-5'
```

1) PCR mutagenesis

2) Ligate with pVL1393 pAP313 linker
(UPA variant)

```
CCAGGACGA|GTAGTCGGCGGG
GGTCCTGCT|CATCAGCCGCCC
```

Note: Nucleotides in bold are found within the preproricin linker region. The '-' symbol within the linker designate deleted nucleotides.

FIGURE 8B (P1)

Sequence of pAP313 insert

```
          10        20        30        40        50
           |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGAAATACCAGTGTTGCCAA
    AGCAAATTGTTGACCTCGACTACACTCTGTACTTTATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 8B (P2)

```
701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGC------------
     ATAATTAGGGATAGTATCGAGAGTACCACATATCTACG------------

901  ------------CCAGGACGAGTAGTCGGCGGG-----------------
     ------------GGTCCTGCTCATCAGCCGCCC-----------------

951  -------TGTATGGATCCTGAGCCCATAGTGCGTATCGTAGGTCGAAATG
     -------ACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 8B (P3)

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGGTTGGTGTTAGAT
     AGTTCTTACTACCTTGGTAAAATTTAAACATATCACCCAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1807.

Sequence name: pAP313

Note: Nucleotides in bold are found within the mutant preproricin linker region. The '-' symbol within the linker region designate deleted nucleotides.

FIGURE 8C

Amino acid sequence Comparison of Mutant Preproricin Linker Region of PAP313 (UPA) to Wild Type

| | |
|---|---|
| Wild type ricin linker: | A chain- C A P P P S S Q F S L L I R P V V P N F N A D V C M D P E -B chain |
| PAP313 (UPA) linker: | A chain- C - - - - - - - - - P G R V V G G - - - - - - - - C M D P E -B chain |

Note: Amino acids in bold are found within the preproricin linker region. The '-' symbol within the linker designate deleted amino acids.

FIGURE 9A

Sequence of pAP314 (UPA) Linker Region

WT preproricin linker

```
                                                                        primer 314-3'
                                                  5'- GTAGTCGGCGGG------------GGAGGCGGGGGTTGTATGGATCCTGAG -3'
                                                      *  ****** *             *** ** ** *
-CTCATGGTGTATAGATGCGCACCTCCACCATCGTCACAGTTTTCTTTGCTT|ATAAGGCCAGTGGTACCAAATTTTAATGCTGATGTTTGTATGGATCCTGAGCCC-
-GAGTACCACATATCTACGCGTGGAGGTGGTAGCAGTGTCAAAAGAAACGAA|TATTCCGGTCACCATGGTTTAAAATTACGACTACAAACATACCTAGGACTCGGG-
                  * *********             * **** **
3' -TACCACATATCTACGCCTCCGCCCCCA------------GGTCCTGCT -5'
                        primer 314-5'
```

1) PCR mutagenesis

2) Ligate with pVL1393 pAP314 linker
(UPA variant)

```
GGAGGCGGGGGTCCAGGACGA|GTAGTCGGCGGGGGAGGCGGGGGT
CCTCCGCCCCCAGGTCCTGCT|CATCAGCCGCCCCCTCCGCCCCCA
```

Note: Nucleotides in bold are found within the preproricin linker region. The '-'symbol within the linker designate deleted nucleotides.

FIGURE 9B (P1)

Sequence of pAP314 insert

```
          10        20        30        40        50
           |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGAAATACCAGTGTTGCCAA
    AGCAAATTGTTGACCTCGACTACACTCTGTACTTTATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 9B (P2)

701 GATCTGCACCAGATCCTAGCGTAATTACACTTGAGAATAGTTGGGGGAGA
CTAGACGTGGTCTAGGATCGCATTAATGTGAACTCTTATCAACCCCCTCT

751 CTTTCCACTGCAATTCAAGAGTCTAACCAAGGAGCCTTTGCTAGTCCAAT
GAAAGGTGACGTTAAGTTCTCAGATTGGTTCCTCGGAAACGATCAGGTTA

801 TCAACTGCAAAGACGTAATGGTTCCAAATTCAGTGTGTACGATGTGAGTA
AGTTGACGTTTCTGCATTACCAAGGTTTAAGTCACACATGCTACACTCAT

851 TATTAATCCCTATCATAGCTCTCATGGTGTATAGATGCGGAGGCGGGGGT
ATAATTAGGGATAGTATCGAGAGTACCACATATCTACGCCTCCGCCCCCA

901 ------------CCAGGACGAGTAGTCGGCGGG------------GGAGG
------------GGTCCTGCTCATCAGCCGCCC------------CCTCC

951 CGGGGGTTGTATGGATCCTGAGCCCATAGTGCGTATCGTAGGTCGAAATG
GCCCCCAACATACCTAGGACTCGGGTATCACGCATAGCATCCAGCTTTAC

1001 GTCTATGTGTTGATGTTAGGGATGGAAGATTCCACAACGGAAACGCAATA
CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
GTCAACACCGGTACGTTCAGATTATGTCTACGTTTAGTCGAGACCTGAAA

1101 GAAAAGAGACAATACTATTCGATCTAATGGAAAGTGTTTAACTACTTACG
CTTTTCTCTGTTATGATAAGCTAGATTACCTTTCACAAATTGATGAATGC

1151 GGTACAGTCCGGGAGTCTATGTGATGATCTATGATTGCAATACTGCTGCA
CCATGTCAGGCCCTCAGATACACTACTAGATACTAACGTTATGACGACGT

1201 ACTGATGCCACCCGCTGGCAAATATGGGATAATGGAACCATCATAAATCC
TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
AATGTCACGTTTGGTTGTAAATACGGCAATCAGTTCCAACCGAAGGATGA

1351 AATAATACACAACCTTTTGTTACAACCATTGTTGGGCTATATGGTCTGTG
TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
GAACGTTCGTTTATCACCTGTTCATACCTATCTCCTGACATCGTCACTTT

FIGURE 9B (P3)

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGGTTGGTGTTAGAT
     AGTTCTTACTACCTTGGTAAAATTTAAACATATCACCCAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1831.

Sequence name: pAP314

Note: Nucleotides in bold are found within the mutant preproricin linker region. The '-' symbol within the linker region designate deleted nucleotides.

FIGURE 9C

Amino acid sequence Comparison of Mutant Preproricin Linker Region of PAP314 (UPA) to Wild Type

| | |
|---|---|
| Wild type ricin linker: | A chain- C A P P P S S Q F S L L I R P V V P N F N A D V C M D P E -B chain |
| PAP314 (UPA) linker: | A chain- C G G G G - - - - P G R V V G G - - - - G G G G C M D P E -B chain |

Note: Amino acids in bold are found within the preproricin linker region. The '-' symbol within the linker designate deleted amino acids.

FIGURE 10A

Sequence of pAP315 (UPA) Linker Region

WT preproricin linker

```
                                                              primer 315-3'
                                          5'- CCAGGACGAGTAGTCGGCGGG---------------TGTATGGATCCTGAG -3'
                                              ** * * *   *  *******
-CTCATGGTGTATAGATGCGCACCTCCACCATCGTCACAGTTTTCTTTGCTT|ATAAGGCCAGTGGTACCAAATTTTAATGCTGATGTTTGTATGGATCCTGAGCCC-
-GAGTACCACATATCTACGCGTGGAGGTGGTAGCAGTGTCAAAAGAAACGAA|TATTCCGGTCACCATGGTTTAAAATTACGACTACAAACATACCTAGGACTCGGG-
                              * ***  *** **********
3' -TACCACATATCTACG------------GGTCCTGCTCATCAGCCGCCC -5'
                     primer 315-5'
```

1) PCR mutagenesis

2) Ligate with pVL1393 pAP315 linker
(UPA variant)

```
CCAGGACGAGTAGTCGGCGGG|CCAGGACGAGTAGTCGGCGGG
GGTCCTGCTCATCAGCCGCCC|GGTCCTGCTCATCAGCCGCCC
```

Note: Nucleotides in bold are found within the preproricin linker region. The '-' symbol within the linker designate deleted nucleotides.

FIGURE 10B (P1)

Sequence of pAP315 insert

```
                10        20        30        40        50
                 |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGAAATACCAGTGTTGCCAA
    AGCAAATTGTTGACCTCGACTACACTCTGTACTTTATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 10B (P2)

```
701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGC------------
     ATAATTAGGGATAGTATCGAGAGTACCACATATCTACG------------

901  CCAGGACGAGTAGTCGGCGGGCCAGGACGAGTAGTCGGCGGG--------
     GGTCCTGCTCATCAGCCGCCCGGTCCTGCTCATCAGCCGCCC--------

951  -------TGTATGGATCCTGAGCCCATAGTGCGTATCGTAGGTCGAAATG
     -------ACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 10B (P3)

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGGTTGGTGTTAGAT
     AGTTCTTACTACCTTGGTAAAATTTAAACATATCACCCAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1828.

Sequence name: pAP315

Note: Nucleotides in bold are found within the mutant preproricin linker region. The '-' symbol within the linker region designate deleted nucleotides.

FIGURE 10C

Amino acid sequence Comparison of Mutant Preproricin Linker Region of PAP315 (UPA) to Wild Type

| | |
|---|---|
| Wild type ricin linker: | A chain- C A P P P S S Q F S L L I R P V V P N F N A D V C M D P E -B chain |
| PAP315 (UPA) linker: | A chain- C - - - - P G R V V G G P G R V V G G - - - - - C M D P E -B chain |

Note: Amino acids in bold are found within the preproricin linker region. The '-' symbol within the linker designate deleted amino acids.

FIGURE 11A

Sequence of pAP316 (MMP-9) Linker Region

WT preproricin linker

```
                                                      primer 316-3'
                                       5'- ATTGCAGGGCAGGGAGGGGGTAGTAGCGGCGGGGGATGTATGGATCCTGAG -3'
                                            *********   * *****  **    *    **  **  **
-CTCATGGTGTATAGATGCGCACCTCCACCATCGTCACAGTTTTCTTTGCTT|ATAAGGCCAGTGGTACCAAATTTTAATGCTGATGTTTGTATGGATCCTGAGCCC-
-GAGTACCACATATCTACGCGTGGAGGTGGTAGCAGTGTCAAAAGAAACGAA|TATTCCGGTCACCATGGTTTAAAATTACGACTACAAACATACCTAGGACTCGGG-
                  * ***************** **  *  *******
              3' -TACCACATATCTACGCCTCCGCCCTGAGGTCCGCCCCCAGGCGTTCCT -5'
```

1) PCR mutagenesis

2) Ligate with pVL1393 pAP316 linker
(MMP-9 variant)

```
GGAGGCGGGGACTCCAGCGGGGGTCCGCAAGGA|ATTGCAGGGCAGGGAGGGGGTAGTAGCGGCGGGGGA
CCTCCGCCCCTGAGGTCGCCCCCAGGCGTTCCT|TAACGTCCCGTCCCTCCCCCATCATCGCCGCCCCCT
```

Note: Nucleotides in bold are found within the preproricin linker region. The '-' symbol within the linker designate deleted nucleotides.

FIGURE 11B (P1)

Sequence of pAP316 insert

```
           10         20         30         40         50
            |          |          |          |          |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGAAATACCAGTGTTGCCAA
    AGCAAATTGTTGACCTCGACTACACTCTGTACTTTATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 11B (P2)

```
 701 GATCTGCACCAGATCCTAGCGTAATTACACTTGAGAATAGTTGGGGGAGA
     CTAGACGTGGTCTAGGATCGCATTAATGTGAACTCTTATCAACCCCCTCT

 751 CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

 801 TCAACTGCAAAGACGTAATGGTTCCAAATTCAGTGTGTACGATGTGAGTA
     AGTTGACGTTTCTGCATTACCAAGGTTTAAGTCACACATGCTACACTCAT

 851 TATTAATCCCTATCATAGCTCTCATGGTGTATAGATGCGGAGGCGGGGGT
     ATAATTAGGGATAGTATCGAGAGTACCACATATCTACGCCTCCGCCCTGA

 901 GGAGGCGGGGGTCCGCAAGGAATTGCAGGGCAGGGAGGGGGTAGTAGCGG
     GGTCCGCCCCCAGGCGTTCCTTAACGTCCCGTCCCTCCCCATCATCGCC

 951 CGGGGGATGTATGGATCCTGAGCCCATAGTGCGTATCGTAGGTCGAAATG
     GCCCCCTACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 11B (P3)

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGGTTGGTGTTAGAT
     AGTTCTTACTACCTTGGTAAAATTTAAACATATCACCCAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1855.

Sequence name: pAP316

Note: Nucleotides in bold are found within the mutant preproricin linker region. The '-' symbol within the linker region designate deleted nucleotides.

FIGURE 11C

Amino acid sequence Comparison of Mutant Preproricin Linker Region of PAP316 (MMP-9) to Wild Type

| | |
|---|---|
| Wild type ricin linker: | A chain- C **A P P P S S Q F S L L I R P V V P N F N A D V** C M D P E -B chain |
| PAP316 (MMP-9) linker: | A chain- C **G G G S S G G G P Q G I A G Q G G G S S G G G** C M D P E -B chain |

Note: Amino acids in bold are found within the preproricin linker region. The '-' symbol within the linker designate deleted amino acids.

FIGURE 12A

Sequence of pAP318 (MMP-9) Linker Region

WT preproricin linker

```
                                                          primer 318-3'
                                            5'- ATTGCAGGGCAGGATGAAGAGGATGCTGATGTTTGTATG -3'
                                                ****    * ******* ******
-CTCATGGTGTATAGATGCGCACCTCCACCATCGTCACAGTTTTCTTTGCTTATA|AGGCCAGTGGTACCAAATTTTAATGCTGATGTTTGTATGGATCCTGAGCCC-
-GAGTACCACATATCTACGCGTGGAGGTGGTAGCAGTGTCAAAAGAAACGAATAT|TCCGGTCACCATGGTTTAAAATTACGACTACAAACATACCTAGGACTCGGG-
                                   *****    **  ****
                 3'- GGAGGTGGTAGCAGTCCTCCAAGAGGCGTTCCT -5'
                     primer 318-5'
```

1) PCR mutagenesis

2) Ligate with pVL1393 pAP318 linker
(MMP-9 variant)

```
GCACCTCCACCATCGTCAGGAGGTTCTCCGCAAGGA|ATTGCAGGGCAGGATGAAGAGGATGCTGATGTT
CGTGGAGGTGGTAGCAGTCCTCCAAGAGGCGTTCCT|TAACGTCCCGTCCTACTTCTCCTACGACTACAA
```

Note: Nucleotides in bold are found within the preproricin linker region. The '-' symbol within the linker designate deleted nucleotides.

FIGURE 12B (P1)

Sequence of pAP318 insert

```
           10        20        30        40        50
            |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGAAATACCAGTGTTGCCAA
    AGCAAATTGTTGACCTCGACTACACTCTGTACTTTATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 12B (P2)

```
701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGCACCTCCACCA
     ATAATTAGGGATAGTATCGAGAGTACCACATATCTACGCGTGGAGGTGGT

901  TCGTCGGAGGTTCTCCGCAAGGAATTGCAGGGCAGGATGAAGAGGAATGC
     AGCAGCCTCCAAGAGGCGTTCCTTAACGTCCCGTCCTACTTCTCCTTACG

951  TGATGTTTGTATGGATCCTGAGCCCATAGTGCGTATCGTAGGTCGAAATG
     ACTACAAACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 12B (P3)

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGGTTGGTGTTAGAT
     AGTTCTTACTACCTTGGTAAAATTTAAACATATCACCCAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1855.

Sequence name: pAP318

Note: Nucleotides in bold are found within the mutant preproricin linker region. The '-' symbol within the linker region designate deleted nucleotides.

FIGURE 12C

Amino acid sequence Comparison of Mutant Preproricin Linker Region of PAP318 (MMP-9) to Wild Type

```
Wild type ricin linker:    A chain- C A P P P S S Q F S L L I R P V V P N F N A D V C M D P E -B chain
PAP318 (MMP-9) linker:     A chain- C A P P P S S G G S P Q G I A G Q D E E D A D V C M D P E -B chain
```

Note: Amino acids in bold are found within the preproricin linker region. The '-' symbol within the linker designate deleted amino acids.

FIGURE 13A

Sequence of pAP320 (UPA) Linker Region

WT preproricin linker

```
                                                              primer 320-3'
                                            5'- GTAGTCGGCGGG---------------GGGGGAGGCTGTATGGATCCTGAG -3'
                                                *  ****** *                 ** ** **
-CTCATGGTGTATAGATGCGCACCTCCACCATCGTCACAGTTTTCTTTGCTT|ATAAGGCCAGTGGTACCAAATTTTAATGCTGATGTTTGTATGGATCCTGAGCCC-
-GAGTACCACATATCTACGCGTGGAGGTGGTAGCAGTGTCAAAAGAAACGAA|TATTCCGGTCACCATGGTTTAAAATTACGACTACAAACATACCTAGGACTCGGG-
                     * *****               * **** **
3' -TACCACATATCTACGCCTCCGCCT---------------GGTCCTGCT -5'
                     primer 320-5'
```

1) PCR mutagenesis

2) Ligate with pVL1393 pAP320 linker
(UPA variant)

```
GGAGGCGGACCAGGACGA|GTAGTCGGCGGGGGGGAGGC
CCTCCGCCTGGTCCTGCT|CATCAGCCGCCCCCCCTCCG
```

Note: Nucleotides in bold are found within the preproricin linker region. The '-' symbol within the linker designate deleted nucleotides.

FIGURE 13B (P1)

Sequence of pAP320 insert

```
              10        20        30        40        50
               |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGAAATACCAGTGTTGCCAA
    AGCAAATTGTTGACCTCGACTACACTCTGTACTTTATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 13B (P2)

```
701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGGAGGCGGA---
     ATAATTAGGGATAGTATCGAGAGTACCACATATCTACGCCTCCGCCT---

901  ------------CCAGGACGAGTAGTCGGCGGG---------------GG
     ------------GGTCCTGCTCATCAGCCGCCC---------------CC

951  GGGAGGCTGTATGGATCCTGAGCCCATAGTGCGTATCGTAGGTCGAAATG
     CCCTCCGACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 13B (P3)

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGGTTGGTGTTAGAT
     AGTTCTTACTACCTTGGTAAAATTTAAACATATCACCCAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1825.

Sequence name: pAP320

Note: Nucleotides in bold are found within the mutant preproricin linker region. The '-' symbol within the linker region designate deleted nucleotides.

FIGURE 13C

Amino acid sequence Comparison of Mutant Preproricin Linker Region of PAP320 (UPA) to Wild Type

| | |
|---|---|
| Wild type ricin linker: | A chain- C A P P P S S Q F S L L I R P V V P N F N A D V C M D P E -B chain |
| PAP320 (UPA) linker: | A chain- C G G G - - - - - P G R V V G G - - - - - G G G C M D P E -B chain |

Note: Amino acids in bold are found within the preproricin linker region. The '-' symbol within the linker designate deleted amino acids.

FIGURE 14A

Sequence of pAP321 (UPA) Linker Region

WT preproricin linker

```
                                                        primer 321-3'
                                       5'- GTAGTCGGCGGG-----------------GGAGGCTGTATGGATCCTGAG -3'
                                           *  ****** *                    ** **
-CTCATGGTGTATAGATGCGCACCTCCACCATCGTCACAGTTTTCTTTGCTT|ATAAGGCCAGTGGTACCAAATTTTAATGCTGATGTTTGTATGGATCCTGAGCCC-
-GAGTACCACATATCTACGCGTGGAGGTGGTAGCAGTGTCAAAAGAAACGAA|TATTCCGGTCACCATGGTTTAAAATTACGACTACAAACATACCTAGGACTCGGG-
                  * ***                  * **** **
3' -TACCACATATCTACGCCTCCG-----------------GGTCCTGCT -5'
                   primer 321-5'
```

1) PCR mutagenesis

2) Ligate with pVL1393 pAP321 linker
(UPA variant)

```
GGAGGCCCAGGACGA|GTAGTCGGCGGGGGAGGC
CCTCCGGGTCCTGCT|CATCAGCCGCCCCCTCCG
```

Note: Nucleotides in bold are found within the preproricin linker region. The '-' symbol within the linker designate deleted nucleotides.

FIGURE 14B (P1)

Sequence of pAP321 insert

```
             10        20        30        40        50
              |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGAAATACCAGTGTTGCCAA
    AGCAAATTGTTGACCTCGACTACACTCTGTACTTTATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 14B (P2)

```
701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGGAGGC------
     ATAATTAGGGATAGTATCGAGAGTACCACATATCTACGCCTCCG------

901  ------------CCAGGACGAGTAGTCGGCGGG-----------------
     ------------GGTCCTGCTCATCAGCCGCCC-----------------

951  -GGAGGCTGTATGGATCCTGAGCCCATAGTGCGTATCGTAGGTCGAAATG
     -CCTCCGACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 14B (P3)

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGGTTGGTGTTAGAT
     AGTTCTTACTACCTTGGTAAAATTTAAACATATCACCCAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1819.

Sequence name: pAP321

Note: Nucleotides in bold are found within the mutant preproricin linker region. The '-' symbol within the linker region designate deleted nucleotides.

FIGURE 14C

Amino acid sequence Comparison of Mutant Preproricin Linker Region of PAP321 (UPA) to Wild Type

| | |
|---|---|
| Wild type ricin linker: | A chain- C **A P P P S S Q F S L L I R P V V P N F N A D V** C M D P E -B chain |
| PAP321 (UPA) linker: | A chain- C **G G** - - - - - - - **P G R V V G G** - - - - - - - **G G** C M D P E -B chain |

Note: Amino acids in bold are found within the preproricin linker region. The '-' symbol within the linker designate deleted amino acids.

FIGURE 15A

Sequence of pAP322 (UPA) Linker Region

WT preproricin linker

```
                                                                          primer 322-3'
                                                   5'- GTAGTCGGCGGG--------------------GGCTGTATGGATCCTGAG -3'
                                                       *  ****** *                      **
-CTCATGGTGTATAGATGCGCACCTCCACCATCGTCACAGTTTTCTTTGCTT|ATAAGGCCAGTGGTACCAAATTTTAATGCTGATGTTTGTATGGATCCTGAGCCC-
-GAGTACCACATATCTACGCGTGGAGGTGGTAGCAGTGTCAAAAGAAACGAA|TATTCCGGTCACCATGGTTTAAAATTACGACTACAAACATACCTAGGACTCGGG-
                  *                    * **** **
3' -TACCACATATCTACGCCT--------------------GGTCCTGCT -5'
                     primer 322-5'
```

1) PCR mutagenesis

2) Ligate with pVL1393 pAP322 linker
(UPA variant)

```
GGACCAGGACGA|GTAGTCGGCGGGGGC
CCTGGTCCTGCT|CATCAGCCGCCCCCG
```

Note: Nucleotides in bold are found within the preproricin linker region. The '-' symbol within the linker designate deleted nucleotides.

FIGURE 15B (P1)

Sequence of pAP322 insert

```
         10         20         30         40         50
          |          |          |          |          |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGAAATACCAGTGTTGCCAA
    AGCAAATTGTTGACCTCGACTACACTCTGTACTTTATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 15B (P2)

```
701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGGA---------
     ATAATTAGGGATAGTATCGAGAGTACCACATATCTACGCCT---------

901  ------------CCAGGACGAGTAGTCGGCGGG-----------------
     ------------GGTCCTGCTCATCAGCCGCCC-----------------

951  ----GGCTGTATGGATCCTGAGCCCATAGTGCGTATCGTAGGTCGAAATG
     ----CCGACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 15B (P3)

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGGTTGGTGTTAGAT
     AGTTCTTACTACCTTGGTAAAATTTAAACATATCACCCAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1813.

Sequence name: pAP322

Note: Nucleotides in bold are found within the mutant preproricin linker region. The '-' symbol within the linker region designate deleted nucleotides.

FIGURE 15C

Amino acid sequence Comparison of Mutant Preproricin Linker Region of PAP322 (UPA) to Wild Type

```
Wild type ricin linker:    A chain- C A P P P S S Q F S L L I R P V V P N F N A D V C M D P E -B chain

PAP322 (UPA) linker:       A chain- C G - - - - - - - P G R V V G G - - - - - - - G C M D P E -B chain
```

Note: Amino acids in bold are found within the preproricin linker region. The '-' symbol within the linker designate deleted amino acids.

FIGURE 16A

Sequence of pAP323 (MMP-9) Linker Region

WT preproricin linker

```
                                                         primer 323-3'
                                      5'- ATTGCAGGGCAG---GGGGTAGTAGCGGCGGGGGATGTATGGATCCTGAG -3'
                                            *********     ***** **   ** ** ** **
-CTCATGGTGTATAGATGCGCACCTCCACCATCGTCACAGTTTTCTTTGCTT|ATAAGGCCAGTGGTACCAAATTTTAATGCTGATGTTTGTATGGATCCTGAGCCC-
-GAGTACCACATATCTACGCGTGGAGGTGGTAGCAGTGTCAAAAGAAACGAA|TATTCCGGTCACCATGGTTTAAAATTACGACTACAAACATACCTAGGACTCGGG-
                   * ******* ** *    ** ** * *******
3' -TACCACATATCTACGCCTCCGCCCTGAGGT---CCCCCAGGCGTTCCT -5'
                     primer 323-5'
```

1) PCR mutagenesis

2) Ligate with pVL1393 pAP323 linker
(MMP-9 variant)

```
GGAGGCGGGACTCCAGGGGGTCCGCAAGGA|ATTGCAGGGCAGGGGGGTAGTAGCGGCGGGGGA
CCTCCGCCCTGAGGTCCCCCAGGCGTTCCT|TAACGTCCCGTCCCCCCATCATCGCCGCCCCCT
```

Note: Nucleotides in bold are found within the preproricin linker region. The '-' symbol within the linker designate deleted nucleotides.

FIGURE 16B (P1)

Sequence of pAP323 insert

```
           10        20        30        40        50
            |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGAAATACCAGTGTTGCCAA
    AGCAAATTGTTGACCTCGACTACACTCTGTACTTTATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 16B (P2)

```
701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGGAGGCGGGACT
     ATAATTAGGGATAGTATCGAGAGTACCACATATCTACGCCTCCGCCCTGA

901  CCAGGG---GGTCCGCAAGGAATTGCAGGGCAG---GGGGGTAGTAGCGG
     GGTCCC---CCAGGCGTTCCTTAACGTCCCGTC---CCCCCATCATCGCC

951  CGGGGGATGTATGGATCCTGAGCCCATAGTGCGTATCGTAGGTCGAAATG
     GCCCCCTACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 16B (P3)

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGGTTGGTGTTAGAT
     AGTTCTTACTACCTTGGTAAAATTTAAACATATCACCCAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1849.

Sequence name: pAP323

Note: Nucleotides in bold are found within the mutant preproricin linker region. The '-' symbol within the linker region designate deleted nucleotides.

FIGURE 16C

Amino acid sequence Comparison of Mutant Preproricin Linker Region of PAP323 (MMP-9) to Wild Type

```
Wild type ricin linker:    A chain- C A P P P S S Q F S L L I R P V V P N F N A D V C M D P E -B chain
PAP323 (MMP-9) linker:     A chain- C G G G S S - G G P Q G I A G Q - G G S S G G G C M D P E -B chain
```

Note: Amino acids in bold are found within the preproricin linker region. The '-' symbol within the linker designate deleted amino acids.

FIGURE 17A

Sequence of pAP324 (MMP-9) Linker Region

WT preproricin linker

```
                                                       primer 324-3'
                                          5'- ATTGCAGGGCAG------GGTAGTAGCGGCGGGGATGTATGGATCCTGAG -3'
                                               *********        ** **  ** ** ** **
-CTCATGGTGTATAGATGCGCACCTCCACCATCGTCACAGTTTTCTTTGCTT|ATAAGGCCAGTGGTACCAAATTTTAATGCTGATGTTTGTATGGATCCTGAGCCC-
-GAGTACCACATATCTACGCGTGGAGGTGGTAGCAGTGTCAAAAGAAACGAA|TATTCCGGTCACCATGGTTTAAAATTACGACTACAAACATACCTAGGACTCGGG-
                    * ******* ** *      ** * *******
3' -TACCACATATCTACGCCTCCGCCCTGAGGT------CCAGGCGTTCCT -5'
                      primer 324-5'
```

1) PCR mutagenesis

2) Ligate with pVL1393

AP324 linker
(MMP-9 variant)

```
GGAGGCGGGACTCCAGGTCCGCAAGGA|ATTGCAGGGCAGGGTAGTAGCGGCGGGGA
CCTCCGCCCTGAGGTCCAGGCGTTCCT|TAACGTCCCGTCCCATCATCGCCGCCCCT
```

Note: Nucleotides in bold are found within the preproricin linker region. The '-' symbol within the linker designate deleted nucleotides.

FIGURE 17B (P1)

Sequence of pAP324 insert

```
           10        20        30        40        50
            |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGAAATACCAGTGTTGCCAA
    AGCAAATTGTTGACCTCGACTACACTCTGTACTTTATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 17B (P2)

```
 701 GATCTGCACCAGATCCTAGCGTAATTACACTTGAGAATAGTTGGGGGAGA
     CTAGACGTGGTCTAGGATCGCATTAATGTGAACTCTTATCAACCCCCTCT

 751 CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

 801 TCAACTGCAAAGACGTAATGGTTCCAAATTCAGTGTGTACGATGTGAGTA
     AGTTGACGTTTCTGCATTACCAAGGTTTAAGTCACACATGCTACACTCAT

 851 TATTAATCCCTATCATAGCTCTCATGGTGTATAGATGCGGAGGCGGGACT
     ATAATTAGGGATAGTATCGAGAGTACCACATATCTACGCCTCCGCCCTGA

 901 CCA------GGTCCGCAAGGAATTGCAGGGCAG------GGTAGTAGCGG
     GGT------CCAGGCGTTCCTTAACGTCCCGTC------CCATCATCGCC

 951 CGGGGGATGTATGGATCCTGAGCCCATAGTGCGTATCGTAGGTCGAAATG
     GCCCCCTACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 17B (P3)

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGGTTGGTGTTAGAT
     AGTTCTTACTACCTTGGTAAAATTTAAACATATCACCCAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1843.

Sequence name: pAP324

Note: Nucleotides in bold are found within the mutant preproricin linker region. The '-' symbol within the linker region designate deleted nucleotides.

FIGURE 17C

Amino acid sequence Comparison of Mutant Preproricin Linker Region of PAP324 (MMP-9) to Wild Type

| | |
|---|---|
| Wild type ricin linker: | A chain- C A P P P S S Q F S L L I R P V V P N F N A D V C M D P E -B chain |
| PAP324 (MMP-9) linker: | A chain- C G G G S S - - G P Q G I A G Q - - G S S G G G C M D P E -B chain |

Note: Amino acids in bold are found within the preproricin linker region. The '-' symbol within the linker designate deleted amino acids.

FIGURE 18A

Sequence of pAP325 (MMP-9) Linker Region

WT preproricin linker

```
                                                                  primer 325-3'
                                                  5'- ATTGCAGGGCAG---------AGTAGCGGCGGGGGATGTATGGATCCTGAG -3'
                                                            *********         **   **  **  **  **
-CTCATGGTGTATAGATGCGCACCTCCACCATCGTCACAGTTTTCTTTGCTT|ATAAGGCCAGTGGTACCAAATTTTAATGCTGATGTTTGTATGGATCCTGAGCCC-
-GAGTACCACATATCTACGCGTGGAGGTGGTAGCAGTGTCAAAAGAAACGAA|TATTCCGGTCACCATGGTTTAAAATTACGACTACAAACATACCTAGGACTCGGG-
                     * ******* ** *         * *******
3' -TACCACATATCTACGCCTCCGCCCTGAGGT---------GGCGTTCCT -5'
                      primer 325-5'
```

1) PCR mutagenesis

2) Ligate with pVL1393 pAP325 linker
(MMP-9 variant)

```
GGAGGCGGGACTCCACCGCAAGGA|ATTGCAGGGCAGAGTAGCGGCGGGGGA
CCTCCGCCCTGAGGTGGCGTTCCT|TAACGTCCCGTCTCATCGCCGCCCCCT
```

Note: Nucleotides in bold are found within the preproricin linker region. The '-' symbol within the linker designate deleted nucleotides.

FIGURE 18B (P1)

Sequence of pAP325 insert

```
            10        20        30        40        50
             |         |         |         |         |
  1 GAATTCATGAAACCGGGAGGAAATACTATTGTAATATGGATGTATGCAGT
    CTTAAGTACTTTGGCCCTCCTTTATGATAACATTATACCTACATACGTCA

 51 GGCAACATGGCTTTGTTTTGGATCCACCTCAGGGTGGTCTTTCACATTAG
    CCGTTGTACCGAAACAAAACCTAGGTGGAGTCCCACCAGAAAGTGTAATC

101 AGGATAACAACATATTCCCCAAACAATACCCAATTATAAACTTTACCACA
    TCCTATTGTTGTATAAGGGGTTTGTTATGGGTTAATATTTGAAATGGTGT

151 GCGGGTGCCACTGTGCAAAGCTACACAAACTTTATCAGAGCTGTTCGCGG
    CGCCCACGGTGACACGTTTCGATGTGTTTGAAATAGTCTCGACAAGCGCC

201 TCGTTTAACAACTGGAGCTGATGTGAGACATGAAATACCAGTGTTGCCAA
    AGCAAATTGTTGACCTCGACTACACTCTGTACTTTATGGTCACAACGGTT

251 ACAGAGTTGGTTTGCCTATAAACCAACGGTTTATTTTAGTTGAACTCTCA
    TGTCTCAACCAAACGGATATTTGGTTGCCAAATAAAATCAACTTGAGAGT

301 AATCATGCAGAGCTTTCTGTTACATTAGCGCTGGATGTCACCAATGCATA
    TTAGTACGTCTCGAAAGACAATGTAATCGCGACCTACAGTGGTTACGTAT

351 TGTGGTCGGCTACCGTGCTGGAAATAGCGCATATTTCTTTCATCCTGACA
    ACACCAGCCGATGGCACGACCTTTATCGCGTATAAAGAAAGTAGGACTGT

401 ATCAGGAAGATGCAGAAGCAATCACTCATCTTTTCACTGATGTTCAAAAT
    TAGTCCTTCTACGTCTTCGTTAGTGAGTAGAAAAGTGACTACAAGTTTTA

451 CGATATACATTCGCCTTTGGTGGTAATTATGATAGACTTGAACAACTTGC
    GCTATATGTAAGCGGAAACCACCATTAATACTATCTGAACTTGTTGAACG

501 TGGTAATCTGAGAGAAAATATCGAGTTGGGAAATGGTCCACTAGAGGAGG
    ACCATTAGACTCTCTTTTATAGCTCAACCCTTTACCAGGTGATCTCCTCC

551 CTATCTCAGCGCTTTATTATTACAGTACTGGTGGCACTCAGCTTCCAACT
    GATAGAGTCGCGAAATAATAATGTCATGACCACCGTGAGTCGAAGGTTGA

601 CTGGCTCGTTCCTTTATAATTTGCATCCAAATGATTTCAGAAGCAGCAAG
    GACCGAGCAAGGAAATATTAAACGTAGGTTTACTAAAGTCTTCGTCGTTC

651 ATTCCAATATATTGAGGGAGAAATGCGCACGAGAATTAGGTACAACCGGA
    TAAGGTTATATAACTCCCTCTTTACGCGTGCTCTTAATCCATGTTGGCCT
```

FIGURE 18B (P2)

```
701  GATCTGCACCAGATCCTAGCGTAATTACACTTGAGAATAGTTGGGGGAGA
     CTAGACGTGGTCTAGGATCGCATTAATGTGAACTCTTATCAACCCCCTCT

751  CTTTCCACTGCAATTCAAGAGTCTAACCAAGGAGCCTTTGCTAGTCCAAT
     GAAAGGTGACGTTAAGTTCTCAGATTGGTTCCTCGGAAACGATCAGGTTA

801  TCAACTGCAAAGACGTAATGGTTCCAAATTCAGTGTGTACGATGTGAGTA
     AGTTGACGTTTCTGCATTACCAAGGTTTAAGTCACACATGCTACACTCAT

851  TATTAATCCCTATCATAGCTCTCATGGTGTATAGATGCGGAGGCGGGACT
     ATAATTAGGGATAGTATCGAGAGTACCACATATCTACGCCTCCGCCCTGA

901  CCA---------CCGCAAGGAATTGCAGGGCAG---------AGTAGCGG
     GGT---------GGCGTTCCTTAACGTCCCGTC---------TCATCGCC

951  CGGGGGATGTATGGATCCTGAGCCCATAGTGCGTATCGTAGGTCGAAATG
     GCCCCCTACATACCTAGGACTCGGGTATCACGCATAGCATCCAGCTTTAC

1001 GTCTATGTGTTGATGTTAGGGATGGAAGATTCCACAACGGAAACGCAATA
     CAGATACACAACTACAATCCCTACCTTCTAAGGTGTTGCCTTTGCGTTAT

1051 CAGTTGTGGCCATGCAAGTCTAATACAGATGCAAATCAGCTCTGGACTTT
     GTCAACACCGGTACGTTCAGATTATGTCTACGTTTAGTCGAGACCTGAAA

1101 GAAAAGAGACAATACTATTCGATCTAATGGAAAGTGTTTAACTACTTACG
     CTTTTCTCTGTTATGATAAGCTAGATTACCTTTCACAAATTGATGAATGC

1151 GGTACAGTCCGGGAGTCTATGTGATGATCTATGATTGCAATACTGCTGCA
     CCATGTCAGGCCCTCAGATACACTACTAGATACTAACGTTATGACGACGT

1201 ACTGATGCCACCCGCTGGCAAATATGGGATAATGGAACCATCATAAATCC
     TGACTACGGTGGGCGACCGTTTATACCCTATTACCTTGGTAGTATTTAGG

1251 CAGATCTAGTCTAGTTTTAGCAGCGACATCAGGGAACAGTGGTACCACAC
     GTCTAGATCAGATCAAAATCGTCGCTGTAGTCCCTTGTCACCATGGTGTG

1301 TTACAGTGCAAACCAACATTTATGCCGTTAGTCAAGGTTGGCTTCCTACT
     AATGTCACGTTTGGTTGTAAATACGGCAATCAGTTCCAACCGAAGGATGA

1351 AATAATACACAACCTTTTGTTACAACCATTGTTGGGCTATATGGTCTGTG
     TTATTATGTGTTGGAAAACAATGTTGGTAACAACCCGATATACCAGACAC

1401 CTTGCAAGCAAATAGTGGACAAGTATGGATAGAGGACTGTAGCAGTGAAA
     GAACGTTCGTTTATCACCTGTTCATACCTATCTCCTGACATCGTCACTTT
```

FIGURE 18B (P3)

```
1451 AGGCTGAACAACAGTGGGCTCTTTATGCAGATGGTTCAATACGTCCTCAG
     TCCGACTTGTTGTCACCCGAGAAATACGTCTACCAAGTTATGCAGGAGTC

1501 CAAAACCGAGATAATTGCCTTACAAGTGATTCTAATATACGGGAAACAGT
     GTTTTGGCTCTATTAACGGAATGTTCACTAAGATTATATGCCCTTTGTCA

1551 TGTTAAGATCCTCTCTTGTGGCCCTGCATCCTCTGGCCAACGATGGATGT
     ACAATTCTAGGAGAGAACACCGGGACGTAGGAGACCGGTTGCTACCTACA

1601 TCAAGAATGATGGAACCATTTTAAATTTGTATAGTGGGTTGGTGTTAGAT
     AGTTCTTACTACCTTGGTAAAATTTAAACATATCACCCAACCACAATCTA

1651 GTGAGGCGATCGGATCCGAGCCTTAAACAAATCATTCTTTACCCTCTCCA
     CACTCCGCTAGCCTAGGCTCGGAATTTGTTTAGTAAGAAATGGGAGAGGT

1701 TGGTGACCCAAACCAAATATGGTTACCATTATTTTGATAGACAGATTACT
     ACCACTGGGTTTGGTTTATACCAATGGTAATAAAACTATCTGTCTAATGA

1751 CTCTTGCAGTGTGTGTGTCCTGCCATGAAAATAGATGGCTTAAATAAAAA
     GAGAACGTCACACACACAGGACGGTACTTTTATCTACCGAATTTATTTTT

1801 GGACATTGTAAATTTTGTAACTGAAAGGACAGCAAGTTATATCGAATTCC
     CCTGTAACATTTAAAACATTGACTTTCCTGTCGTTCAATATAGCTTAAGG

1851 TGCAG
     ACGTC
```

Total number of bases is: 1837.

Sequence name: pAP325

Note: Nucleotides in bold are found within the mutant preproricin linker region. The '-' symbol within the linker region designate deleted nucleotides.

FIGURE 18C

Amino acid sequence Comparison of Mutant Preproricin Linker Region of PAP325 (MMP-9) to Wild Type

| | |
|---|---|
| Wild type ricin linker: | A chain- C **A P P P S S Q F S L L I R P V V P N F N A D V** C M D P E -B chain |
| PAP325 (MMP-9) linker: | A chain- C **G G G S S - - - P Q G I A G Q - - - S S G G G** C M D P E -B chain |

Note: Amino acids in bold are found within the preproricin linker region. The '-' symbol within the linker designate deleted amino acids.

Cleavage of Proricin Variants by Matrix Metalloprotease-9

| | |
|---|---|
| A | PAP220 (500 ng) |
| B | PAP220 (500 ng) digested with 100 ng MMP9 |
| C | PAP323 (500 ng) |
| D | PAP323 (500 ng) digested with 100 ng MMP9 |
| E | PAP324 (500 ng) |
| F | PAP324 (500 ng) digested with 100 ng MMP9 |
| G | PAP325 (500 ng) |
| H | PAP325 (500 ng) digested with 100 ng MMP9 |

SEQUENCE LISTING

<160> NUMBER OF SEQ ID NOS: 130

<210> SEQ ID NO 1
<211> LENGTH: 30
<212> TYPE: DNA
<213> ORGANISM: E. coli

<400> SEQUENCE: 1
atgtggggac aacgaaattt taatgctgat 30

<210> SEQ ID NO 2
<211> LENGTH: 105
<212> TYPE: DNA
<213> ORGANISM: E. coli

<400> SEQUENCE: 2
ctcatggtgt atagatgcgc acctccacca tcgtcacagt tttctttgct tataaggcca 60
gtggtaccaa attttaatgc tgatgtttgt atggatcctg agccc 105

<210> SEQ ID NO 3
<211> LENGTH: 30
<212> TYPE: DNA
<213> ORGANISM: E. coli

<400> SEQUENCE: 3
ggtggtagca gtgtcaaacc aggagaaccg 30

<210> SEQ ID NO 4
<211> LENGTH: 69
<212> TYPE: DNA
<213> ORGANISM: E. coli

<400> SEQUENCE: 4
gcacctccac catcgtcaca gtttggtcct cttggcatgt ggggacaacg aaattttaat 60
gctgatgtt 69

<210> SEQ ID NO 5
<211> LENGTH: 1855
<212> TYPE: DNA
<213> ORGANISM: E. coli

<400> SEQUENCE: 5
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgaaatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720

-continued

```
gtaattacac ttgagaatag ttgggggaga ctttccactg caattcaaga gtctaaccaa    780
ggagcctttg ctagtccaat tcaactgcaa agacgtaatg gttccaaatt cagtgtgtac    840
gatgtgagta tattaatccc tatcatagct ctcatggtgt atagatgcgc acctccacca    900
tcgtcacagt ttggtcctct tggcatgtgg ggacaacgaa attttaatgc tgatgtttgt    960
atggatcctg agcccatagt gcgtatcgta ggtcgaaatg gtctatgtgt tgatgttagg   1020
gatggaagat tccacaacgg aaacgcaata cagttgtggc catgcaagtc taatacagat   1080
gcaaatcagc tctggacttt gaaaagagac aatactattc gatctaatgg aaagtgttta   1140
actacttacg ggtacagtcc gggagtctat gtgatgatct atgattgcaa tactgctgca   1200
actgatgcca cccgctggca aatatgggat aatggaacca tcataaatcc cagatctagt   1260
ctagttttag cagcgacatc agggaacagt ggtaccacac ttacagtgca aaccaacatt   1320
tatgccgtta gtcaaggttg gcttcctact aataatacac aaccttttgt tacaaccatt   1380
gttgggctat atggtctgtg cttgcaagca aatagtggac aagtatggat agaggactgt   1440
agcagtgaaa aggctgaaca acagtgggct ctttatgcag atggttcaat acgtcctcag   1500
caaaaccgag ataattgcct tacaagtgat tctaatatac gggaaacagt tgttaagatc   1560
ctctcttgtg gccctgcatc ctctggccaa cgatggatgt tcaagaatga tggaaccatt   1620
ttaaatttgt atagtgggtt ggtgttagat gtgaggcgat cggatccgag ccttaaacaa   1680
atcattcttt accctctcca tggtgaccca aaccaaatat ggttaccatt attttgatag   1740
acagattact ctcttgcagt gtgtgtgtcc tgccatgaaa atagatggct taaataaaaa   1800
ggacattgta aattttgtaa ctgaaaggac agcaagttat atcgaattcc tgcag         1855
```

<210> SEQ ID NO 6
<211> LENGTH: 29
<212> TYPE: PRT
<213> ORGANISM: E. coli

<400> SEQUENCE: 6

```
Cys Ala Pro Pro Pro Ser Ser Gln Phe Ser Leu Leu Ile Arg Pro Val
1               5                   10                  15

Val Pro Asn Phe Asn Ala Asp Val Cys Met Asp Pro Glu
            20                  25
```

<210> SEQ ID NO 7
<211> LENGTH: 29
<212> TYPE: PRT
<213> ORGANISM: E. coli

<400> SEQUENCE: 7

```
Cys Ala Pro Pro Pro Ser Ser Gln Phe Gly Pro Leu Gly Met Trp Gly
1               5                   10                  15

Gln Arg Asn Phe Asn Ala Asp Val Cys Met Asp Pro Glu
            20                  25
```

<210> SEQ ID NO 8
<211> LENGTH: 24
<212> TYPE: DNA
<213> ORGANISM: E. coli

<400> SEQUENCE: 8

```
gggcagtgta tggatcctga gccc                                            24
```

<210> SEQ ID NO 9

-continued

<211> LENGTH: 105
<212> TYPE: DNA
<213> ORGANISM: E. coli

<400> SEQUENCE: 9
ctcatggtgt atagatgcgc acctccacca tcgtcacagt tttctttgct tataaggcca 60
gtggtaccaa attttaatgc tgatgtttgt atggatcctg agccc 105

<210> SEQ ID NO 10
<211> LENGTH: 30
<212> TYPE: DNA
<213> ORGANISM: E. coli

<400> SEQUENCE: 10
agcagtgtca aaagaggcgt tccttaacgt 30

<210> SEQ ID NO 11
<211> LENGTH: 48
<212> TYPE: DNA
<213> ORGANISM: E. coli

<400> SEQUENCE: 11
gcacctccac catcgtcaca gttttctccg caaggaattg cagggcag 48

<210> SEQ ID NO 12
<211> LENGTH: 1834
<212> TYPE: DNA
<213> ORGANISM: E. coli

<400> SEQUENCE: 12
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgaaatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt tttctccgca aggaattgca gggcagtgta tggatcctga gcccatagtg 960
cgtatcgtag gtcgaaatgg tctatgtgtt gatgttaggg atggaagatt ccacaacgga 1020
aacgcaatac agttgtggcc atgcaagtct aatacagatg caaatcagct ctggactttg 1080
aaaagagaca atactattcg atctaatgga aagtgtttaa ctacttacgg gtacagtccg 1140
ggagtctatg tgatgatcta tgattgcaat actgctgcaa ctgatgccac ccgctggcaa 1200
atatgggata atggaaccat cataaatccc agatctagtc tagttttagc agcgacatca 1260

-continued gggaacagtg gtaccacact tacagtgcaa accaacattt atgccgttag tcaaggttgg 1320
cttcctacta ataatacaca accttttgtt acaaccattg ttgggctata tggtctgtgc 1380
ttgcaagcaa atagtggaca agtatggata gaggactgta gcagtgaaaa ggctgaacaa 1440
cagtgggctc tttatgcaga tggttcaata cgtcctcagc aaaaccgaga taattgcctt 1500
acaagtgatt ctaatatacg ggaaacagtt gttaagatcc tctcttgtgg ccctgcatcc 1560
tctggccaac gatggatgtt caagaatgat ggaaccattt taaatttgta tagtgggttg 1620
gtgttagatg tgaggcgatc ggatccgagc cttaaacaaa tcattcttta ccctctccat 1680
ggtgacccaa accaaatatg gttaccatta ttttgataga cagattactc tcttgcagtg 1740
tgtgtgtcct gccatgaaaa tagatggctt aaataaaaag gacattgtaa attttgtaac 1800
tgaaaggaca gcaagttata tcgaattcct gcag 1834

<210> SEQ ID NO 13
<211> LENGTH: 29
<212> TYPE: PRT
<213> ORGANISM: E. coli

<400> SEQUENCE: 13

Cys Ala Pro Pro Pro Ser Ser Gln Phe Ser Leu Leu Ile Arg Pro Val
1 5 10 15

Val Pro Asn Phe Asn Ala Asp Val Cys Met Asp Pro Glu
20 25

<210> SEQ ID NO 14
<211> LENGTH: 22
<212> TYPE: PRT
<213> ORGANISM: E. coli

<400> SEQUENCE: 14

Cys Ala Pro Pro Pro Ser Ser Gln Phe Ser Pro Gln Gly Ile Ala Gly
1 5 10 15

Gln Cys Met Asp Pro Glu
20

<210> SEQ ID NO 15
<211> LENGTH: 24
<212> TYPE: DNA
<213> ORGANISM: E. coli

<400> SEQUENCE: 15
gggcagcgaa attttaatgc tgat 24

<210> SEQ ID NO 16
<211> LENGTH: 105
<212> TYPE: DNA
<213> ORGANISM: E. coli

<400> SEQUENCE: 16
ctcatggtgt atagatgcgc acctccacca tcgtcacagt tttctttgct tataaggcca 60
gtggtaccaa attttaatgc tgatgtttgt atggatcctg agccc 105

<210> SEQ ID NO 17
<211> LENGTH: 36
<212> TYPE: DNA
<213> ORGANISM: E. coli

<400> SEQUENCE: 17

-continued gagtaccaca tatctacgag aggcgttcct taacgt 36

<210> SEQ ID NO 18
<211> LENGTH: 45
<212> TYPE: DNA
<213> ORGANISM: E. coli

<400> SEQUENCE: 18
tctccgcaag gaattgcagg gcagcgaaat tttaatgctg atgtt 45

<210> SEQ ID NO 19
<211> LENGTH: 1831
<212> TYPE: DNA
<213> ORGANISM: E. coli

<400> SEQUENCE: 19
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgaaatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgctc tccgcaagga 900
attgcagggc agcgaaattt taatgctgat gtttgtatgg atcctgagcc catagtgcgt 960
atcgtaggtc gaaatggtct atgtgttgat gttagggatg gaagattcca caacggaaac 1020
gcaatacagt tgtggccatg caagtctaat acagatgcaa atcagctctg gactttgaaa 1080
agagacaata ctattcgatc taatggaaag tgtttaacta cttacgggta cagtccggga 1140
gtctatgtga tgatctatga ttgcaatact gctgcaactg atgccacccg ctggcaaata 1200
tgggataatg gaaccatcat aaatcccaga tctagtctag ttttagcagc gacatcaggg 1260
aacagtggta ccacacttac agtgcaaacc aacatttatg ccgttagtca aggttggctt 1320
cctactaata atacacaacc ttttgttaca accattgttg ggctatatgg tctgtgcttg 1380
caagcaaata gtggacaagt atggatagag gactgtagca gtgaaaaggc tgaacaacag 1440
tgggctcttt atgcagatgg ttcaatacgt cctcagcaaa accgagataa ttgccttaca 1500
agtgattcta atatacggga aacagttgtt aagatcctct cttgtggccc tgcatcctct 1560
ggccaacgat ggatgttcaa gaatgatgga accattttaa atttgtatag tgggttggtg 1620
ttagatgtga ggcgatcgga tccgagcctt aaacaaatca ttctttaccc tctccatggt 1680
gacccaaacc aaatatggtt accattattt tgatagacag attactctct tgcagtgtgt 1740
gtgtcctgcc atgaaaatag atggcttaaa taaaaaggac attgtaaatt ttgtaactga 1800

-continued

```
aaggacagca agttatatcg aattcctgca g                                 1831


<210> SEQ ID NO 20
<211> LENGTH: 29
<212> TYPE: PRT
<213> ORGANISM: E. coli

<400> SEQUENCE: 20

Cys Ala Pro Pro Pro Ser Ser Gln Phe Ser Leu Leu Ile Arg Pro Val
1               5                   10                  15

Val Pro Asn Phe Asn Ala Asp Val Cys Met Asp Pro Glu
            20                  25


<210> SEQ ID NO 21
<211> LENGTH: 21
<212> TYPE: PRT
<213> ORGANISM: E. coli

<400> SEQUENCE: 21

Cys Ser Pro Gln Gly Ile Ala Gly Gln Arg Asn Phe Asn Ala Asp Val
1               5                   10                  15

Cys Met Asp Pro Glu
            20


<210> SEQ ID NO 22
<211> LENGTH: 24
<212> TYPE: DNA
<213> ORGANISM: E. coli

<400> SEQUENCE: 22

gggcagtgta tggatcctga gccc                                          24


<210> SEQ ID NO 23
<211> LENGTH: 105
<212> TYPE: DNA
<213> ORGANISM: E. coli

<400> SEQUENCE: 23

ctcatggtgt atagatgcgc acctccacca tcgtcacagt tttctttgct tataaggcca    60

gtggtaccaa attttaatgc tgatgtttgt atggatcctg agccc                  105


<210> SEQ ID NO 24
<211> LENGTH: 36
<212> TYPE: DNA
<213> ORGANISM: E. coli

<400> SEQUENCE: 24

gagtaccaca tatctacgag aggcgttcct taacgt                             36


<210> SEQ ID NO 25
<211> LENGTH: 24
<212> TYPE: DNA
<213> ORGANISM: E. coli

<400> SEQUENCE: 25

tctccgcaag gaattgcagg gcag                                          24


<210> SEQ ID NO 26
<211> LENGTH: 1810
<212> TYPE: DNA
<213> ORGANISM: E. coli
```

-continued

<400> SEQUENCE: 26

```
gaattcatga aaccgggagg aaatactatt gtaatatgga tgtatgcagt ggcaacatgg     60
ctttgttttg gatccacctc agggtggtct ttcacattag aggataacaa catattcccc    120
aaacaatacc caattataaa ctttaccaca gcgggtgcca ctgtgcaaag ctacacaaac    180
tttatcagag ctgttcgcgg tcgtttaaca actggagctg atgtgagaca tgaaatacca    240
gtgttgccaa acagagttgg tttgcctata aaccaacggt ttattttagt tgaactctca    300
aatcatgcag agctttctgt tacattagcg ctggatgtca ccaatgcata tgtggtcggc    360
taccgtgctg gaaatagcgc atatttcttt catcctgaca atcaggaaga tgcagaagca    420
atcactcatc ttttcactga tgttcaaaat cgatatacat tcgcctttgg tggtaattat    480
gatagacttg aacaacttgc tggtaatctg agagaaaata tcgagttggg aaatggtcca    540
ctagaggagg ctatctcagc gctttattat tacagtactg gtggcactca gcttccaact    600
ctggctcgtt cctttataat ttgcatccaa atgatttcag aagcagcaag attccaatat    660
attgagggag aaatgcgcac gagaattagg tacaaccgga gatctgcacc agatcctagc    720
gtaattacac ttgagaatag ttgggggaga ctttccactg caattcaaga gtctaaccaa    780
ggagcctttg ctagtccaat tcaactgcaa agacgtaatg gttccaaatt cagtgtgtac    840
gatgtgagta tattaatccc tatcatagct ctcatggtgt atagatgctc tccgcaagga    900
attgcagggc agtgtatgga tcctgagccc atagtgcgta tcgtaggtcg aaatggtcta    960
tgtgttgatg ttagggatgg aagattccac aacggaaacg caatacagtt gtggccatgc   1020
aagtctaata cagatgcaaa tcagctctgg actttgaaaa gagacaatac tattcgatct   1080
aatggaaagt gtttaactac ttacgggtac agtccgggag tctatgtgat gatctatgat   1140
tgcaatactg ctgcaactga tgccacccgc tggcaaatat gggataatgg aaccatcata   1200
aatcccagat ctagtctagt tttagcagcg acatcaggga acagtggtac cacacttaca   1260
gtgcaaacca acatttatgc cgttagtcaa ggttggcttc ctactaataa tacacaacct   1320
tttgttacaa ccattgttgg gctatatggt ctgtgcttgc aagcaaatag tggacaagta   1380
tggatagagg actgtagcag tgaaaaggct gaacaacagt gggctcttta tgcagatggt   1440
tcaatacgtc ctcagcaaaa ccgagataat tgccttacaa gtgattctaa tatacgggaa   1500
acagttgtta agatcctctc ttgtggccct gcatcctctg gccaacgatg gatgttcaag   1560
aatgatggaa ccattttaaa tttgtatagt gggttggtgt tagatgtgag gcgatcggat   1620
ccgagcctta aacaaatcat tctttaccct ctccatggtg acccaaacca aatatggtta   1680
ccattatttt gatagacaga ttactctctt gcagtgtgtg tgtcctgcca tgaaaataga   1740
tggcttaaat aaaaaggaca ttgtaaattt tgtaactgaa aggacagcaa gttatatcga   1800
attcctgcag                                                          1810
```

<210> SEQ ID NO 27
<211> LENGTH: 29
<212> TYPE: PRT
<213> ORGANISM: E. coli

<400> SEQUENCE: 27

```
Cys Ala Pro Pro Pro Ser Ser Gln Phe Ser Leu Leu Ile Arg Pro Val
1               5                   10                  15

Val Pro Asn Phe Asn Ala Asp Val Cys Met Asp Pro Glu
            20                  25
```

-continued

<210> SEQ ID NO 28
<211> LENGTH: 14
<212> TYPE: PRT
<213> ORGANISM: E. coli

<400> SEQUENCE: 28

Cys Ser Pro Gln Gly Ile Ala Gly Gln Cys Met Asp Pro Glu
1 5 10

<210> SEQ ID NO 29
<211> LENGTH: 24
<212> TYPE: DNA
<213> ORGANISM: E. coli

<400> SEQUENCE: 29
gggcagtgta tggatcctga gccc 24

<210> SEQ ID NO 30
<211> LENGTH: 105
<212> TYPE: DNA
<213> ORGANISM: E. coli

<400> SEQUENCE: 30
ctcatggtgt atagatgcgc acctccacca tcgtcacagt tttctttgct tataaggcca 60
gtggtaccaa attttaatgc tgatgtttgt atggatcctg agccc 105

<210> SEQ ID NO 31
<211> LENGTH: 36
<212> TYPE: DNA
<213> ORGANISM: E. coli

<400> SEQUENCE: 31
tctacgcgtg gaggtggtag aggcgttcct taacgt 36

<210> SEQ ID NO 32
<211> LENGTH: 36
<212> TYPE: DNA
<213> ORGANISM: E. coli

<400> SEQUENCE: 32
gcacctccac catctccgca aggaattgca gggcag 36

<210> SEQ ID NO 33
<211> LENGTH: 1822
<212> TYPE: DNA
<213> ORGANISM: E. coli

<400> SEQUENCE: 33
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgaaatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600

-continued ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tctccgcaag gaattgcagg gcagtgtatg gatcctgagc ccatagtgcg tatcgtaggt 960
cgaaatggtc tatgtgttga tgttagggat ggaagattcc acaacggaaa cgcaatacag 1020
ttgtggccat gcaagtctaa tacagatgca aatcagctct ggactttgaa aagagacaat 1080
actattcgat ctaatggaaa gtgtttaact acttacgggt acagtccggg agtctatgtg 1140
atgatctatg attgcaatac tgctgcaact gatgccaccc gctggcaaat atgggataat 1200
ggaaccatca taaatcccag atctagtcta gttttagcag cgacatcagg gaacagtggt 1260
accacactta cagtgcaaac caacatttat gccgttagtc aaggttggct tcctactaat 1320
aatacacaac cttttgttac aaccattgtt gggctatatg gtctgtgctt gcaagcaaat 1380
agtggacaag tatggataga ggactgtagc agtgaaaagg ctgaacaaca gtgggctctt 1440
tatgcagatg gttcaatacg tcctcagcaa aaccgagata attgccttac aagtgattct 1500
aatatacggg aaacagttgt taagatcctc tcttgtggcc ctgcatcctc tggccaacga 1560
tggatgttca agaatgatgg aaccatttta aatttgtata gtgggttggt gttagatgtg 1620
aggcgatcgg atccgagcct taaacaaatc attctttacc ctctccatgg tgacccaaac 1680
caaatatggt taccattatt ttgatagaca gattactctc ttgcagtgtg tgtgtcctgc 1740
catgaaaata gatggcttaa ataaaaagga cattgtaaat tttgtaactg aaaggacagc 1800
aagttatatc gaattcctgc ag 1822

<210> SEQ ID NO 34
<211> LENGTH: 29
<212> TYPE: PRT
<213> ORGANISM: E. coli

<400> SEQUENCE: 34

Cys Ala Pro Pro Pro Ser Ser Gln Phe Ser Leu Leu Ile Arg Pro Val
1 5 10 15

Val Pro Asn Phe Asn Ala Asp Val Cys Met Asp Pro Glu
20 25

<210> SEQ ID NO 35
<211> LENGTH: 18
<212> TYPE: PRT
<213> ORGANISM: E. coli

<400> SEQUENCE: 35

Cys Ala Pro Pro Pro Ser Pro Gln Gly Ile Ala Gly Gln Cys Met Asp
1 5 10 15

Pro Glu

<210> SEQ ID NO 36
<211> LENGTH: 45
<212> TYPE: DNA
<213> ORGANISM: E. coli

<400> SEQUENCE: 36
atgtggggac aatgtggtgg cggagggccc atagtgcgta tcgta 45

-continued

<210> SEQ ID NO 37
<211> LENGTH: 120
<212> TYPE: DNA
<213> ORGANISM: E. coli

<400> SEQUENCE: 37
ctcatggtgt atagatgcgc acctccacca tcgtcacagt tttctttgct tataaggcca 60
gtggtaccaa attttaatgc tgatgtttgt atggatcctg agcccatagt gcgtatcgta 120

<210> SEQ ID NO 38
<211> LENGTH: 30
<212> TYPE: DNA
<213> ORGANISM: E. coli

<400> SEQUENCE: 38
tctacgcgtg gaggtggtcc aggagaaccg 30

<210> SEQ ID NO 39
<211> LENGTH: 36
<212> TYPE: DNA
<213> ORGANISM: E. coli

<400> SEQUENCE: 39
gcacctccac caggtcctct tggcatgtgg ggacaa 36

<210> SEQ ID NO 40
<211> LENGTH: 1822
<212> TYPE: DNA
<213> ORGANISM: E. coli

<400> SEQUENCE: 40
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgaaatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
ggtcctcttg gcatgtgggg acaatgtggt ggcggagggc ccatagtgcg tatcgtaggt 960
cgaaatggtc tatgtgttga tgttagggat ggaagattcc acaacggaaa cgcaatacag 1020
ttgtggccat gcaagtctaa tacagatgca aatcagctct ggactttgaa aagagacaat 1080
actattcgat ctaatggaaa gtgtttaact acttacgggt acagtccggg agtctatgtg 1140

-continued

```
atgatctatg attgcaatac tgctgcaact gatgccaccc gctggcaaat atgggataat   1200

ggaaccatca taaatcccag atctagtcta gttttagcag cgacatcagg gaacagtggt   1260

accacactta cagtgcaaac caacatttat gccgttagtc aaggttggct tcctactaat   1320

aatacacaac cttttgttac aaccattgtt gggctatatg gtctgtgctt gcaagcaaat   1380

agtggacaag tatggataga ggactgtagc agtgaaaagg ctgaacaaca gtgggctctt   1440

tatgcagatg gttcaatacg tcctcagcaa aaccgagata attgccttac aagtgattct   1500

aatatacggg aaacagttgt taagatcctc tcttgtggcc ctgcatcctc tggccaacga   1560

tggatgttca agaatgatgg aaccatttta aatttgtata gtgggttggt gttagatgtg   1620

aggcgatcgg atccgagcct taaacaaatc attctttacc ctctccatgg tgacccaaac   1680

caaatatggt taccattatt ttgatagaca gattactctc ttgcagtgtg tgtgtcctgc   1740

catgaaaata gatggcttaa ataaaaagga cattgtaaat tttgtaactg aaaggacagc   1800

aagttatatc gaattcctgc ag                                             1822
```

<210> SEQ ID NO 41
<211> LENGTH: 29
<212> TYPE: PRT
<213> ORGANISM: E. coli

<400> SEQUENCE: 41

```
Cys Ala Pro Pro Pro Ser Ser Gln Phe Ser Leu Leu Ile Arg Pro Val
1               5                   10                  15

Val Pro Asn Phe Asn Ala Asp Val Cys Met Asp Pro Glu
            20                  25
```

<210> SEQ ID NO 42
<211> LENGTH: 18
<212> TYPE: PRT
<213> ORGANISM: E. coli

<400> SEQUENCE: 42

```
Cys Ala Pro Pro Pro Gly Pro Leu Gly Met Trp Gly Gln Cys Gly Gly
1               5                   10                  15

Gly Gly
```

<210> SEQ ID NO 43
<211> LENGTH: 48
<212> TYPE: DNA
<213> ORGANISM: E. coli

<400> SEQUENCE: 43

```
tttaatgctg atgtttgtgg tggcggaggg cccatagtgc gtatcgta                  48
```

<210> SEQ ID NO 44
<211> LENGTH: 120
<212> TYPE: DNA
<213> ORGANISM: E. coli

<400> SEQUENCE: 44

```
ctcatggtgt atagatgcgc acctccacca tcgtcacagt tttctttgct tataaggcca     60

gtggtaccaa attttaatgc tgatgtttgt atggatcctg agcccatagt gcgtatcgta    120
```

<210> SEQ ID NO 45
<211> LENGTH: 48
<212> TYPE: DNA
<213> ORGANISM: E. coli

-continued

<400> SEQUENCE: 45
ggtggtagca gtgtcaaacc aggagaaccg tacacccctg ttgcttta 48

<210> SEQ ID NO 46
<211> LENGTH: 69
<212> TYPE: DNA
<213> ORGANISM: E. coli

<400> SEQUENCE: 46
gcacctccac catcgtcaca gtttggtcct cttggcatgt ggggacaacg aaattttaat 60
gctgatgtt 69

<210> SEQ ID NO 47
<211> LENGTH: 1855
<212> TYPE: DNA
<213> ORGANISM: E. coli

<400> SEQUENCE: 47
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgaaatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcacagt ttggtcctct tggcatgtgg ggacaacgaa attttaatgc tgatgtttgt 960
ggtggcggag ggcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aacctttgt tacaaccatt 1380 gttgggctat atggtctgtg cttgcaagca aatagtggac aagtatggat agaggactgt 1440
agcagtgaaa aggctgaaca acagtgggct ctttatgcag atggttcaat acgtcctcag 1500
caaaaccgag ataattgcct tacaagtgat tctaatatac gggaaacagt tgttaagatc 1560
ctctcttgtg gccctgcatc ctctggccaa cgatggatgt tcaagaatga tggaaccatt 1620
ttaaatttgt atagtgggtt ggtgttagat gtgaggcgat cggatccgag ccttaaacaa 1680

-continued atcattcttt accctctcca tggtgaccca aaccaaatat ggttaccatt attttgatag 1740
acagattact ctcttgcagt gtgtgtgtcc tgccatgaaa atagatggct taaataaaaa 1800
ggacattgta aattttgtaa ctgaaaggac agcaagttat atcgaattcc tgcag 1855

<210> SEQ ID NO 48
<211> LENGTH: 29
<212> TYPE: PRT
<213> ORGANISM: E. coli

<400> SEQUENCE: 48

Cys Ala Pro Pro Pro Ser Ser Gln Phe Ser Leu Leu Ile Arg Pro Val
1 5 10 15

Val Pro Asn Phe Asn Ala Asp Val Cys Met Asp Pro Glu
20 25

<210> SEQ ID NO 49
<211> LENGTH: 29
<212> TYPE: PRT
<213> ORGANISM: E. coli

<400> SEQUENCE: 49

Cys Ala Pro Pro Pro Ser Ser Gln Phe Gly Pro Leu Gly Met Trp Gly
1 5 10 15

Gln Arg Asn Phe Asn Ala Asp Val Cys Gly Gly Gly Gly
20 25

<210> SEQ ID NO 50
<211> LENGTH: 27
<212> TYPE: DNA
<213> ORGANISM: E. coli

<400> SEQUENCE: 50
gtagtcggcg ggtgtatgga tcctgag 27

<210> SEQ ID NO 51
<211> LENGTH: 105
<212> TYPE: DNA
<213> ORGANISM: E. coli

<400> SEQUENCE: 51
ctcatggtgt atagatgcgc acctccacca tcgtcacagt tttctttgct tataaggcca 60
gtggtaccaa attttaatgc tgatgtttgt atggatcctg agccc 105

<210> SEQ ID NO 52
<211> LENGTH: 24
<212> TYPE: DNA
<213> ORGANISM: E. coli

<400> SEQUENCE: 52
taccacatat ctacgggtcc tgct 24

<210> SEQ ID NO 53
<211> LENGTH: 21
<212> TYPE: DNA
<213> ORGANISM: E. coli

<400> SEQUENCE: 53
ccaggacgag tagtcggcgg g 21

<210> SEQ ID NO 54

-continued

<211> LENGTH: 1807
<212> TYPE: DNA
<213> ORGANISM: E. coli

<400> SEQUENCE: 54
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgaaatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgccc aggacgagta 900
gtcggcgggt gtatggatcc tgagcccata gtgcgtatcg taggtcgaaa tggtctatgt 960
gttgatgtta gggatggaag attccacaac ggaaacgcaa tacagttgtg gccatgcaag 1020
tctaatacag atgcaaatca gctctggact ttgaaaagag acaatactat tcgatctaat 1080
ggaaagtgtt taactactta cgggtacagt ccgggagtct atgtgatgat ctatgattgc 1140
aatactgctg caactgatgc cacccgctgg caaatatggg ataatggaac catcataaat 1200
cccagatcta gtctagtttt agcagcgaca tcagggaaca gtggtaccac acttacagtg 1260
caaaccaaca tttatgccgt tagtcaaggt tggcttccta ctaataatac acaacctttt 1320
gttacaacca ttgttgggct atatggtctg tgcttgcaag caaatagtgg acaagtatgg 1380
atagaggact gtagcagtga aaaggctgaa caacagtggg ctctttatgc agatggttca 1440
atacgtcctc agcaaaaccg agataattgc cttacaagtg attctaatat acgggaaaca 1500
gttgttaaga tcctctcttg tggccctgca tcctctggcc aacgatggat gttcaagaat 1560
gatggaacca ttttaaattt gtatagtggg ttggtgttag atgtgaggcg atcggatccg 1620
agccttaaac aaatcattct ttaccctctc catggtgacc caaaccaaat atggttacca 1680
ttattttgat agacagatta ctctcttgca gtgtgtgtgt cctgccatga aaatagatgg 1740
cttaaataaa aaggacattg taaattttgt aactgaaagg acagcaagtt atatcgaatt 1800
cctgcag 1807

<210> SEQ ID NO 55
<211> LENGTH: 29
<212> TYPE: PRT
<213> ORGANISM: E. coli

<400> SEQUENCE: 55

Cys Ala Pro Pro Pro Ser Ser Gln Phe Ser Leu Leu Ile Arg Pro Val
1 5 10 15

-continued

```
Val Pro Asn Phe Asn Ala Asp Val Cys Met Asp Pro Glu
            20                  25


<210> SEQ ID NO 56
<211> LENGTH: 13
<212> TYPE: PRT
<213> ORGANISM: E. coli

<400> SEQUENCE: 56

Cys Pro Gly Arg Val Val Gly Gly Cys Met Asp Pro Glu
1               5                   10


<210> SEQ ID NO 57
<211> LENGTH: 39
<212> TYPE: DNA
<213> ORGANISM: E. coli

<400> SEQUENCE: 57

gtagtcggcg ggggaggcgg gggttgtatg gatcctgag                            39


<210> SEQ ID NO 58
<211> LENGTH: 105
<212> TYPE: DNA
<213> ORGANISM: E. coli

<400> SEQUENCE: 58

ctcatggtgt atagatgcgc acctccacca tcgtcacagt tttctttgct tataaggcca     60

gtggtaccaa attttaatgc tgatgtttgt atggatcctg agccc                    105


<210> SEQ ID NO 59
<211> LENGTH: 36
<212> TYPE: DNA
<213> ORGANISM: E. coli

<400> SEQUENCE: 59

taccacatat ctacgcctcc gcccccaggt cctgct                               36


<210> SEQ ID NO 60
<211> LENGTH: 45
<212> TYPE: DNA
<213> ORGANISM: E. coli

<400> SEQUENCE: 60

ggaggcgggg gtccaggacg agtagtcggc gggggaggcg ggggt                     45


<210> SEQ ID NO 61
<211> LENGTH: 1831
<212> TYPE: DNA
<213> ORGANISM: E. coli

<400> SEQUENCE: 61

gaattcatga aaccgggagg aaatactatt gtaatatgga tgtatgcagt ggcaacatgg     60

ctttgttttg gatccacctc agggtggtct ttcacattag aggataacaa catattcccc    120

aaacaatacc caattataaa ctttaccaca gcgggtgcca ctgtgcaaag ctacacaaac    180

tttatcagag ctgttcgcgg tcgtttaaca actggagctg atgtgagaca tgaaatacca    240

gtgttgccaa acagagttgg tttgcctata aaccaacggt ttattttagt tgaactctca    300

aatcatgcag agctttctgt tacattagcg ctggatgtca ccaatgcata tgtggtcggc    360

taccgtgctg gaaatagcgc atatttcttt catcctgaca atcaggaaga tgcagaagca    420

atcactcatc ttttcactga tgttcaaaat cgatatacat tcgcctttgg tggtaattat    480
```

-continued

```
gatagacttg aacaacttgc tggtaatctg agagaaaata tcgagttggg aaatggtcca    540
ctagaggagg ctatctcagc gctttattat tacagtactg gtggcactca gcttccaact    600
ctggctcgtt cctttataat ttgcatccaa atgatttcag aagcagcaag attccaatat    660
attgagggag aaatgcgcac gagaattagg tacaaccgga gatctgcacc agatcctagc    720
gtaattacac ttgagaatag ttgggggaga ctttccactg caattcaaga gtctaaccaa    780
ggagcctttg ctagtccaat tcaactgcaa agacgtaatg gttccaaatt cagtgtgtac    840
gatgtgagta tattaatccc tatcatagct ctcatggtgt atagatgcgg aggcgggggt    900
ccaggacgag tagtcggcgg gggaggcggg ggttgtatgg atcctgagcc catagtgcgt    960
atcgtaggtc gaaatggtct atgtgttgat gttagggatg gaagattcca caacggaaac   1020
gcaatacagt tgtggccatg caagtctaat acagatgcaa atcagctctg gactttgaaa   1080
agagacaata ctattcgatc taatggaaag tgtttaacta cttacgggta cagtccggga   1140
gtctatgtga tgatctatga ttgcaatact gctgcaactg atgccacccg ctggcaaata   1200
tgggataatg gaaccatcat aaatcccaga tctagtctag ttttagcagc gacatcaggg   1260
aacagtggta ccacacttac agtgcaaacc aacatttatg ccgttagtca aggttggctt   1320
cctactaata atacacaacc ttttgttaca accattgttg ggctatatgg tctgtgcttg   1380
caagcaaata gtggacaagt atggatagag gactgtagca gtgaaaaggc tgaacaacag   1440
tgggctcttt atgcagatgg ttcaatacgt cctcagcaaa accgagataa ttgccttaca   1500
agtgattcta atatacggga aacagttgtt aagatcctct cttgtggccc tgcatcctct   1560
ggccaacgat ggatgttcaa gaatgatgga accattttaa atttgtatag tgggttggtg   1620
ttagatgtga ggcgatcgga tccgagcctt aaacaaatca ttctttaccc tctccatggt   1680
gacccaaacc aaatatggtt accattattt tgatagacag attactctct tgcagtgtgt   1740
gtgtcctgcc atgaaaatag atggcttaaa taaaaaggac attgtaaatt ttgtaactga   1800
aaggacagca agttatatcg aattcctgca g                                  1831


<210> SEQ ID NO 62
<211> LENGTH: 28
<212> TYPE: PRT
<213> ORGANISM: E. coli

<400> SEQUENCE: 62

Ala Pro Pro Pro Ser Ser Gln Phe Ser Leu Leu Ile Arg Pro Val Val
1               5                   10                  15

Pro Asn Phe Asn Ala Asp Val Cys Met Asp Pro Glu
            20                  25


<210> SEQ ID NO 63
<211> LENGTH: 21
<212> TYPE: PRT
<213> ORGANISM: E. coli

<400> SEQUENCE: 63

Cys Gly Gly Gly Gly Pro Gly Arg Val Val Gly Gly Gly Gly Gly Gly
1               5                   10                  15

Cys Met Asp Pro Glu
            20


<210> SEQ ID NO 64
<211> LENGTH: 36
<212> TYPE: DNA
```

-continued

<213> ORGANISM: E. coli

<400> SEQUENCE: 64
ccaggacgag tagtcggcgg gtgtatggat cctgag 36

<210> SEQ ID NO 65
<211> LENGTH: 105
<212> TYPE: DNA
<213> ORGANISM: E. coli

<400> SEQUENCE: 65
ctcatggtgt atagatgcgc acctccacca tcgtcacagt tttctttgct tataaggcca 60
gtggtaccaa attttaatgc tgatgtttgt atggatcctg agccc 105

<210> SEQ ID NO 66
<211> LENGTH: 36
<212> TYPE: DNA
<213> ORGANISM: E. coli

<400> SEQUENCE: 66
taccacatat ctacgggtcc tgctcatcag ccgccc 36

<210> SEQ ID NO 67
<211> LENGTH: 42
<212> TYPE: DNA
<213> ORGANISM: E. coli

<400> SEQUENCE: 67
ccaggacgag tagtcggcgg gccaggacga gtagtcggcg gg 42

<210> SEQ ID NO 68
<211> LENGTH: 1828
<212> TYPE: DNA
<213> ORGANISM: E. coli

<400> SEQUENCE: 68
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgaaatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgccc aggacgagta 900
gtcggcgggc caggacgagt agtcggcggg tgtatggatc ctgagcccat agtgcgtatc 960
gtaggtcgaa atggtctatg tgttgatgtt agggatggaa gattccacaa cggaaacgca 1020

-continued

```
atacagttgt ggccatgcaa gtctaataca gatgcaaatc agctctggac tttgaaaaga   1080

gacaatacta ttcgatctaa tggaaagtgt ttaactactt acgggtacag tccgggagtc   1140

tatgtgatga tctatgattg caatactgct gcaactgatg ccacccgctg gcaaatatgg   1200

gataatggaa ccatcataaa tcccagatct agtctagttt tagcagcgac atcagggaac   1260

agtggtacca cacttacagt gcaaaccaac atttatgccg ttagtcaagg ttggcttcct   1320

actaataata cacaaccttt tgttacaacc attgttgggc tatatggtct gtgcttgcaa   1380

gcaaatagtg gacaagtatg gatagaggac tgtagcagtg aaaaggctga acaacagtgg   1440

gctctttatg cagatggttc aatacgtcct cagcaaaacc gagataattg ccttacaagt   1500

gattctaata tacgggaaac agttgttaag atcctctctt gtggccctgc atcctctggc   1560

caacgatgga tgttcaagaa tgatggaacc attttaaatt tgtatagtgg gttggtgtta   1620

gatgtgaggc gatcggatcc gagccttaaa caaatcattc tttaccctct ccatggtgac   1680

ccaaaccaaa tatggttacc attattttga tagacagatt actctcttgc agtgtgtgtg   1740

tcctgccatg aaaatagatg gcttaaataa aaaggacatt gtaaattttg taactgaaag   1800

gacagcaagt tatatcgaat tcctgcag                                      1828
```

```
<210> SEQ ID NO 69
<211> LENGTH: 29
<212> TYPE: PRT
<213> ORGANISM: E. coli

<400> SEQUENCE: 69

Cys Ala Pro Pro Pro Ser Ser Gln Phe Ser Leu Leu Ile Arg Pro Val
1               5                   10                  15

Val Pro Asn Phe Asn Ala Asp Val Cys Met Asp Pro Glu
            20                  25


<210> SEQ ID NO 70
<211> LENGTH: 20
<212> TYPE: PRT
<213> ORGANISM: E. coli

<400> SEQUENCE: 70

Cys Pro Gly Arg Val Val Gly Gly Pro Gly Arg Val Val Gly Gly Cys
1               5                   10                  15

Met Asp Pro Glu
            20


<210> SEQ ID NO 71
<211> LENGTH: 51
<212> TYPE: DNA
<213> ORGANISM: E. coli

<400> SEQUENCE: 71

attgcagggc agggaggggg tagtagcggc gggggatgta tggatcctga g             51


<210> SEQ ID NO 72
<211> LENGTH: 105
<212> TYPE: DNA
<213> ORGANISM: E. coli

<400> SEQUENCE: 72

ctcatggtgt atagatgcgc acctccacca tcgtcacagt ttctttgct tataaggcca     60

gtggtaccaa attttaatgc tgatgtttgt atggatcctg agccc                   105
```

-continued

<210> SEQ ID NO 73
<211> LENGTH: 48
<212> TYPE: DNA
<213> ORGANISM: E. coli

<400> SEQUENCE: 73
taccacatat ctacgcctcc gccctgaggt ccgcccccag gcgttcct 48

<210> SEQ ID NO 74
<211> LENGTH: 69
<212> TYPE: DNA
<213> ORGANISM: E. coli

<400> SEQUENCE: 74
ggaggcgggg actccagcgg gggtccgcaa ggaattgcag ggcagggagg gggtagtagc 60
ggcggggga 69

<210> SEQ ID NO 75
<211> LENGTH: 1855
<212> TYPE: DNA
<213> ORGANISM: E. coli

<400> SEQUENCE: 75
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgaaatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgg aggcgggggt 900
ggaggcgggg gtccgcaagg aattgcaggg cagggagggg gtagtagcgg cgggggatgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aaccttttgt tacaaccatt 1380
gttgggctat atggtctgtg cttgcaagca aatagtggac aagtatggat agaggactgt 1440
agcagtgaaa aggctgaaca acagtgggct ctttatgcag atggttcaat acgtcctcag 1500

-continued caaaaccgag ataattgcct tacaagtgat tctaatatac gggaaacagt tgttaagatc 1560
ctctcttgtg gccctgcatc ctctggccaa cgatggatgt tcaagaatga tggaaccatt 1620
ttaaatttgt atagtgggtt ggtgttagat gtgaggcgat cggatccgag ccttaaacaa 1680
atcattcttt accctctcca tggtgaccca aaccaaatat ggttaccatt attttgatag 1740
acagattact ctcttgcagt gtgtgtgtcc tgccatgaaa atagatggct taaataaaaa 1800
ggacattgta aattttgtaa ctgaaaggac agcaagttat atcgaattcc tgcag 1855

<210> SEQ ID NO 76
<211> LENGTH: 29
<212> TYPE: PRT
<213> ORGANISM: E. coli

<400> SEQUENCE: 76

Cys Ala Pro Pro Pro Ser Ser Gln Phe Ser Leu Leu Ile Arg Pro Val
1 5 10 15

Val Pro Asn Phe Asn Ala Asp Val Cys Met Asp Pro Glu
20 25

<210> SEQ ID NO 77
<211> LENGTH: 29
<212> TYPE: PRT
<213> ORGANISM: E. coli

<400> SEQUENCE: 77

Cys Gly Gly Gly Ser Ser Gly Gly Gly Pro Gln Gly Ile Ala Gly Gln
1 5 10 15

Gly Gly Gly Ser Ser Gly Gly Gly Cys Met Asp Pro Glu
20 25

<210> SEQ ID NO 78
<211> LENGTH: 39
<212> TYPE: DNA
<213> ORGANISM: E. coli

<400> SEQUENCE: 78
attgcagggc aggatgaaga ggatgctgat gtttgtatg 39

<210> SEQ ID NO 79
<211> LENGTH: 105
<212> TYPE: DNA
<213> ORGANISM: E. coli

<400> SEQUENCE: 79
ctcatggtgt atagatgcgc acctccacca tcgtcacagt tttctttgct tataaggcca 60
gtggtaccaa attttaatgc tgatgtttgt atggatcctg agccc 105

<210> SEQ ID NO 80
<211> LENGTH: 33
<212> TYPE: DNA
<213> ORGANISM: E. coli

<400> SEQUENCE: 80
ggaggtggta gcagtcctcc aagaggcgtt cct 33

<210> SEQ ID NO 81
<211> LENGTH: 69
<212> TYPE: DNA
<213> ORGANISM: E. coli

-continued

<400> SEQUENCE: 81
gcacctccac catcgtcagg aggttctccg caaggaattg cagggcagga tgaagaggat 60
gctgatgtt 69

<210> SEQ ID NO 82
<211> LENGTH: 1855
<212> TYPE: DNA
<213> ORGANISM: E. coli

<400> SEQUENCE: 82
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgaaatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgc acctccacca 900
tcgtcggagg ttctccgcaa ggaattgcag ggcaggatga agaggaatgc tgatgtttgt 960
atggatcctg agcccatagt gcgtatcgta ggtcgaaatg gtctatgtgt tgatgttagg 1020
gatggaagat tccacaacgg aaacgcaata cagttgtggc catgcaagtc taatacagat 1080
gcaaatcagc tctggacttt gaaaagagac aatactattc gatctaatgg aaagtgttta 1140
actacttacg ggtacagtcc gggagtctat gtgatgatct atgattgcaa tactgctgca 1200
actgatgcca cccgctggca aatatgggat aatggaacca tcataaatcc cagatctagt 1260
ctagttttag cagcgacatc agggaacagt ggtaccacac ttacagtgca aaccaacatt 1320
tatgccgtta gtcaaggttg gcttcctact aataatacac aacctttttgt tacaaccatt 1380 gttgggctat atggtctgtg cttgcaagca aatagtggac aagtatggat agaggactgt 1440
agcagtgaaa aggctgaaca acagtgggct ctttatgcag atggttcaat acgtcctcag 1500
caaaaccgag ataattgcct tacaagtgat tctaatatac gggaaacagt tgttaagatc 1560
ctctcttgtg gccctgcatc ctctggccaa cgatggatgt tcaagaatga tggaaccatt 1620
ttaaatttgt atagtgggtt ggtgttagat gtgaggcgat cggatccgag ccttaaacaa 1680
atcattcttt accctctcca tggtgaccca aaccaaatat ggttaccatt attttgatag 1740
acagattact ctcttgcagt gtgtgtgtcc tgccatgaaa atagatggct taaataaaaa 1800
ggacattgta aattttgtaa ctgaaaggac agcaagttat atcgaattcc tgcag 1855

<210> SEQ ID NO 83
<211> LENGTH: 29

-continued

<212> TYPE: PRT
<213> ORGANISM: E. coli

<400> SEQUENCE: 83

Cys Ala Pro Pro Pro Ser Ser Gln Phe Ser Leu Leu Ile Arg Pro Val
1 5 10 15

Val Pro Asn Phe Asn Ala Asp Val Cys Met Asp Pro Glu
20 25

<210> SEQ ID NO 84
<211> LENGTH: 29
<212> TYPE: PRT
<213> ORGANISM: E. coli

<400> SEQUENCE: 84

Cys Ala Pro Pro Pro Ser Ser Gly Gly Ser Pro Gln Gly Ile Ala Gly
1 5 10 15

Gln Asp Glu Glu Asp Ala Asp Val Cys Met Asp Pro Glu
20 25

<210> SEQ ID NO 85
<211> LENGTH: 36
<212> TYPE: DNA
<213> ORGANISM: E. coli

<400> SEQUENCE: 85
gtagtcggcg ggggggagg ctgtatggat cctgag 36

<210> SEQ ID NO 86
<211> LENGTH: 105
<212> TYPE: DNA
<213> ORGANISM: E. coli

<400> SEQUENCE: 86
ctcatggtgt atagatgcgc acctccacca tcgtcacagt tttctttgct tataaggcca 60
gtggtaccaa attttaatgc tgatgtttgt atggatcctg agccc 105

<210> SEQ ID NO 87
<211> LENGTH: 33
<212> TYPE: DNA
<213> ORGANISM: E. coli

<400> SEQUENCE: 87
taccacatat ctacgcctcc gcctggtcct gct 33

<210> SEQ ID NO 88
<211> LENGTH: 39
<212> TYPE: DNA
<213> ORGANISM: E. coli

<400> SEQUENCE: 88
ggaggcggac caggacgagt agtcggcggg gggggaggc 39

<210> SEQ ID NO 89
<211> LENGTH: 1825
<212> TYPE: DNA
<213> ORGANISM: E. coli

<400> SEQUENCE: 89
gaattcatga aaccgggagg aaatactatt gtaatatgga tgtatgcagt ggcaacatgg 60
ctttgttttg gatccacctc agggtggtct ttcacattag aggataacaa catattcccc 120

-continued

```
aaacaatacc caattataaa ctttaccaca gcgggtgcca ctgtgcaaag ctacacaaac    180

tttatcagag ctgttcgcgg tcgtttaaca actggagctg atgtgagaca tgaaatacca    240

gtgttgccaa acagagttgg tttgcctata aaccaacggt ttattttagt tgaactctca    300

aatcatgcag agctttctgt tacattagcg ctggatgtca ccaatgcata tgtggtcggc    360

taccgtgctg gaaatagcgc atatttcttt catcctgaca atcaggaaga tgcagaagca    420

atcactcatc ttttcactga tgttcaaaat cgatatacat tcgcctttgg tggtaattat    480

gatagacttg aacaacttgc tggtaatctg agagaaaata tcgagttggg aaatggtcca    540

ctagaggagg ctatctcagc gctttattat tacagtactg gtggcactca gcttccaact    600

ctggctcgtt cctttataat ttgcatccaa atgatttcag aagcagcaag attccaatat    660

attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840

gatgtgagta tattaatccc tatcatagct ctcatggtgt atagatgcgg aggcggacca    900

ggacgagtag tcggcggggg gggaggctgt atggatcctg agcccatagt gcgtatcgta    960

ggtcgaaatg gtctatgtgt tgatgttagg gatggaagat tccacaacgg aaacgcaata   1020

cagttgtggc catgcaagtc taatacagat gcaaatcagc tctggacttt gaaaagagac   1080

aatactattc gatctaatgg aaagtgttta actacttacg ggtacagtcc gggagtctat   1140

gtgatgatct atgattgcaa tactgctgca actgatgcca cccgctggca aatatgggat   1200

aatggaacca tcataaatcc cagatctagt ctagttttag cagcgacatc agggaacagt   1260

ggtaccacac ttacagtgca aaccaacatt tatgccgtta gtcaaggttg gcttcctact   1320

aataatacac aacctttgt tacaaccatt gttgggctat atggtctgtg cttgcaagca   1380

aatagtggac aagtatggat agaggactgt agcagtgaaa aggctgaaca acagtgggct   1440

ctttatgcag atggttcaat acgtcctcag caaaaccgag ataattgcct tacaagtgat   1500

tctaatatac gggaaacagt tgttaagatc ctctcttgtg gccctgcatc ctctggccaa   1560

cgatggatgt tcaagaatga tggaaccatt ttaaatttgt atagtgggtt ggtgttagat   1620

gtgaggcgat cggatccgag ccttaaacaa atcattcttt accctctcca tggtgaccca   1680

aaccaaatat ggttaccatt attttgatag acagattact ctcttgcagt gtgtgtgtcc   1740

tgccatgaaa atagatggct taaataaaaa ggacattgta aattttgtaa ctgaaaggac   1800

agcaagttat atcgaattcc tgcag                                         1825
```

<210> SEQ ID NO 90
<211> LENGTH: 29
<212> TYPE: PRT
<213> ORGANISM: E. coli

<400> SEQUENCE: 90

```
Cys Ala Pro Pro Pro Ser Ser Gln Phe Ser Leu Leu Ile Arg Pro Val
1               5                   10                  15

Val Pro Asn Phe Asn Ala Asp Val Cys Met Asp Pro Glu
            20                  25
```

<210> SEQ ID NO 91
<211> LENGTH: 19
<212> TYPE: PRT
<213> ORGANISM: E. coli

<400> SEQUENCE: 91

-continued

Cys Gly Gly Gly Pro Gly Arg Val Val Gly Gly Gly Gly Gly Cys Met
1 5 10 15

Asp Pro Glu

<210> SEQ ID NO 92
<211> LENGTH: 33
<212> TYPE: DNA
<213> ORGANISM: E. coli

<400> SEQUENCE: 92
gtagtcggcg ggggaggctg tatggatcct gag 33

<210> SEQ ID NO 93
<211> LENGTH: 105
<212> TYPE: DNA
<213> ORGANISM: E. coli

<400> SEQUENCE: 93
ctcatggtgt atagatgcgc acctccacca tcgtcacagt tttctttgct tataaggcca 60
gtggtaccaa attttaatgc tgatgtttgt atggatcctg agccc 105

<210> SEQ ID NO 94
<211> LENGTH: 30
<212> TYPE: DNA
<213> ORGANISM: E. coli

<400> SEQUENCE: 94
taccacatat ctacgcctcc gggtcctgct 30

<210> SEQ ID NO 95
<211> LENGTH: 33
<212> TYPE: DNA
<213> ORGANISM: E. coli

<400> SEQUENCE: 95
ggaggcccag gacgagtagt cggcggggga ggc 33

<210> SEQ ID NO 96
<211> LENGTH: 1819
<212> TYPE: DNA
<213> ORGANISM: E. coli

<400> SEQUENCE: 96
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgaaatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720

-continued

```
gtaattacac ttgagaatag ttgggggaga ctttccactg caattcaaga gtctaaccaa    780

ggagcctttg ctagtccaat tcaactgcaa agacgtaatg gttccaaatt cagtgtgtac    840

gatgtgagta tattaatccc tatcatagct ctcatggtgt atagatgcgg aggcccagga    900

cgagtagtcg gcgggggagg ctgtatggat cctgagccca tagtgcgtat cgtaggtcga    960

aatggtctat gtgttgatgt tagggatgga agattccaca acggaaacgc aatacagttg   1020

tggccatgca agtctaatac agatgcaaat cagctctgga ctttgaaaag agacaatact   1080

attcgatcta atggaaagtg tttaactact tacgggtaca gtccgggagt ctatgtgatg   1140

atctatgatt gcaatactgc tgcaactgat gccacccgct ggcaaatatg ggataatgga   1200

accatcataa atcccagatc tagtctagtt ttagcagcga catcagggaa cagtggtacc   1260

acacttacag tgcaaaccaa catttatgcc gttagtcaag gttggcttcc tactaataat   1320

acacaacctt ttgttacaac cattgttggg ctatatggtc tgtgcttgca agcaaatagt   1380

ggacaagtat ggatagagga ctgtagcagt gaaaaggctg aacaacagtg ggctctttat   1440

gcagatggtt caatacgtcc tcagcaaaac cgagataatt gccttacaag tgattctaat   1500

atacgggaaa cagttgttaa gatcctctct tgtggccctg catcctctgg ccaacgatgg   1560

atgttcaaga atgatggaac cattttaaat ttgtatagtg ggttggtgtt agatgtgagg   1620

cgatcggatc cgagccttaa acaaatcatt ctttaccctc tccatggtga cccaaaccaa   1680

atatggttac cattattttg atagacagat tactctcttg cagtgtgtgt gtcctgccat   1740

gaaaatagat ggcttaaata aaaaggacat tgtaaatttt gtaactgaaa ggacagcaag   1800

ttatatcgaa ttcctgcag                                                1819
```

<210> SEQ ID NO 97
<211> LENGTH: 29
<212> TYPE: PRT
<213> ORGANISM: E. coli

<400> SEQUENCE: 97

```
Cys Ala Pro Pro Pro Ser Ser Gln Phe Ser Leu Leu Ile Arg Pro Val
1               5                   10                  15

Val Pro Asn Phe Asn Ala Asp Val Cys Met Asp Pro Glu
            20                  25
```

<210> SEQ ID NO 98
<211> LENGTH: 17
<212> TYPE: PRT
<213> ORGANISM: E. coli

<400> SEQUENCE: 98

```
Cys Gly Gly Pro Gly Arg Val Val Gly Gly Gly Gly Cys Met Asp Pro
1               5                   10                  15

Glu
```

<210> SEQ ID NO 99
<211> LENGTH: 30
<212> TYPE: DNA
<213> ORGANISM: E. coli

<400> SEQUENCE: 99

```
gtagtcggcg ggggctgtat ggatcctgag                                      30
```

<210> SEQ ID NO 100
<211> LENGTH: 105

-continued

<212> TYPE: DNA
<213> ORGANISM: E. coli

<400> SEQUENCE: 100
ctcatggtgt atagatgcgc acctccacca tcgtcacagt tttctttgct tataaggcca 60
gtggtaccaa attttaatgc tgatgtttgt atggatcctg agccc 105

<210> SEQ ID NO 101
<211> LENGTH: 27
<212> TYPE: DNA
<213> ORGANISM: E. coli

<400> SEQUENCE: 101
taccacatat ctacgcctgg tcctgct 27

<210> SEQ ID NO 102
<211> LENGTH: 27
<212> TYPE: DNA
<213> ORGANISM: E. coli

<400> SEQUENCE: 102
ggaccaggac gagtagtcgg cgggggc 27

<210> SEQ ID NO 103
<211> LENGTH: 1813
<212> TYPE: DNA
<213> ORGANISM: E. coli

<400> SEQUENCE: 103
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgaaatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgg accaggacga 900
gtagtcggcg ggggctgtat ggatcctgag cccatagtgc gtatcgtagg tcgaaatggt 960
ctatgtgttg atgttaggga tggaagattc cacaacggaa acgcaataca gttgtggcca 1020
tgcaagtcta atacagatgc aaatcagctc tggactttga aaagagacaa tactattcga 1080
tctaatggaa agtgtttaac tacttacggg tacagtccgg gagtctatgt gatgatctat 1140
gattgcaata ctgctgcaac tgatgccacc cgctggcaaa tatgggataa tggaaccatc 1200
ataaatccca gatctagtct agttttagca gcgacatcag ggaacagtgg taccacactt 1260

-continued acagtgcaaa ccaacattta tgccgttagt caaggttggc ttcctactaa taatacacaa 1320
ccttttgtta caaccattgt tgggctatat ggtctgtgct tgcaagcaaa tagtggacaa 1380
gtatggatag aggactgtag cagtgaaaag gctgaacaac agtgggctct ttatgcagat 1440
ggttcaatac gtcctcagca aaaccgagat aattgcctta caagtgattc taatatacgg 1500
gaaacagttg ttaagatcct ctcttgtggc cctgcatcct ctggccaacg atggatgttc 1560
aagaatgatg gaaccatttt aaatttgtat agtgggttgg tgttagatgt gaggcgatcg 1620
gatccgagcc ttaaacaaat cattctttac cctctccatg gtgacccaaa ccaaatatgg 1680
ttaccattat tttgatagac agattactct cttgcagtgt gtgtgtcctg ccatgaaaat 1740
agatggctta aataaaaagg acattgtaaa ttttgtaact gaaaggacag caagttatat 1800
cgaattcctg cag 1813

<210> SEQ ID NO 104
<211> LENGTH: 29
<212> TYPE: PRT
<213> ORGANISM: E. coli

<400> SEQUENCE: 104

Cys Ala Pro Pro Pro Ser Ser Gln Phe Ser Leu Leu Ile Arg Pro Val
1 5 10 15

Val Pro Asn Phe Asn Ala Asp Val Cys Met Asp Pro Glu
20 25

<210> SEQ ID NO 105
<211> LENGTH: 15
<212> TYPE: PRT
<213> ORGANISM: E. coli

<400> SEQUENCE: 105

Cys Gly Pro Gly Arg Val Val Gly Gly Gly Cys Met Asp Pro Glu
1 5 10 15

<210> SEQ ID NO 106
<211> LENGTH: 48
<212> TYPE: DNA
<213> ORGANISM: E. coli

<400> SEQUENCE: 106
attgcagggc agggggtag tagcggcggg ggatgtatgg atcctgag 48

<210> SEQ ID NO 107
<211> LENGTH: 105
<212> TYPE: DNA
<213> ORGANISM: E. coli

<400> SEQUENCE: 107
ctcatggtgt atagatgcgc acctccacca tcgtcacagt tttctttgct tataaggcca 60
gtggtaccaa attttaatgc tgatgtttgt atggatcctg agccc 105

<210> SEQ ID NO 108
<211> LENGTH: 45
<212> TYPE: DNA
<213> ORGANISM: E. coli

<400> SEQUENCE: 108
taccacatat ctacgcctcc gccctgaggt cccccaggcg ttcct 45

<210> SEQ ID NO 109

-continued

<211> LENGTH: 63
<212> TYPE: DNA
<213> ORGANISM: E. coli

<400> SEQUENCE: 109
ggaggcggga ctccaggggg tccgcaagga attgcagggc agggggtag tagcggcggg 60 gga 63

<210> SEQ ID NO 110
<211> LENGTH: 1849
<212> TYPE: DNA
<213> ORGANISM: E. coli

<400> SEQUENCE: 110
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgaaatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540
ctagaggagg ctatctcagc gctttattat tacagtactg gtggcactca gcttccaact 600
ctggctcgtt cctttataat ttgcatccaa atgatttcag aagcagcaag attccaatat 660
attgagggag aaatgcgcac gagaattagg tacaaccgga gatctgcacc agatcctagc 720
gtaattacac ttgagaatag ttgggggaga ctttccactg caattcaaga gtctaaccaa 780
ggagcctttg ctagtccaat tcaactgcaa agacgtaatg gttccaaatt cagtgtgtac 840
gatgtgagta tattaatccc tatcatagct ctcatggtgt atagatgcgg aggcgggact 900
ccagggggtc cgcaaggaat tgcagggcag gggggtagta gcggcggggg atgtatggat 960
cctgagccca tagtgcgtat cgtaggtcga aatggtctat gtgttgatgt tagggatgga 1020
agattccaca acggaaacgc aatacagttg tggccatgca agtctaatac agatgcaaat 1080
cagctctgga ctttgaaaag agacaatact attcgatcta atggaaagtg tttaactact 1140
tacgggtaca gtccgggagt ctatgtgatg atctatgatt gcaatactgc tgcaactgat 1200
gccacccgct ggcaaatatg ggataatgga accatcataa atcccagatc tagtctagtt 1260
ttagcagcga catcagggaa cagtggtacc acacttacag tgcaaaccaa catttatgcc 1320
gttagtcaag gttggcttcc tactaataat acacaacctt ttgttacaac cattgttggg 1380
ctatatggtc tgtgcttgca agcaaatagt ggacaagtat ggatagagga ctgtagcagt 1440
gaaaaggctg aacaacagtg ggctctttat gcagatggtt caatacgtcc tcagcaaaac 1500
cgagataatt gccttacaag tgattctaat atacgggaaa cagttgttaa gatcctctct 1560
tgtggccctg catcctctgg ccaacgatgg atgttcaaga atgatggaac cattttaaat 1620
ttgtatagtg ggttggtgtt agatgtgagg cgatcggatc cgagccttaa acaaatcatt 1680
ctttaccctc tccatggtga cccaaaccaa atatggttac cattattttg atagacagat 1740
tactctcttg cagtgtgtgt gtcctgccat gaaaatagat ggcttaaata aaaaggacat 1800
tgtaaatttt gtaactgaaa ggacagcaag ttatatcgaa ttcctgcag 1849

-continued

<210> SEQ ID NO 111
<211> LENGTH: 29
<212> TYPE: PRT
<213> ORGANISM: E. coli

<400> SEQUENCE: 111

Cys Ala Pro Pro Pro Ser Ser Gln Phe Ser Leu Leu Ile Arg Pro Val
1 5 10 15

Val Pro Asn Phe Asn Ala Asp Val Cys Met Asp Pro Glu
20 25

<210> SEQ ID NO 112
<211> LENGTH: 27
<212> TYPE: PRT
<213> ORGANISM: E. coli

<400> SEQUENCE: 112

Cys Gly Gly Gly Ser Ser Gly Gly Pro Gln Gly Ile Ala Gly Gln Gly
1 5 10 15

Gly Ser Ser Gly Gly Gly Cys Met Asp Pro Glu
20 25

<210> SEQ ID NO 113
<211> LENGTH: 45
<212> TYPE: DNA
<213> ORGANISM: E. coli

<400> SEQUENCE: 113
attgcagggc agggtagtag cggcggggga tgtatggatc ctgag 45

<210> SEQ ID NO 114
<211> LENGTH: 105
<212> TYPE: DNA
<213> ORGANISM: E. coli

<400> SEQUENCE: 114
ctcatggtgt atagatgcgc acctccacca tcgtcacagt tttctttgct tataaggcca 60
gtggtaccaa attttaatgc tgatgtttgt atggatcctg agccc 105

<210> SEQ ID NO 115
<211> LENGTH: 42
<212> TYPE: DNA
<213> ORGANISM: E. coli

<400> SEQUENCE: 115
taccacatat ctacgcctcc gccctgaggt ccaggcgttc ct 42

<210> SEQ ID NO 116
<211> LENGTH: 57
<212> TYPE: DNA
<213> ORGANISM: E. coli

<400> SEQUENCE: 116
ggaggcggga ctccaggtcc gcaaggaatt gcagggcagg gtagtagcgg cgggggga 57

<210> SEQ ID NO 117
<211> LENGTH: 1843
<212> TYPE: DNA
<213> ORGANISM: E. coli

<400> SEQUENCE: 117

-continued

```
gaattcatga aaccgggagg aaatactatt gtaatatgga tgtatgcagt ggcaacatgg     60
ctttgttttg gatccacctc agggtggtct ttcacattag aggataacaa catattcccc    120
aaacaatacc caattataaa ctttaccaca gcgggtgcca ctgtgcaaag ctacacaaac    180
tttatcagag ctgttcgcgg tcgtttaaca actggagctg atgtgagaca tgaaatacca    240
gtgttgccaa acagagttgg tttgcctata aaccaacggt ttattttagt tgaactctca    300
aatcatgcag agctttctgt tacattagcg ctggatgtca ccaatgcata tgtggtcggc    360
taccgtgctg gaaatagcgc atatttcttt catcctgaca atcaggaaga tgcagaagca    420
atcactcatc ttttcactga tgttcaaaat cgatatacat tcgcctttgg tggtaattat    480
gatagacttg aacaacttgc tggtaatctg agagaaaata tcgagttggg aaatggtcca    540
ctagaggagg ctatctcagc gctttattat tacagtactg gtggcactca gcttccaact    600
ctggctcgtt cctttataat ttgcatccaa atgatttcag aagcagcaag attccaatat    660
attgagggag aaatgcgcac gagaattagg tacaaccgga gatctgcacc agatcctagc    720
gtaattacac ttgagaatag ttgggggaga ctttccactg caattcaaga gtctaaccaa    780
ggagcctttg ctagtccaat tcaactgcaa agacgtaatg gttccaaatt cagtgtgtac    840
gatgtgagta tattaatccc tatcatagct ctcatggtgt atagatgcgg aggcgggact    900
ccaggtccgc aaggaattgc agggcagggt agtagcggcg ggggatgtat ggatcctgag    960
cccatagtgc gtatcgtagg tcgaaatggt ctatgtgttg atgttaggga tggaagattc   1020
cacaacggaa acgcaataca gttgtggcca tgcaagtcta atacagatgc aaatcagctc   1080
tggactttga aaagagacaa tactattcga tctaatggaa agtgtttaac tacttacggg   1140
tacagtccgg gagtctatgt gatgatctat gattgcaata ctgctgcaac tgatgccacc   1200
cgctggcaaa tatgggataa tggaaccatc ataaatccca gatctagtct agttttagca   1260
gcgacatcag ggaacagtgg taccacactt acagtgcaaa ccaacattta tgccgttagt   1320
caaggttggc ttcctactaa taatacacaa ccttttgtta caaccattgt tgggctatat   1380
ggtctgtgct tgcaagcaaa tagtggacaa gtatggatag aggactgtag cagtgaaaag   1440
gctgaacaac agtgggctct ttatgcagat ggttcaatac gtcctcagca aaaccgagat   1500
aattgcctta caagtgattc taatatacgg gaaacagttg ttaagatcct ctcttgtggc   1560
cctgcatcct ctggccaacg atggatgttc aagaatgatg gaaccatttt aaatttgtat   1620
agtgggttgg tgttagatgt gaggcgatcg gatccgagcc ttaaacaaat cattctttac   1680
cctctccatg gtgacccaaa ccaaatatgg ttaccattat tttgatagac agattactct   1740
cttgcagtgt gtgtgtcctg ccatgaaaat agatggctta aataaaaagg acattgtaaa   1800
ttttgtaact gaaaggacag caagttatat cgaattcctg cag                      1843
```

<210> SEQ ID NO 118
<211> LENGTH: 29
<212> TYPE: PRT
<213> ORGANISM: E. coli

<400> SEQUENCE: 118

```
Cys Ala Pro Pro Pro Ser Ser Gln Phe Ser Leu Leu Ile Arg Pro Val
1               5                   10                  15

Val Pro Asn Phe Asn Ala Asp Val Cys Met Asp Pro Glu
            20                  25
```

<210> SEQ ID NO 119
<211> LENGTH: 25

-continued

<212> TYPE: PRT
<213> ORGANISM: E. coli

<400> SEQUENCE: 119

Cys Gly Gly Gly Ser Ser Gly Pro Gln Gly Ile Ala Gly Gln Gly Ser
1 5 10 15

Ser Gly Gly Gly Cys Met Asp Pro Glu
20 25

<210> SEQ ID NO 120
<211> LENGTH: 42
<212> TYPE: DNA
<213> ORGANISM: E. coli

<400> SEQUENCE: 120
attgcagggc agagtagcgg cgggggatgt atggatcctg ag 42

<210> SEQ ID NO 121
<211> LENGTH: 105
<212> TYPE: DNA
<213> ORGANISM: E. coli

<400> SEQUENCE: 121
ctcatggtgt atagatgcgc acctccacca tcgtcacagt tttctttgct tataaggcca 60
gtggtaccaa attttaatgc tgatgtttgt atggatcctg agccc 105

<210> SEQ ID NO 122
<211> LENGTH: 39
<212> TYPE: DNA
<213> ORGANISM: E. coli

<400> SEQUENCE: 122
taccacatat ctacgcctcc gccctgaggt ggcgttcct 39

<210> SEQ ID NO 123
<211> LENGTH: 51
<212> TYPE: DNA
<213> ORGANISM: E. coli

<400> SEQUENCE: 123
ggaggcggga ctccaccgca aggaattgca gggcagagta gcggcggggg a 51

<210> SEQ ID NO 124
<211> LENGTH: 1837
<212> TYPE: DNA
<213> ORGANISM: E. coli

<400> SEQUENCE: 124
gaattcatga aaccgggagg aaatactatt gtaatatgga tgtatgcagt ggcaacatgg 60
ctttgttttg gatccacctc agggtggtct ttcacattag aggataacaa catattcccc 120
aaacaatacc caattataaa ctttaccaca gcgggtgcca ctgtgcaaag ctacacaaac 180
tttatcagag ctgttcgcgg tcgtttaaca actggagctg atgtgagaca tgaaatacca 240
gtgttgccaa acagagttgg tttgcctata aaccaacggt ttattttagt tgaactctca 300
aatcatgcag agctttctgt tacattagcg ctggatgtca ccaatgcata tgtggtcggc 360
taccgtgctg gaaatagcgc atatttcttt catcctgaca atcaggaaga tgcagaagca 420
atcactcatc ttttcactga tgttcaaaat cgatatacat tcgcctttgg tggtaattat 480
gatagacttg aacaacttgc tggtaatctg agagaaaata tcgagttggg aaatggtcca 540

-continued

```
ctagaggagg ctatctcagc gctttattat tacagtactg gtggcactca gcttccaact    600

ctggctcgtt cctttataat ttgcatccaa atgatttcag aagcagcaag attccaatat    660

attgagggag aaatgcgcac gagaattagg tacaaccgga gatctgcacc agatcctagc    720

gtaattacac ttgagaatag ttgggggaga ctttccactg caattcaaga gtctaaccaa    780

ggagcctttg ctagtccaat tcaactgcaa agacgtaatg gttccaaatt cagtgtgtac    840

gatgtgagta tattaatccc tatcatagct ctcatggtgt atagatgcgg aggcgggact    900

ccaccgcaag gaattgcagg gcagagtagc ggcgggggat gtatggatcc tgagcccata    960

gtgcgtatcg taggtcgaaa tggtctatgt gttgatgtta gggatggaag attccacaac   1020

ggaaacgcaa tacagttgtg gccatgcaag tctaatacag atgcaaatca gctctggact   1080

ttgaaaagag acaatactat tcgatctaat ggaaagtgtt taactactta cgggtacagt   1140

ccgggagtct atgtgatgat ctatgattgc aatactgctg caactgatgc cacccgctgg   1200

caaatatggg ataatggaac catcataaat cccagatcta gtctagtttt agcagcgaca   1260

tcagggaaca gtggtaccac acttacagtg caaaccaaca tttatgccgt tagtcaaggt   1320

tggcttccta ctaataatac acaacctttt gttacaacca ttgttgggct atatggtctg   1380

tgcttgcaag caaatagtgg acaagtatgg atagaggact gtagcagtga aaaggctgaa   1440

caacagtggg ctctttatgc agatggttca atacgtcctc agcaaaaccg agataattgc   1500

cttacaagtg attctaatat acgggaaaca gttgttaaga tcctctcttg tggccctgca   1560

tcctctggcc aacgatggat gttcaagaat gatggaacca ttttaaattt gtatagtggg   1620

ttggtgttag atgtgaggcg atcggatccg agccttaaac aaatcattct ttaccctctc   1680

catggtgacc caaaccaaat atggttacca ttattttgat agacagatta ctctcttgca   1740

gtgtgtgtgt cctgccatga aaatagatgg cttaaataaa aaggacattg taaattttgt   1800

aactgaaagg acagcaagtt atatcgaatt cctgcag                            1837
```

<210> SEQ ID NO 125
<211> LENGTH: 29
<212> TYPE: PRT
<213> ORGANISM: E. coli

<400> SEQUENCE: 125

```
Cys Ala Pro Pro Pro Ser Ser Gln Phe Ser Leu Leu Ile Arg Pro Val
1               5                   10                  15

Val Pro Asn Phe Asn Ala Asp Val Cys Met Asp Pro Glu
            20                  25
```

<210> SEQ ID NO 126
<211> LENGTH: 23
<212> TYPE: PRT
<213> ORGANISM: E. coli

<400> SEQUENCE: 126

```
Cys Gly Gly Gly Ser Ser Pro Gln Gly Ile Ala Gly Gln Ser Ser Gly
1               5                   10                  15

Gly Gly Cys Met Asp Pro Glu
            20
```

<210> SEQ ID NO 127
<211> LENGTH: 20
<212> TYPE: DNA
<213> ORGANISM: Artificial Sequence
<220> FEATURE:
<223> OTHER INFORMATION: synthetic construct -continued

```
<400> SEQUENCE: 127

ataacttgct gctcctttca                                                  20


<210> SEQ ID NO 128
<211> LENGTH: 23
<212> TYPE: DNA
<213> ORGANISM: Artificial Sequence
<220> FEATURE:
<223> OTHER INFORMATION: synthetic construct

<400> SEQUENCE: 128

ccgggaggaa atactattgt aat                                              23


<210> SEQ ID NO 129
<211> LENGTH: 43
<212> TYPE: DNA
<213> ORGANISM: Artificial Sequence
<220> FEATURE:
<223> OTHER INFORMATION: synthetic construct

<400> SEQUENCE: 129

ggaggaatcc ggagatgaaa ccgggaggaa atactattgt aat                        43


<210> SEQ ID NO 130
<211> LENGTH: 33
<212> TYPE: DNA
<213> ORGANISM: Artificial Sequence
<220> FEATURE:
<223> OTHER INFORMATION: synthetic construct

<400> SEQUENCE: 130

gtaggcgctg cagataactt gctgtccttt cag                                   33
```

RICIN-LIKE TOXINS FOR TREATMENT OF CANCER

This application is a 371 of PCT/CA00/01162, filed Oct. 4, 2000, and claims benefit of U.S. Provisional Application 60/197,409, filed Apr. 14, 2000 and U.S. Provisional Application 60/157,807, filed Oct. 4, 1999.

FIELD OF THE INVENTION

The invention relates to proteins useful as therapeutics against unhealthy cells such as those which occur in inflammation and cancer. The proteins contain A and B chains of a ricin-like toxin linked by a novel linker sequence that is specifically cleaved and activated by proteases specific to cancer.

BACKGROUND OF THE INVENTION

Bacteria and plants are known to produce cytotoxic proteins which may consist of one, two or several polypeptides or subunits. Those proteins having a single subunit may be loosely classified as Type I proteins. Many of the cytotoxins which have evolved two subunit structures are referred to as type 11 proteins (Saelinger, C. B. in Trafficking of Bacterial Toxins (eds. Saelinger, C. B.) 1–13 (CRC Press Inc., Boca Raton, Fla., 1990). One subunit, the A chain, possesses the toxic activity whereas the second subunit, the B chain, binds cell surfaces and mediates entry of the toxin into a target cell. A subset of these toxins kill target cells by inhibiting protein biosynthesis. For example, bacterial toxins such as diphtheria toxin or *Pseudomonas* exotoxin inhibit protein synthesis by inactivating elongation factor 2. Plant toxins such as ricin, abrin, and bacterial toxin Shiga toxin, inhibit protein synthesis by directly inactivating the ribosomes (Olsnes, S. & Phil, A. in Molecular action of toxins and viruses (eds. Cohen, P. & vanHeyningen, S.) 51–105 Elsevier Biomedical Press, Amsterdam, 1982).

Ricin, derived from the seeds of *Ricinus communis* (castor oil plant), may be the most potent of the plant toxins. It is estimated that a single ricin A chain is able to inactivate ribosomes at a rate of 1500 ribosomes/minute. Consequently, a single molecule of ricin is enough to kill a cell (Olsnes, S. & Phil, A. in Molecular action of toxins and viruses (eds. Cohen, P. & vanHeyningen, S.) (Elsevier Biomedical Press, Amsterdam, 1982). The ricin toxin is a glycosylated heterodimer consisting of A and B chains with molecular masses of 30,625 Da and 31,431 Da linked by a disulphide bond. The A chain of ricin has an N-glycosidase activity and catalyzes the excision of a specific adenine residue from the 28S rRNA of eukaryotic ribosomes (Endo, Y. & Tsurugi, K. J., *Biol. Chem.* 262:8128 (1987)). The B chain of ricin, although not toxic in itself, promotes the toxicity of the A chain by binding to galactose residues on the surface of eukaryotic cells and stimulating receptor-mediated endocytosis of the toxin molecule (Simmons et al., Biol. Chem. 261:7912 (1986)). Once the toxin molecule consisting of the A and B chains is internalized into the cell via clathrin-dependent or independent mechanisms, the greater reduction potential within the cell induces a release of the active A chain, eliciting its inhibitory effect on protein synthesis and its cytotoxicity (Emmanuel, F. et al., Anal. *Biochem.* 173: 134–141 (1988); Blum, J. S. et al., *J. Biol. Chem.* 266: 22091–22095 (1991); Fiani, M. L. et al., *Arch. Biochem. Biophys.* 307: 225–230 (1993)). Empirical evidence suggests that activated toxin (e.g. ricin, shiga toxin and others) in the endosomes is transcytosed through the trans-Golgi network to the endoplasmic reticulum by retrograde transport before the A chain is translocated into the cytoplasm to elicit its action (Sandvig, K. & van Deurs, B., FEBS Lett. 346: 99–102 (1994).

Protein toxins are initially produced in an inactive, precursor form. Ricin is initially produced as a single polypeptide (preproricin) with an amino acid N-terminal presequence and 12 amino acid linker between the A and B chains. The pre-sequence is removed during translocation of the ricin precursor into the endoplasmic reticulum (Lord, J. M., *Eur. J. Biochem.* 146:403–409 (1985) and Lord, J. M., *Eur. J. Biochem.* 146:411–416 (1985)). The proricin is then translocated into specialized organelles called protein bodies where a plant protease cleaves the protein at a linker region between the A and B chains (Lord, J. M. et al., *FASAB journal* 8:201–208 (1994)). The two chains, however, remain covalently attached by an interchain disulfide bond (cysteine 259 in the A chain to cysteine 4 in the B chain) and mature disulfide linked ricin is stored in protein bodies inside the plant cells. The A chain is inactive in proricin (O'Hare, M. et al., FEBS Lett. 273:200–204 (1990)) and it is inactive in the disulfide-linked mature ricin (Richardson, P. T. et al., *FEBS Lett.* 255:15–20 (1989)). The ribosomes of the castor bean plant are themselves susceptible to inactivation by ricin A chain; however, as there is no cell surface galactose to permit B chain recognition the A chain cannot re-enter the cell. The exact mechanism of A chain release and activation in target cell cytoplasm is not known (Lord, J. M. et al., *FASAB journal* 8:201–208 (1994)). However, it is known that for activation to take place the disulfide bond between the A and B chains must be reduced and, hence, the linkage between subunits broken.

Diphtheria toxin is produced by *Corynebacterium diphtheriae* as a 535 amino acid polypeptide with a molecular weight of approximately 58 kD (Greenfield, L. et al., *Proc. Natl. Acad. Sci. USA* 80:6853–6857 (1983); Pastan, I. et al., *Annu. Rev. Biochem.* 61:331–354 (1992); Collier, R. J. & Kandel, J., 1. *Biol. Chem.* 246:1496–1503 (1971)). It is secreted as a single-chain polypeptide consisting of 2 functional domains. Similar to proricin, the N-terminal domain (A-chain) contains the cytotoxic moiety whereas the C-terminal domain (B-chain) is responsible for binding to the cells and facilitates toxin endocytosis. Conversely, the mechanism of cytotoxicity for diphtheria toxin is based on ADP-ribosylation of EF-2 thereby blocking protein synthesis and producing cell death. The 2 functional domains in diphtheria toxin are linked by an arginine-rich peptide sequence as well as a disulphide bond. Once the diphtheria toxin is internalized into the cell, the arginine-rich peptide linker is cleaved by trypsin-like enzymes and the disulphide bond (Cys 186–201) is reduced. The cytotoxic domain is subsequently translocated into the cytosol substantially as described above for ricin and elicits ribosomal inhibition and cytotoxicity.

*Pseudomonas* exotoxin is also a 66 kD single-chain toxin protein secreted by *Pseudomonas aeruginosa* with a similar mechanism of cytotoxicity to that of diphtheria toxin (Pastan, I. et al., *Annu. Rev. Biochem.* 61:331–354 (1992); Ogata, M. et al., J. *Biol. Chem.* 267:25396 25401 (1992); Vagil, M. L. et al., *Infect. Immunol.* 16:353–361 (1977)). *Pseudomonas* exotoxin consists of 3 conjoint functional domains. The first domain I (amino acids 1–252) is responsible for cell binding and toxin endocytosis, a second domain II (amino acids 253–364) is responsible for toxin translocation from the endocytic vesicle to the cytosol, and a third domain III (amino acids 400–613) is responsible for protein synthesis inhibition and cytotoxicity. After

*Pseudomonas* exotoxin enters the cell, the liberation of the cytotoxic domain is effected by both proteolytic cleavage of a polypeptide sequence in the second domain (near Arg 279) and the reduction of the disulphide bond (Cys 265–287) in the endocytic vesicles. In essence, the overall pathway to cytotoxicity is analogous to diphtheria toxin with the exception that the toxin translocation domain in *Pseudomonas* exotoxin is structurally distinct.

Class 2 ribosomal inhibitory proteins (RIP-2) constitute other toxins possessing distinct functional domains for cytotoxicity and cell binding/toxin translocation which include abrin, modeccin, volkensin, (Sandvig, K. et al., *Biochem. Soc. Trans.* 21:707–711 (1993)) and mistle toe lectin (viscumin) (Olsnes, S. & Phil, A. in Molecular action of toxins and viruses (eds. Cohen, P. & vanHeyningen, S.) 51–105 Elsevier Biomedical Press, Amsterdam, 1982; Fodstad, et al. Canc. Res. 44: 862 (1984)). Some toxins such as Shiga toxin and cholera toxin also have multiple polypeptide chains responsible for receptor binding and endocytosis.

The ricin gene has been cloned and sequenced, and the X-ray crystal structures of the A and B chains have been described (Rutenber, E. et al. *Proteins* 10:240–250 (1991); Weston et al., *Mol. Bio.* 244:410–422, 1994; Lamb and Lord, *Eur. J. Biochem.* 14:265 (1985); Halling, K. et al. *Nucleic Acids Res.* 13:8019 (1985)). Similarly, the genes for diptheria toxin and *Pseudomonas* exotoxin have been cloned and sequenced, and the 3-dimensional structures of the toxin proteins have been elucidated and described (Columblatti, M. et al., *J. Biol. Chem.* 261:3030–3035 (1986); Allured, V. S. et al., Proc. Natl. Acad. Sci. USA 83:1320–1324 (1986); Gray, G. L. et at., Proc. Natl. Acad. Sci. USA 81:2645–2649 (1984); Greenfield, L. et al., Proc, Natl. Acad. Sci. USA 80:6853–6857 (1983); Collier, R. J. et al., *J. Biol. Chem.* 257:5283–5285 (1982)).

The potential of bacterial and plant toxins for inhibiting mammalian retroviruses, particularly acquired immunodeficiency syndrome (AIDS), has been investigated. Bacterial toxins such as *Pseudomonas* exotoxin and subunit A of diphtheria toxin; dual chain ribosomal inhibitory plant toxins such as ricin, and single chain ribosomal inhibitory proteins such as trichosanthin and pokeweed antiviral protein have been used for the elimination of HIV infected cells (Olson et al., *AIDS Res. and Human Retroviruses* 7:1025–1030 (1991)). The high toxicity of these toxins for mammalian cells, combined with a lack of specificity of action poses a major problem to the development of pharmaceuticals incorporating the toxins, such as immunotoxins.

Due to their extreme toxicity there has been much interest in making ricin-based immunotoxins as therapeutic agents for specifically destroying or inhibiting infected or tumourous cells or tissues (Vitetta et al., *Science* 238:1098–1104 (1987)). An immunotoxin is a conjugate of a specific cell binding component, such as a monoclonal antibody or growth factor and the toxin in which the two protein components are covalently linked. Generally, the components are chemically coupled. However, the linkage may also be a peptide or disulfide bond. The antibody directs the toxin to cell types presenting a specific antigen thereby providing a specificity of action not possible with the natural toxin. Immunotoxins have been made both with the entire ricin molecule (i.e. both chains) and with the ricin A chain alone (Spooner et al., Mol. Immunol. 31:117–125, (1994)).

Immunotoxins made with the ricin dimer (IT-Rs) are more potent toxins than those made with only the A chain (IT-As). The increased toxicity of IT-Rs is thought to be attributed to the dual role of the B chains in binding to the cell surface and in translocating the A chain to the cytosolic compartment of the target cell (Vitetta et al., *Science* 238:1098–1104 (1987); Vitetta & Thorpe, *Seminars in Cell Biology* 2:47–58 (1991)). However, the presence of the B chain in these conjugates also promotes the entry of the immunotoxin into nontarget cells. Even small amounts of B chain may override the specificity of the cell-binding component as the B chain will bind nonspecifically to galactose associated with N-linked carbohydrates, which is present on most cells. IT-As are more specific and safer to use than IT-Rs. However, in the absence of the B chain the A chain has greatly reduced toxicity. Due to the reduced potency of IT-As as compared to IT-Rs, large doses of IT-As must be administered to patients. The large doses frequently cause immune responses and production of neutralizing antibodies in patients (Vitetta et al., *Science* 238:1098–1104 (1987)). IT-As and IT-Rs both suffer from reduced toxicity as the A chain is not released from the conjugate into the target cell cytoplasm.

A number of immunotoxins have been designed to recognize antigens on the surfaces of tumour cells and cells of the immune system (Pastan et al., *Annals New York Academy of Sciences* 758:345–353 (1995)). A major problem with the use of such immunotoxins is that the antibody component is its only targeting mechanism and the target antigen is often found on non-target cells (Vitetta et al., *Immunology Today* 14:252–259 (1993)). Also, the preparation of a suitable specific cell binding component may be problematic. For example, antigens specific for the target cell may not be available and many potential target cells and infective organisms can alter their antigenic make up rapidly to avoid immune recognition. In view of the extreme toxicity of proteins such as ricin, the lack of specificity of the immunotoxins may severely limit their usefulness as therapeutics for the treatment of cancer and infectious diseases.

The insertion of intramolecular protease cleavage sites between the cytotoxic and cell-binding components of a toxin can mimic the way that the natural toxin is activated. European patent application no. 466,222 describes the use of maize-derived pro-proteins which can be converted into active form by cleavage with extracellular blood enzymes such as factor, Xa, thrombin or collagenase. Garred, 0. et al. (J. *Biol. Chem.* 270:10817–10821 (1995)) documented the use of a ubiquitous calcium-dependent serine protease, furin, to activate shiga toxin by cleavage of the trypsin-sensitive linkage between the cytotoxic A-chain and the pentamer of cell-binding B-units. Westby et al. (*Bioconjugate Chem.* 3:375–381 (1992)) documented fusion proteins which have a specific cell binding component and proricin with a protease sensitive cleavage site specific for factor Xa within the linker sequence. O'Hare et al. (*FEBS Lett.* 273:200–204 (1990)) also described a recombinant fusion protein of RTA and staphylococcal protein A joined by a trypsin-sensitive cleavage site. In view of the ubiquitous nature of the extracellular proteases utilized in these approaches, such artificial activation of the toxin precursor or immunotoxin does not confer a mechanism for intracellular toxin activation and the problems of target specificity and adverse immunological reactions to the cell-binding component of the immunotoxin remain.

In a variation of the approach of insertion of intramolecular protease cleavage sites on proteins which combine a binding chain and a toxic chain, Leppla, S. H. et al. (Bacterial Protein Toxins zbl.bakt.suppl. 24:431–442 (1994)) suggest the replacement of the native cleavage site of the protective antigen (PA) produced by *Bacillus anthracis* with a cleavage site that is recognized by cells that contain a particular protease. PA, recognizes, binds, and thereby assists in the internalization of lethal factor (U) and edema toxin (ET), also produced by *Bacillus anthracis*. However, this approach is wholly dependent on the availability of LF, or ET and PA all being localized to cells wherein the modified PA can be activated by the specific protease. It does not confer a mechanism for intracellular toxin activation and presents a problem of ensuring sufficient quantities of toxin for internalization in target cells.

The in vitro activation of a *Staphylococcus*-derived pore forming toxin, (α-hemolysin by extracellular tumour-associated proteases has been documented (Panchel, R. G. et al., *Nature Biotechnology* 14:852–857 (1996)). Artificial activation of α-hemolysin in vitro by said proteases was reported but the actual activity and utility of α-hemolysin in the destruction of target cells were not demonstrated.

α-Hemolysin does not inhibit protein synthesis but is a heptameric transmembrane pore which acts as a channel to allow leakage of molecules up to 3 kD thereby disrupting the ionic balances of the living cell. The α-hemolysin activation domain is likely located on the outside of the target cell (for activation by extracellular proteases). The triggering mechanism in the disclosed hemolysin precursor does not involve the intracellular proteolytic cleavage of 2 functionally distinct domains. Also, the proteases used for the α-hemolysin activation are ubitquitiously secreted extracellular proteases and toxin activation would not be confined to activation in the vicinity of diseased cells. Such widespread activation of the toxin does not confer target specificity and limits the usefulness of said α-hemolysin toxin as therapeutics due to systemic toxicity.

A variety of proteases specifically associated with malignancy have been identified and described. For example, cathepsin is a family of serine, cysteine or aspartic endopeptidases and exopeptidases which has been implicated to play a primary role in cancer metastasis (Schwartz, M. K., Clin. Chim. Acta 237:67–78 (1995); Spiess, E. et al., J. Histochem. Cytochem. 42:917–929 (1-994); Scarborough, P. E. et al., Protein Sci. 2:264276 (1993); Sloane, B. F. et al., Proc. Natl. Acad. Sci. USA 83:2483–2487 (1986); Mikkelsen, T. et al., J. Neurosurge 83:285–290 (1995)). Matrix metalloproteinases (MMPs or matrixins) are zinc-dependent proteinases consisting of collagenases, matrilysin, stromelysins, stromelysin-like MMPs, gelatinases, macrophage elastase, membrane-type MMPs (MT-MMPs) (Krane, S. M., *Ann, N.Y. Acad. Sci.* 732:1–10 (1994); Woessner, J. F., *Ann, N.Y. Acad. Sci.* 732:11–21 (1994); Carvalho, K. et al., *Biochem. Biophys. Res., Comm.* 191:172–179 (1993); Nakano, A. et al. *J. of Neurosurge,* 83:298–307 (1995); Peng, K-W, et al. *Human Gene Therapy,* 8:729–738 (1997); More, D. H. et al. *Gynaecologic oncology,* 65:78–82 (1997), Ravanti, L., Kahari, V. *Intl. J. Mol. Med.* 6(4):391 (2000)). These proteases are involved in pathological matrix remodeling. Under normal physiological conditions, regulation of matrixin activity is effected at the level of gene expression. Enzymatic activity is also controlled stringently by tissue inhibitors of metalloproteinases (TIMPs) (Murphy, G. et al., *Ann. N.Y. Acad. Sci.,* 732:31–41 (1994)). The expression of MMP genes is reported to be activated in inflammatory disorders (e.g. rheumatoid arthritis) and malignancy.

The present inventors have prepared novel recombinant toxic proteins which are specifically toxic to diseased cells but do not depend for their specificity of action on a specific cell binding component. The recombinant proteins toxins have an A chain of a ricin-like toxin linked to a B chain by a synthetic linker sequence which may be cleaved specifically by a protease localised in cells or tissues affected by a specific disease to liberate the toxic A chain thereby selectively inhibiting or destroying the diseased cells or tissues (WO 98/49311 published Nov. 5, 1998 which is incorporated herein by reference).

SUMMARY OF THE INVENTION

The present invention relates to novel linker sequences that can be used to prepare recombinant toxic proteins having an A chain of a ricin-like toxin linked to a B chain by the linker sequence. The novel linker sequences of the invention are illustrated in FIGS. 1–18.

In one aspect the present invention provides a purified and isolated nucleic acid encoding a linker sequence comprising: the nucleic acid sequence of pAP301 as shown in FIG. 1A; the nucleic acid sequence of pAP302 as shown in FIG. 2A; the nucleic acid sequence of pAP303 as shown in FIG. 3A; the nucleic acid sequence of pAP304 as shown in FIG. 4A; the nucleic acid sequence of pAP305 as shown in FIG. 5A; the nucleic acid sequence of pAP308 as shown in FIG. 6A; the nucleic acid sequence of pAP309 as shown in FIG. 7A; the nucleic acid sequence of pAP313 as shown in FIG. 8A; the nucleic acid sequence of pAP314 as shown in FIG. 9A; the nucleic acid sequence of pAP315 as shown in FIG. 10A; the nucleic acid sequence of pAP316 as shown in FIG. 11A; the nucleic acid sequence of pAP318 as shown in FIG. 12A; the nucleic acid sequence of pAP320 as shown in FIG. 13A; the nucleic acid sequence of pAP321 as shown in FIG. 14A; the nucleic acid sequence of pAP322 as shown in FIG. 15A; the nucleic acid sequence of pAP323 as shown in FIG. 16A; the nucleic acid sequence of pAP324 as shown in FIG. 17A; and the nucleic acid sequence of pAP325 as shown in FIG. 18A.

In another aspect, the present invention provides a purified and isolated nucleic acid encoding a recombinant toxic protein comprising (a) a nucleotide sequence encoding an A chain of a ricin-like toxin, (b) a nucleotide sequence encoding a B chain of a ricin-like toxin and (c) a heterologous linker amino acid sequence, linking the A and B chains. The linker sequence is not a native linker sequence of a ricin-like toxin, but rather a synthetic heterologous linker sequence containing a cleavage recognition site for a specific protease. The A and or the B chain may be those of ricin. As used herein "specific protease" means a protease in any cell wherein there is expression of the protease at levels greater than those found in a corresponding healthy cell. Examples of a specific protease include MMPs, preferably MMP-2, MMP-9, MMP-14, and MT1-MMPs, and UPA, as well as others found in inflammatory cells and malignant cells. An inflammatory cell includes any cell involved in the inflammation process having a specific protease.

The recombinant toxic proteins employing the novel linker sequences of the present invention may be used to treat various forms of cells having specific proteases such as inflammatory disorders including rheumatoid arthritis, atherosclerotic cells, Crohn's disease, central nervous system disease as well as in cancer including, but not limited to, T- and B-cell lymphoproliferative diseases, ovarian cancer, pancreatic cancer, head and neck cancer, squamous cell carcinoma, gastrointestinal cancer, breast cancer, prostate, cancer and non small cell lung cancer. In an embodiment, of the invention the cleavage recognition site of the linker is the cleavage recognition site for a cancer-associated protease.

In particular embodiments, the amino acid sequence of the linker comprises the sequence of PAP301 shown in FIG. 1C; the sequence of PAP302 shown in FIG. 2C; the sequence of PAP303 shown in FIG. 3C; the sequence of PAP304 shown in FIG. 4C; the sequence of PAP305 shown in FIG.

5C; the sequence of PAP308 shown in FIG. 6C; the sequence of PAP309 shown in FIG. 7C; the sequence of PAP316 shown in FIG. 11C; the sequence of PAP318 shown in FIG. 12C; the sequence of PAP323 shown in FIG. 16C; the sequence of PAP324 shown in FIG. 17C; and the sequence of PAP325 shown in FIG. 18C; all cleaved by MMP-9; the sequence of PAP313 shown in FIG. 8C; the sequence of PAP314 shown in FIG. 9C; the sequence of PAP315 shown in FIG. 10C; the sequence of PAP320 shown in FIG. 13C; the sequence of PAP321 shown in FIG. 14C; the sequence of PAP322 shown in FIG. 15C; all cleaved by urokinase-type plasminogen activator.

In a preferred embodiment, the nucleic acid sequences of the recombinant toxic proteins containing ricin A and B chains with each of the linker sequences are shown in FIGS. 1B, 2B, 3B, 4B, 5B, 6B, 7B, 8B, 9B, 10B, 11B, 12B, 13B, 14B, 15B, 16B, 17B and 18B.

The present invention also provides a plasmid incorporating the nucleic acid of the invention. In another embodiment, the present invention provides a baculovirus transfer vector incorporating the nucleic acid of the invention.

In an aspect, the present invention provides a recombinant protein comprising an A chain of a ricin-like toxin, a B chain of a ricin-like toxin and a heterologous linker amino acid sequence, linking the A and B chains, wherein the linker sequence contains a cleavage recognition site for a specific protease. The A and/or the B chain may be those of ricin.

In a further aspect, the present invention provides a recombinant protein comprising an A chain of a ricin-like toxin, a B chain of a ricin-like toxin and a heterologous linker amino acid sequence, linking the A and B chains, wherein the linker sequence contains a cleavage recognition site for a inflammatory disease specific protease. The A and/or the B chain may be those of ricin. In an embodiment, the cleavage recognition site is the cleavage recognition site for an inflammation based protease substantially as described above. In a particular embodiment the inflammation is rheumatoid arthritis, atherosclerotic cells, Crohn's disease, or central nervous system disease.

In a further aspect, the present invention provides a recombinant protein comprising an A chain of a ricin-like toxin, a B chain of a ricin-like toxin and a heterologous linker amino acid sequence, linking the A and B chains, wherein the linker sequence contains a cleavage recognition site for a cancer-specific protease. The A and/or the B chain may be those of ricin. In an embodiment, the cleavage recognition site is the cleavage recognition site for a cancer protease substantially as described above. In a particular embodiment, the cancer is T-cell or B-cell lymphoproliferative disease, ovarian cancer, pancreatic cancer, head and neck cancer, squamous cell carcinoma, gastrointestinal cancer, breast cancer, prostate cancer, non small cell lung cancer.

In a further aspect, the invention provides a pharmaceutical composition for treating a cell, such as an inflammatory cell or cancer cell, having a specific protease, comprising a recombinant protein of the invention and a pharmaceutically acceptable carrier, diluent or excipient.

In yet another aspect, the invention provides a method of inhibiting or destroying a cell having a specific protease, such as an inflammatory cell or a cancer cell, comprising the steps of preparing a recombinant protein of the invention having a heterologous linker sequence which contains a cleavage recognition site for the specific protease, and administering the recombinant protein to the cells. In an embodiment, the inflammatory state is rheumatoid arthritis, atherosclerotic cells, Crohn's disease, or central nervous system disease. In another embodiment, the cancer is T-cell or B-cell lymphoproliferative disease, ovarian cancer, pancreatic cancer, head and neck cancer, squamous cell carcinoma, gastrointestinal cancer, breast cancer, prostate cancer, non small cell lung cancer.

The present invention also relates to a method of treating a cell having a specific protease such as an inflammatory cell or a cancer cell, wherein the cells affected by the condition and which have a specific protease, are treated by administering an effective amount of one or more recombinant proteins of the invention to an animal in need thereof.

Still further, a process is provided for preparing a pharmaceutical for treating a cell having a specific protease, such as an inflammatory cell or a cancer cell, wherein cells affected by condition have a specific protease, the steps for preparing the pharmaceutical comprising the steps of preparing a purified and isolated nucleic acid having a nucleotide sequence encoding an A chain of a ricin-like toxin, a B chain of a ricin-like toxin and a heterologous linker amino acid sequence, linking the A and B chains, wherein the linker sequence contains a cleavage recognition site for the specific protease; introducing the nucleic acid into a host cell; expressing the nucleic acid in the host cell to obtain a recombinant protein comprising an A chain of a ricin-like toxin, a B chain of a ricin-like toxin and a heterologous linker amino acid sequence, linking the A and B chains wherein the linker sequence contains the cleavage recognition site for the specific protease; and suspending the protein in a pharmaceutically acceptable carrier, diluent or excipient.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE DRAWINGS

The invention will be better understood with reference to the drawings in which:

FIG. 1A shows the nucleotide sequence of the MMP-9 linker region of pAP301 (SEQ ID NOS:1–4);

FIG. 1B shows the nucleotide sequence of the pAP301 insert containing ricin and the MMP-9 linker (SEQ ID NO:5);

FIG. 1C shows the amino acid sequence of the PAP301 linker and the wild type ricin linker (SEQ ID NOS:6–7);

FIG. 2A shows the nucleotide sequence of the MMP-9 30 linker region of pAP302 (SEQ ID NOS:8–11);

FIG. 2B shows the nucleotide sequence of the pAP302 insert containing ricin and the MMP-9 linker (SEQ ID NO:12);

FIG. 2C shows the amino acid sequence of the PAP302 linker and the wild type ricin linker (SEQ ID NOS:13–14);

FIG. 3A shows the nucleotide sequence of the MMP-9 linker region of pAP303 (SEQ ID NOS:15–18);

FIG. 3B shows the nucleotide sequence of the pAP303 insert containing ricin and the MMP-9 linker (SEQ ID NO:19);

FIG. 3C shows the amino acid sequence of the PAP303 linker and the wild type ricin linker (SEQ ID NOS:20–21);

FIG. 4A shows the nucleotide sequence of the MMP-9 linker region of pAP304 (SEQ ID NOS:22–25);

FIG. 4B shows the nucleotide sequence of the pAP304 insert containing ricin and the MMP-9 linker (SEQ ID NO:26);

FIG. 4C shows the amino acid sequence of the PAP304 linker and the wild type ricin linker (SEQ ID NOS:27–28);

FIG. 5A shows the nucleotide sequence of the MMP-9 linker region of pAP305 (SEQ ID NOS:29–32);

FIG. 5B shows the nucleotide sequence of the pAP305 insert containing ricin and the MMP-9 linker (SEQ ID NO:33);

FIG. 5C shows the amino acid sequence of the PAP305 linker and the wild type ricin linker (SEQ ID NOS:34–35);

FIG. 6A shows the nucleotide sequence of the MMP-9 linker region of pAP308 (SEQ ID NOS:36–39);

FIG. 6B shows the nucleotide sequence of the pAP308 insert containing ricin and the MMP-9 linker (SEQ ID NO:40);

FIG. 6C shows the amino acid sequence of the pAP308 linker and the wild type ricin linker (SEQ ID NOS:41–42);

FIG. 7A shows the nucleotide sequence of the MMP-9 linker region of pAP309 (SEQ ID NOS:43–46);

FIG. 7B shows the nucleotide sequence of the pAP309 insert containing ricin and the MMP-9 linker (SEQ ID NO:47);

FIG. 7C shows the amino acid sequence of the PAP309 linker and the wild type ricin linker (SEQ ID NOS:48–49);

FIG. 8A shows the nucleotide sequence of the UPA linker region of pAP313 (SEQ ID NOS:50–53);

FIG. 8B shows the nucleotide sequence of the pAP313 insert containing ricin and the UPA linker (SEQ ID NO:54);

FIG. 8C shows the amino acid sequence of the PAP313 linker and the wild type ricin linker (SEQ ID NOS:55–56);

FIG. 9A shows the nucleotide sequence of the UPA linker region of pAP314 (SEQ ID NOS:57–60);

FIG. 9B shows the nucleotide sequence of the pAP314 insert containing ricin and the UPA linker (SEQ ID NO:61);

FIG. 9C shows the amino acid sequence of the PAP314 linker and the wild type ricin linker (SEQ ID NOS:62–63);

FIG. 10A shows the nucleotide sequence of the UPA linker region of pAP315 (SEQ ID NOS:64–67);

FIG. 10B shows the nucleotide sequence of the pAP315 insert containing ricin and the UPA linker (SEQ ID NO:68);

FIG. 10C shows the amino acid sequence of the PAP315 linker and the wild type ricin linker (SEQ ID NOS:69–70);

FIG. 11A shows the nucleotide sequence of the MMP-9 linker region of pAP316 (SEQ ID NOS:71–74);

FIG. 11B shows the nucleotide sequence of the pAP316 insert containing ricin and the MMP-9 linker (SEQ ID NO:75);

FIG. 11C shows the amino acid sequence of the PAP316 linker and the wild type ricin linker (SEQ ID NOS:76–77);

FIG. 12A shows the nucleotide sequence of the MMP-9 linker region of pAP318 (SEQ ID NOS:78–81);

FIG. 12B shows the nucleotide sequence of the pAP318 insert containing ricin and the MMP-9 linker (SEQ ID NO:82);

FIG. 12C shows the amino acid sequence of the PAP318 linker and the wild type ricin linker (SEQ ID NOS:83–84);

FIG. 13A shows the nucleotide sequence of the UPA linker region of pAP320 (SEQ ID NOS:85–88);

FIG. 13B shows the nucleotide sequence of the pAP320 insert containing ricin and the UPA linker (SEQ ID NO:89);

FIG. 13C shows the amino acid sequence of the PAP320 linker and the wild type ricin linker (SEQ ID NOS:90–91);

FIG. 14A shows the nucleotide sequence of the UPA linker region of pAP321 (SEQ ID NOS:92–95);

FIG. 14B shows the nucleotide sequence of the pAP321 insert containing ricin and the UPA linker (SEQ ID NO:96);

FIG. 14C shows the amino acid sequence of the PAP321 linker and the wild type ricin linker (SEQ ID NOS:97–98);

FIG. 15A shows the nucleotide sequence of the UPA linker region of pAP322 (SEQ ID NOS:99–102);

FIG. 15B shows the nucleotide sequence of the pAP322 insert containing ricin and the UPA linker (SEQ ID NO:103);

FIG. 15C shows the amino acid sequence of the PAP322 linker and the wild type ricin linker (SEQ ID NOS: 104–105);

FIG. 16A shows the nucleotide sequence of the MMP-9 linker region of pAP323 (SEQ ID NOS:106–109);

FIG. 16B shows the nucleotide sequence of the pAP323 insert containing ricin and the MMP-9 linker (SEQ ID NO:110);

FIG. 16C shows the amino acid sequence of the PAP323 linker and the wild type ricin linker (SEQ ID NOS: 111–112);

FIG. 17A shows the nucleotide sequence of the MMP-9 linker region of pAP324 (SEQ ID NOS:113–116);

FIG. 17B shows the nucleotide sequence of the pAP324 insert containing ricin and the MMP-9 linker (SEQ ID NO:117);

FIG. 17C shows the amino acid sequence of the PAP324 linker and the wild type ricin linker (SEQ ID NOS: 118–119);

FIG. 18A shows the nucleotide sequence of the MMP-9 linker region of pAP325 (SEQ ID NOS:120–123);

FIG. 18B shows the nucleotide sequence of the pAP325 insert containing ricin and the MMP-9 linker (SEQ ID NO:124);

FIG. 18C shows the amino acid sequence of the PAP325 linker and the wild type ricin linker (SEQ ID NOS: 125–126);

DETAILED DESCRIPTION OF THE INVENTION

Figure 19:
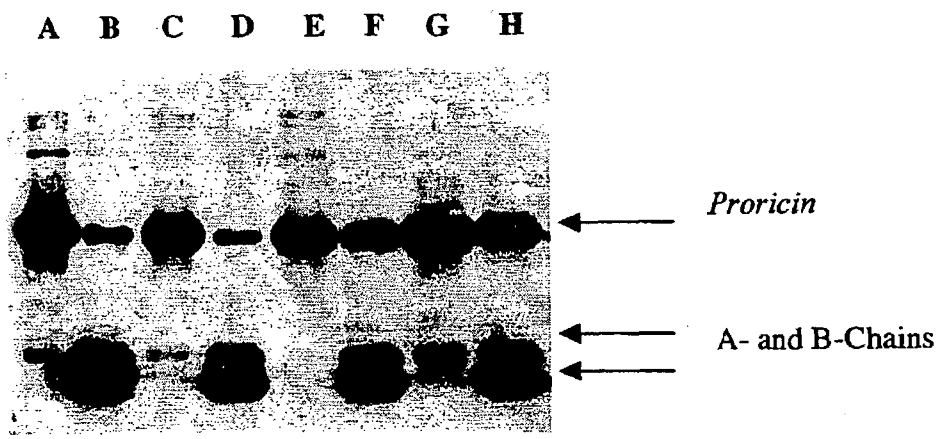
FIG. 19 shows the cleavage products of an MMP-9 digestion of PAP323, PAP324 and PAP325.

1. Nucleic Acid Molecules of the Invention

As mentioned above, the present invention relates to isolated and purified nucleic acid molecules encoding linker sequences. The present invention also relates to isolated and purified nucleic acid molecules encoding a recombinant toxic protein comprising (a) a nucleotide sequence encoding an A chain of a ricin-like toxin, (b) a nucleotide sequence encoding a B chain of a ricin-like toxin and (c) a nucleotide sequence encoding a linker amino acid sequence of the invention, linking the A and B chains. The heterologous linker sequence contains a cleavage recognition site for a specific protease.

The term "isolated and purified" as used herein refers to a nucleic acid substantially free of cellular material or culture medium when produced by recombinant DNA techniques, or chemical precursors, or other chemicals when chemically synthesized. An "isolated and purified" nucleic acid is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded.

The term "linker sequence" as used herein refers to an internal amino acid sequence within the protein encoded by a nucleic acid molecule of the invention which contains residues linking the A and B chain of a ricin-like toxin so as to render the A chain incapable of exerting its toxic effect, for example catalytically inhibiting translation of an eukaryotic ribosome. The linker sequences of the invention are heterologous to the A and B chain of a ricin-like toxin. By heterologous is meant that the linker sequence is not a sequence native to the A or B chain of a ricin-like toxin or precursor thereof. However, preferably, the linker sequence may be of a similar length to the linker sequence of a ricin-like toxin and should not interfere with the role of the B chain in cell binding and transport into the cytoplasm. When the linker sequence is cleaved the A chain becomes active or toxic.

The nucleic acid molecule of the invention encoding a recombinant toxic protein is cloned by subjecting a preproricin cDNA clone to site-directed mutagenesis in order to generate a series of variants differing only in the sequence between the A and B chains (linker region). Oligonucleotides, corresponding to the extreme 5' and 3' ends of the preproricin gene are synthesized and used to PCR amplify the gene. Using the cDNA sequence for preproricin (Lamb et al., *Eur. J. Biochem.* 145:266–270 (1985)), several oligonucleotide primers are designed to flank the start and stop codons of the preproricin open reading frame.

The preproricin cDNA is amplified using the upstream primer Ricin-99 or Ricin-109 and the downstream primer Ricin1729C with Vent DNA polymerase (New England Biolabs) using standard procedures (Sambrook et al., Molecular Cloning: A Laboratory Manual, Second Edition, (Cold Spring Harbor Laboratory Press, 1989)). The purified PCR fragment encoding the preproricin cDNA is, then ligated into an Eco RV-digested pBluescript 11 SK plasmid (Stratagene), and is used to transform competent XL1-Blue cells (Stratagene). The cloned PCR product containing the putative preproricin gene is confirmed by DNA sequencing of the entire cDNA clone.

The preproricin cDNA clone is subjected to site directed mutagenesis; in order to generate a series of variants differing only in the sequence between the A and B chains (linker region). The wild-type preproricin linker region is replaced with the heterogenous linker sequences that are cleaved by the various specific proteases.

The linker regions of the variants encode a cleavage recognition sequence for a specific protease. The mutagenesis and cloning strategies used to generate a specific protease-sensitive linker variant are summarized in WO 98149311 to the present inventor. Briefly, the first step involves a DNA amplification using a set of mutagenic primers in combination with the two flanking primers Ricin-109Eco and Ricin1729C PstI. Restriction digested PCR fragments are gel purified and then ligated with PVL1393 which has been digested with Eco RI and PstI. Ligation reactions are used to transform competent XLI-Blue cells (Stratagene). Recombinant clones are identified by restriction digests of plasmid miniprep, DNA and the mutant linker sequences are confirmed by DNA sequencing.

The nucleotide sequences of the novel linker sequences of the invention are as follows: the nucleic acid sequence of pAP301 is shown in FIG. 1A; the nucleic acid sequence of pAP302 is shown in FIG. 2A; the nucleic acid sequence of pAP303 is shown in FIG. 3A; the nucleic acid sequence of pAP304 is shown in FIG. 4A; the nucleic acid sequence of pAP305 is shown in FIG. 5A; the nucleic acid sequence of pAP308 is shown in FIG. 6A; the nucleic acid sequence of pAP309 is shown in FIG. 7A; the nucleic acid sequence of pAP313 is shown in FIG. 8A; the nucleic acid sequence of pAP314 is shown in FIG. 9A; the nucleic acid sequence of pAP315 is shown in FIG. 10A; the nucleic acid sequence of pAP316 is shown in FIG. 11A; the nucleic acid sequence of pAP318 is shown in FIG. 12A; the nucleic acid sequence of pAP320 is shown in FIG. 13A; the nucleic acid sequence of pAP321 is shown in FIG. 14A; the nucleic acid sequence of pAP322 is shown in FIG. 15A; the nucleic acid sequence of pAP323 is shown in FIG. 16A; the nucleic acid sequence of pAP324 is shown in FIG. 17A; and the nucleic acid sequence of pAP325 is shown in FIG. 18A.

The nucleic acid molecule encoding a recombinant protein of the invention has sequences encoding an A chain of a ricin-like toxin, a B chain of a ricin-like toxin and a heterologous linker sequence containing a cleavage recognition site for a specific protease as described above. The nucleotide sequences encoding the recombinant proteins of the invention are shown in FIGS. 1B–18B. The nucleic acid may be expressed to provide a recombinant protein having an A chain of a ricin-like toxin, a B chain of a ricin-like toxin and a heterologous linker sequence containing a cleavage recognition site for a specific protease.

The nucleic acid molecule may comprise the A and/or B chain of ricin. The ricin gene has been cloned and sequenced, and the X-ray crystal structures of the A and B chains are published (Rutenber, E., et al. Proteins 10:240–250 (1991); Weston et al., *Mol. Biol.* 244:410–422 (1994); Lamb and Lord, *Eur. J. Biochem.* 14:265 (1985); Halling, K., et al., *Nucleic Acids Res.* 13:8019 (1985)). It will be appreciated that the invention includes nucleic acid molecules encoding truncations of A and B chains of ricin-like proteins and analogs and homologs of A and B chains of ricin-like proteins and truncations thereof (i.e., ricin-like proteins), as described herein. It will further be appreciated that variant forms of the nucleic acid molecules of the invention which arise by alternative splicing of an mRNA corresponding to a cDNA of the invention are encompassed by the invention.

Another aspect of the invention provides a nucleotide sequence which hybridizes under high stringency conditions to a nucleotide sequence encoding the A and/or B chains of a ricin-like protein. Appropriate stringency conditions which promote DNA hybridization are known to those skilled in the art, or can be found in Current Protocols in Molecular Biology, John Wiley & Sons, N.Y. (1989), 6.3.1 6.3.6. For example, 6.0× sodium chloride/sodium citrate (SSC) at about 45° C., followed by a wash of 2.0×SSC at 50° C. may be employed.

The stringency may be selected based on the conditions used in the wash step. By way of example, the salt concentration in the wash step can be selected from a high stringency of about 0.2×SSC at 50° C. In addition, the temperature in the wash step can be at high stringency conditions, at about 65° C.

The nucleic acid molecule may comprise the A and/or B chain of a ricin-like toxin. Methods for cloning ricin-like toxins are known in the art and are described, for example, in E.P. 466,222. Sequences encoding ricin or ricin-like A and B chains may be obtained by selective amplification of a coding region, using sets of degenerative primers or probes for selectively amplifying the coding region in a genomic or cDNA library. Appropriate primers may be selected from the nucleic acid sequence of A and B chains of ricin or ricin-like toxins. It is also possible to design synthetic oligonucleotide primers from the nucleotide sequences for use in PCR. Suitable primers may be selected from the sequences encoding regions of ricin-like proteins which are highly conserved, as described for example in U.S. Pat. No. 5,101,025 and E.P. 466,222.

A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al. (*Biochemistry* 18, 5294–5299 (1979)). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.). It will be appreciated that the methods described above may be used to obtain the coding sequence from plants, bacteria or fungi, preferably plants, which produce known ricin-like proteins and also to screen for the presence of genes encoding as yet unknown ricin-like proteins.

A sequence containing a cleavage recognition site for a specific protease may be selected based on the disease or condition which is to be targeted by the recombinant protein. The cleavage recognition site may be selected from sequences known to encode a cleavage recognition site specific proteases of the disease or condition to be treated. Sequences encoding cleavage recognition sites may be identified by testing the expression product of the sequence for susceptibility to cleavage by the respective protease. A polypeptide containing the suspected cleavage recognition site may be incubated with a specific protease and the amount of cleavage product determined (Dilannit, 1990, J. Biol. Chem. 285: 17345–17354 (1990)). The specific protease may be prepared by methods known in the art and used to test suspected cleavage recognition sites.

The nucleic acid molecule of the invention may be prepared by site directed mutagenesis. For example, the cleavage site of a specific protease may be prepared by site directed mutagenesis of the homologous linker sequence of a proricin-like toxin. Procedures for cloning proricin-like genes, encoding a linker sequence are described in EP 466,222. Site directed mutagenesis may be accomplished by DNA amplification of mutagenic primers in combination with flanking primers.

The nucleic acid molecule of the invention may also encode a fusion protein. A sequence encoding a heterologous linker sequence containing a cleavage recognition site for a specific protease may be cloned from a cDNA or genomic library or chemically synthesized based on the known sequence of such cleavage sites. The heterologous linker sequence may then be fused in frame with the sequences encoding the A and B chains of the ricin-like toxin for expression as a fusion protein. It will be appreciated that a nucleic acid molecule encoding a fusion protein may contain a sequence encoding an A chain and a B chain from the same ricin-like toxin or the encoded A and B chains may be from different toxins. For example, the A chain may be derived from ricin and the B chain may be derived from abrin. A protein may also be prepared by chemical conjugation of the A and B chains and linker sequence using conventional coupling agents for covalent attachment.

An isolated and purified nucleic acid molecule of the invention which is RNA can be isolated by cloning a cDNA encoding an A and B chain and a linker into an appropriate vector which allows for transcription of the cDNA to produce an RNA molecule which encodes a protein of the invention. For example, a cDNA can be cloned downstream of a bacteriophage promoter, (e.g. a T7 promoter) in a vector, cDNA can be transcribed in vitro with T7 polymerase, and the resultant RNA can be isolated by standard techniques.

II. Novel Linkers and Recombinant Proteins of the Invention

As previously mentioned, the invention provides novel linker sequences. Preferably, the amino acid sequence of the linker is selected from: the amino acid sequence of PAP301 as shown in FIG. 1C; the amino acid sequence of PAP302 as shown in FIG. 2C; the amino acid sequence of PAP303 as shown in FIG. 3C; the amino acid sequence of PAP304 as shown in FIG. 4C; the amino acid sequence of PAP305 as shown in FIG. 5C; the amino acid sequence of PAP308 as shown in FIG. 6C; the amino acid sequence of PAP309 as shown in FIG. 7C; the amino acid sequence of PAP313 as shown in FIG. 8C; the amino acid sequence of PAP314 as shown in FIG. 9C; the amino acid sequence of PAP315 as shown in FIG. 10C; the amino acid sequence of PAP316 as shown in FIG. 11C; the amino acid sequence of PAP318 as shown in FIG. 12C; the amino acid sequence of PAP320 as shown in FIG. 13C; the amino acid sequence of PAP321 as shown in FIG. 14C; the amino acid sequence of PAP322 as shown in FIG. 15C; the amino acid sequence of PAP323 as shown in FIG. 16C; the amino acid sequence of PAP324 as shown in FIG. 17C; and the amino acid sequence of PAP325 as shown in FIG. 18C.

The present invention also provides recombinant proteins which incorporate the A and B chains of a ricin-like toxin linked by a heterologous linker sequence containing a cleavage recognition site for a specific protease as described above. It is an advantage of the recombinant proteins of the invention that they are non-toxic until the A chain is liberated from the B chain by specific cleavage of the linker by the target specific protease.

The recombinant protein may be used to specifically target for example, cancer cells in the absence of additional specific cell-binding components to target cancer cells. It is a further advantage that the specific protease cleaves the heterologous linker intracellularly thereby releasing the toxic A chain directly into the cytoplasm of the target cell. As a result, said cells are specifically targeted and normal cells are not directly exposed to the activated free A chain.

Ricin is a plant derived ribosome inhibiting protein which blocks protein synthesis in eukaryotic cells. Ricin may be derived from the seeds of *Ricinus communis* (castor oil plant). The ricin toxin is a glycosylated heterodimer with A and B chain molecular masses of 30,625 Da and 31,431 Da respectively. The A chain of ricin has an N-glycosidase activity and catalyzes the excision of a specific adenine residue from the 28S rRNA of eukaryotic ribosomes (Endo, Y; & Tsurugi, K. J. Biol. Chem. 262:8128 (1987)). The B chain of ricin, although not toxic in itself, promotes the toxicity of the A chain by binding to galactose residues on the surface of eukaryotic cells and stimulating receptor-mediated endocytosis of the toxin molecule (Simmons et al., *Biol. Chem.* 261:7912 (1986)).

All protein toxins are initially produced in an inactive, precursor form. Ricin is initially produced as a single polypeptide (preproricin) with a 35 amino acid N-terminal presequence and 12 amino acid linker between the A and B chains. The pre-sequence is removed during translocation of the ricin precursor into the endoplasmic reticulum (Lord, J. M., Eur. J. *Biochem.* 146:403–409 (1985) and Lord, J. M., Eur. J. *Biochem.* 146:411–416 (1985)). The proricin is then translocated into specialized organelles called protein bodies where a plant protease cleaves the protein at a linker region between the A and B chains (Lord, J. M. et al., FASAB journal 8:201–208 (1994)). The two chains, however, remain covalently attached by an interchain disulfide bond (cysteine 259 in the A chain to cysteine 4 in the B chain) and mature disulfide linked ricin is stored in protein bodies inside plant cells. The A chain is inactive in the proricin (O'Hare, M., et al., *FEBS Lett.* 273:200–204 (1990)) and it is inactive in the disulfide-linked mature ricin (Richardson, P. T. et al., FEBS *Lett.* 255:15–20 (1989)). The ribosomes of the castor bean plant are themselves susceptible to inactivation by ricin A chain; however, as there is no cell surface galactose to permit B chain recognition the A chain cannot re-enter the cell.

Ricin-like proteins include, but are not limited to, bacterial, fungal and plant toxins which have A and B chains and inactivate ribosomes and inhibit protein synthesis. The A chain is an active polypeptide subunit which is responsible for the pharmacologic effect of the toxin. In most cases the active component of the A chain is an enzyme. The B chain is responsible for binding the toxin to the cell surface and is thought to facilitate entry of the A chain into the cell cytoplasm. The A and B chains in the mature toxins are linked by disulfide bonds. The toxins most similar in structure to ricin are plant toxins which have one A chain and one B chain. Examples of such toxins include abrin which may be isolated from the seeds of *Abrus precatorius*, modeccin, volkensin and viscumin.

Ricin-like bacterial proteins include diphtheria toxin, which is produced by *Corynebacterium diphtheriae, Pseudomonas* exotoxin and cholera toxin. It will be appreciated that the term ricin-like toxins is also intended to include the A chain of those toxins which have only an A chain. The recombinant proteins of the invention could include the A chain of these toxins conjugated to, or expressed as, a recombinant protein with the B chain of another toxin. Examples of plant toxins having only an A chain include trichosanthin, MMC and pokeweed antiviral proteins, dianthin 30, dianthin 32, crotin II, curcin 11 and wheat germ inhibitor. Examples of fungal toxins having only an A chain include alpha-sarcin, restrictocin, mitogillin, enomycin, phenomycin. Examples of bacterial toxins having only an A chain include cytotoxin from *Shigella dysenteriae* and related Shiga-like toxins. Recombinant trichosanthin and the coding sequence thereof is disclosed in U.S. Pat. Nos. 5,101,025 and 5,128,460.

In addition to the entire A or B chains of a ricin-like toxin, it will be appreciated that the recombinant protein of the invention may contain only that portion of the A chain which is necessary for exerting its cytotoxic effect. For example, the first 30 amino acids of the ricin A chain may be removed resulting in a truncated A chain which retains toxic activity. The truncated ricin or ricin-like A chain may be prepared by expression of a truncated gene or by proteolytic degradation, for example with Nagarase (Funmatsu et al., *Jap. J. Med. Sci. Biol.* 23:264–267 (1970)). Similarly, the recombinant protein of the invention may contain only that portion of the B chain necessary for galactose recognition, cell binding and transport into the cell cytoplasm. Truncated B chains are described for example in E.P. 145,111. The A and B chains may be glycosylated or non-glycosylated. Glycosylated A and B chains may be obtained by expression in the appropriate host cell capable of glycosylation. Non-glycosylated chains may be obtained by expression in nonglycosylating host cells or by treatment to remove or destroy the carbohydrate moieties.

The proteins of the invention may be prepared using recombinant DNA methods. Accordingly, the nucleic acid molecules of the present invention may be incorporated in a known manner into an appropriate expression vector which ensures good expression of the protein. Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence.

Suitable regulatory sequences may be derived from a variety of sources, including bacterial, fungal, viral, mammalian, or insect genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native A and B chains and/or its flanking regions.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a fusion moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The term "transformed host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of prokaryotic and eukaryotic host cells. For example, the proteins of the invention may be expressed in bacterial cells such as *E. coli*, insect cells (using baculovirus), yeast cells or mammalian cells. Other suitable host cells can be found in Goeddel, Gene Expression Technology: Methods in Enzymology 185, Academic Press, San Diego, Calif. (1991).

More particularly, bacterial host cells suitable for carrying out the present invention include *E. coli, B. subtilis, Salmonella typhimurium*, and various species within the genus *Pseudomonas, Streptomyces*, and *Staphylococcus*, as well as many other bacterial species well known to one of ordinary skill in the art. Suitable bacterial expression vectors preferably comprise a promoter which functions in the host cell, one or more selectable phenotypic markers, and a bacterial origin of replication. Representative promoters include the β-lactamase (penicillinase) and lactose promoter system (see Chang et al., *Nature* 275:615 (1978)), the trp promoter (Nichols and Yanofsky, Meth in Enzymology 101:155, (1983) and the tac promoter (Russell et al., Gene 20:231, (1982)). Representative selectable markers include various antibiotic resistance markers such as the kanamycin or ampicillin resistance genes. Suitable expression vectors include but are not limited to bacteriophages such as lambda derivatives or plasmids such as pBR322 (Bolivar et al., *Gene* 2:9S, (1977)), the pUC plasmids pUC18, pUC19, pUC118, pUC119 (see Messing, Meth in Enzymology 101:20–77, 1983 and Vieira and Messing, *Gene* 19:259–268 (1982)), and pNH8A, pNH16a, pNH18a, and Bluescript M13 (Stratagene, La Jolla, Calif.).

Typical fusion expression vectors which may be used are discussed above, e.g. pGEX (Amrad Corp., Melbourne, Australia), pMAL (New England Biolabs, Beverly, Mass.) and pRIT5 (Pharmacia, Piscataway, N.J.). Examples of inducible non-fusion expression vectors include pTrc (Arnann et al., *Gene* 69:301–315 (1988)) and pET 11d (Studier et al., Gene Expression Technology: Methods in Enzymology 185, Academic Press, San Diego, Calif., 60–89 (1990)).

Yeast and fungi host cells suitable for carrying out the present invention include, but are not limited to *Saccharomyces cerevisae*, the genera *Pichia* or *Kluyveromyces* and various species of the genus *Aspergillus*. Examples of vectors for expression in yeast *S. cerivisae* include pYepSec1 (Baldari. et al., *Embo J.* 6:229–234 (1987)), pMFa (Kurjan and Herskowitz, *Cell* 30:933–943 (1982)), pJRY88 (Schultz et al., *Gene* 54:113–123 (1987)), and pYES2 (Invitrogen Corporation, San Diego, Calif.). Protocols for the transformation of yeast and fungi are well known to those of ordinary skill in the art (see Hinnen et al., *Proc. Natl.Acad. Sci. USA* 75:1929 (1978); Itoh et al., *J. Bacteriology* 153:163 (1983), and Cullen et al. (*BiolTechnology* 5:369 (1987)).

Mammalian cells suitable for carrying out the present invention include, among others: COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells. Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., *Nature* 329:840 (1987)) and pMT2PC (Kaufman et al., *EMBO J.* 6:187–195 (1987)).

Given the teachings provided herein, promoters, terminators, and methods for introducing expression vectors of an appropriate type into plant, avian, and insect cells may also be readily accomplished. For example, within one embodiment, the proteins of the invention may be expressed from plant cells (see Sinkar et al., *J. Biosci* (Bangalore) 11:47–58 (1987), which reviews the use of *Agrobacterium rhizogenes* vectors; see also Zambryski et al., Genetic Engineering, Principles and Methods, Hollaender and Setlow (eds.), Vol. VI, pp. 253–278, Plenum Press, New York (1984), which describes the use of expression vectors for plant cells, including, among others, PAPS2022, PAPS2023, and PAPS2034)

Insect cells suitable for carrying out the present invention include cells and cell lines from *Bombyx, Trichoplusia* or *Spodotera* species. Baculovirus vectors available for expression of proteins in cultured insect cells (SF 9 cells) include the pAc series (Smith et al., *Mol. Cell Biol.* 3:2156–2165 (1983)) and the pVL series (Lucklow, V. A., and Summers, M. D., Virology 170:31–39 (1989)). Some baculovirus-insect cell expression systems suitable for expression of the recombinant proteins of the invention are described in PCT/US/02442.

Alternatively, the proteins of the invention may also be expressed in non-human transgenic animals such as, rats, rabbits, sheep and pigs (Hammer et al. *Nature* 315:680–683 (1985); Palmiter et al. *Science* 222:809–814 (1983); Brinster et al. *Proc. Natl. Acad. Sci. USA* 82:4438–4442 (1985); Palmiter and Brinster *Cell* 41:343–345 (1985) and U.S. Pat. No. 4,736,866).

The proteins of the invention may also be prepared by chemical synthesis using techniques well known in the chemistry of proteins such as solid phase synthesis (Merrifield, *J. Am. Chem. Assoc.* 85:2149–2154 (1964)) or synthesis in homogenous solution (Houbenweyl, Methods of Organic Chemistry, ed. E. Wansch, Vol. 15 I and II, Thieme, Stuttgart (1987)).

The present invention also provides proteins comprising an A chain of a ricin-like toxin, a B chain of a ricin-like toxin and a heterologous linker amino acid sequence linking the A and B chains, wherein the linker sequence contains a cleavage recognition site for a specific protease. Such a protein could be prepared other than by recombinant means, for example by chemical synthesis or by conjugation of A and B chains and a linker sequence isolated and purified from their natural plant, fungal or bacterial source. Such A and B chains could be prepared having the glycosylation pattern of the native ricin-like toxin.

N-terminal or C-terminal fusion proteins comprising the protein of the invention conjugated with other molecules, such as proteins may be prepared by fusing, through recombinant techniques. The resultant fusion proteins contain a protein of the invention fused to the selected protein or marker protein as described herein. The recombinant protein of the invention may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate. Examples of proteins which may be used to prepare fusion proteins or conjugates include cell binding proteins such as immunoglobulins, hormones, growth factors, lectins, insulin, low density lipoprotein, glucagon, endorphins, transferrin, bombesin, asialoglycoprotein glutathione-S-transferase (GST), hemagglutinin (HA), and truncated myc.

III. Utility of the Nucleic Acid Molecules and Proteins of the Invention (a) Therapeutic Methods As mentioned above, matrix metalloproteinases (MMPs or matrixins) are zinc-dependent proteinases and the expression of MMP genes is reported to be activated in inflammatory disorders (e.g. rheumatoid arthritis) and malignancy. In addition, there are reports of increased activation and expression of urokinase type plasminogen activator in inflammatory disorders such a rheumatoid arthritis (Slot, O., et al. 1999), osteoarthritis (Pap, G. et al., 2000), atherosclerotic cells (Falkenberg, M., et al., 1998) Crohn's disease (Desreumaux P, et al. 1999), central nervous system disease (Cuzner and Opdenakker, 1999) as well as in malignancy. Accordingly, the recombinant proteins of the invention may be used to specifically inhibit or destroy cells that contain a specific protease that can cleave the linker sequence of the recombinant protein. More particularly, the recombinant proteins of the invention may be used to specifically inhibit or destroy cancer cells that contain a protease that can cleave the linker sequence of the recombinant protein.

It is an advantage of the recombinant proteins of the invention that they have specificity for cells that contain a specific protease, including those of inflammatory disorders and cancer cells, without the need for a cell binding component. The ricin-like B chain of the recombinant proteins recognize galactose moieties on the cell surface and ensure that the protein is taken up by, for example, a cancer cell and released into the cytoplasm. When the protein is internalized into a normal cell, cleavage of the heterologous linker would not occur in the absence of the specific protease, and the A chain will remain inactive bound to the B chain. Conversely, when the protein is internalized into a cell having a specific protease, the specific protease will cleave the cleavage recognition site in the linker thereby releasing the toxic A chain.

Accordingly, the present invention provides a method of inhibiting or destroying cells having a specific protease, for examples inflammatory cells or cancer cells, comprising contacting such cells with an effective amount of a recombinant protein or a nucleic acid molecule encoding a recombinant protein of the invention. The present invention also provides a method of treating a cell having a specific protease, comprising administering an effective amount of a recombinant protein or a nucleic acid molecule encoding a recombinant protein of the invention to an animal in need thereof.

The term "effective amount" as used herein means an amount effective, at dosages and for periods of time necessary to achieve the desired result.

The term "animal" as used herein means any member of the animal kingdom including all mammals, birds, fish, reptiles and amphibians. Preferably, the animal to be treated is a mammal, more preferably a human.

The specificity of a recombinant protein of the invention may be tested by treating the protein with the specific protease which is thought to be specific for the cleavage recognition site of the linker and assaying for cleavage products. For example, specific proteases may be isolated from cancer cells, or they may be prepared recombinantly, for example following the procedures in Darket et al. (*J. Biol. Chem.* 254:2307–2312 (1988)). The cleavage products may be identified for example based on size, antigenicity or activity. The toxicity of the recombinant protein may be investigated by subjecting the cleavage products to an in vitro translation assay in cell lysates, for example using Brome Mosaic Virus mRNA as a template. Toxicity of the cleavage products may be determined using a ribosomal inactivation assay (Westby et al., *Bioconjugate Chem.* 3:377–382 (1992)). The effect of the cleavage products on protein synthesis may be measured in standardized assays of in vitro translation utilizing partially defined cell free systems composed for example of a reticulocyte lysate preparation as a source of ribosomes and various essential cofactors, such as mRNA template and amino acids. Use of radiolabelled amino acids in the mixture allows quantitation of incorporation of free amino acid precursors into trichloroacetic acid precipitable proteins. Rabbit reticulocyte lysates may be conveniently used (O'Hare, *FEBS Lett.* 273:200–204 (1990)).

The ability of the recombinant proteins of the invention to selectively inhibit or destroy cells having specific proteases may be readily tested in vitro using cell lines having the specific protease, such as cancer cell lines. The selective inhibitory effect of the recombinant proteins of the invention may be determined, for example, by demonstrating the selective inhibition of cellular proliferation in cancer cells or infected cells.

Toxicity may also be measured based on cell viability, for example, the viability of cancer and normal cell cultures exposed to the recombinant protein may be compared. Cell viability may be assessed by known techniques, such as trypan blue exclusion assays.

In another example, a number of models may be used to test the cytotoxicity of recombinant proteins having a heterologous linker sequence containing a cleavage recognition site for a cancer associated matrix metalloprotease. Thompson, E. W. et al. (*Breast Cancer Res. Treatment* 31:357–370 (1994)) has described a model for the determination of invasiveness of human breast cancer cells in vitro by measuring tumour cell-mediated proteolysis of extracellular matrix and tumour cell invasion of reconstituted basement membrane (collagen, laminin, fibronectin, Matrigel or gelatin). Other applicable cancer cell models include cultured ovarian adenocarcinoma cells (Young, T. N. et al. *Gynecol. Oncol.* 62:89–99 (1996); Moore, D. H. et al. *Gynecol. Oncol.* 65:78–82 (1997)), human follicular thyroid cancer cells (Demeure, M. J. et al., *World J. Surg.* 16:770–776 (1992)), human melanoma (A-2058) and fibrosarcoma (HT-1080) cell lines (Mackay, A. R. et al. *Lab. Invest.* 70:781 783 (1994)), and lung squamous (HS-24) and adenocarcinoma (SB-3) cell lines (Spiess, E. et al. J. *Histochem. Cytochem.* 42:917–929 (1994)). An in vivo test system involving the implantation of tumours and measurement of tumour growth and metastasis in athymic nude mice has also been described (Thompson, E. W. et al., *Breast Cancer Res. Treatment* 31:357–370 (1994); Shi, Y. E. et al., *Cancer Res.* 53:1409–1415 (1993)).

Although the primary specificity of the proteins of the invention for cells having a specific protease is mediated by the specific cleavage of the cleavage recognition site of the linker, it will be appreciated that specific cell binding components may optionally be conjugated to the proteins of the invention. Such cell binding components may be expressed as fusion proteins with the proteins of the invention or the cell binding component may be physically or chemically coupled to the protein component. Examples of suitable cell binding components include antibodies to cancer proteins.

Antibodies having specificity for a cell surface protein may be prepared by conventional methods. A mammal, (e.g. a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art, (e.g. the hybridoma technique originally developed by Kohler and Milstein (*Nature* 256:495–497 (1975)) as well as other techniques such as the human B-cell hybridoma technique (Kozbor et al., *Immunol.Today* 4:72 (1983)), the EBV-hybridoma technique to produce human monoclonal antibodies (Cole et al., Methods Enzymol, 121: 140–67 (1986)), and screening of combinatorial antibody libraries (Huse et al., *Science* 246:1275 (1989)). Hybridoma cells can be screened immunochemically for production of antibodies specifically reactive with the peptide and the monoclonal antibodies can be isolated.

The term "antibody" as used herein is intended to include fragments thereof which also specifically react with a cell surface component. Antibodies can be fragmented using conventional techniques and the fragments screened for utility in the same manner as described above. For example, $F(ab')_2$ fragments can be generated by treating antibody with pepsin. The resulting $F(ab')_2$ fragment can be treated to reduce disulfide bridges to produce Fab fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes a cell surface antigen (See, for example, Morrison et al., Proc. *Natl. Acad. Sci. U.S.A.* 81:6851 (1985); Takeda et al., *Nature* 314:452 (1985), Cabilly et al., U.S. Pat. No. 4,816,567; Boss et al., U.S. Pat. No. 4,816,397; Tanaguchi et al., E.P. Patent No. 171,496; European Patent No. 173,494; United Kingdom Patent No. GB 2177096B). It is expected that chimeric antibodies would be less immunogenic in a human subject than the corresponding non-chimeric antibody.

Monoclonal or chimeric antibodies specifically reactive against cell surface components can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g. Teng et al., *Proc. Natl. Acad. Sci. U.S.A.,* 80:7308–7312 (1983); Kozbor et al., *Immunology Today* 4:7279 (1983); Olsson et al., *Meth. Enzymol.,* 92:3–16 (1982), and PCT Publication WO92/06193 or EP 239,400). Humanized antibodies can also be commercially produced (Scotgen Limited, 2 Holly Road, Twickenham, Middlesex, Great Britain.)

Specific antibodies, or antibody fragments, reactive against cell surface components may also be generated by screening expression libraries encoding immunoglobulin genes, or portions thereof, expressed in bacteria with cell surface components. For example, complete Fab fragments, VH regions and FV regions can be expressed in bacteria using phage expression libraries (See for example Ward et al., *Nature* 341:544–546 (1989); Huse et al., *Science* 246: 1275–1281 (1989); and McCafferty et al., *Nature* 348: 552–554 (1990)). Alternatively, a SCID-hu mouse, for example the model developed by Genpharm, can be used to produce antibodies, or fragments thereof.

(b) Pharmaceutical Compositions

The proteins and nucleic acids of the invention may be formulated into pharmaceutical compositions for adminstration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals. Administration of a therapeutically active amount of the pharmaceutical compositions of the present invention is defined as an amount effective, at dosages and for periods of time necessary to achieve the desired result. For example, a therapeutically active amount of a substance may vary according to factors such as the disease state, age, sex, and weight of the individual, and the ability of antibody to elicit a desired response in the individual. Dosage regime may be adjusted to provide the optimum therapeutic response. For example, several divided doses may be administered daily or the dose may be proportionally reduced as indicated by the exigencies of the therapeutic situation.

Accordingly, the present invention provides a pharmaceutical composition for treating cells having a specific protease comprising a recombinant protein or a nucleic acid encoding a recombinant protein of the invention and a pharmaceutically acceptable carrier, diluent or excipient.

The active substance may be administered in a convenient manner such as by injection (subcutaneous, intravenous, intramuscular, etc.), oral administration, inhalation, transdermal administration (such as topical cream or ointment, etc.), or suppository applications. Depending on the route of administration, the active substance may be coated in a material to protect the compound from the action of enzymes, acids and other natural conditions which may inactivate the compound.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985). On this basis, the compositions include, albeit not exclusively, solutions of the substances in association with one or more pharmaceutically acceptable vehicles or diluents, and contained in buffered solutions with a suitable pH and iso-osmotic with the physiological fluids.

The pharmaceutical compositions may be used in methods for treating animals, including mammals, preferably humans, with cancer. It is anticipated that the compositions will be particularly useful for treating patients with B-cell lymphoproliferative disease and melanoma. The dosage and type of recombinant protein to be administered will depend on a variety of factors which may be readily monitored in human subjects. Such factors include the etiology and severity (grade and stage) of the neoplasia.

The following non-limiting examples are illustrative of the present invention:

EXAMPLES

Example 1

Cloning and Expression of Proricin Variants Activated by Disease Specific Proteases Isolation of Total RNA The preproricin gene was cloned from new foliage of the castor bean plant. Total messenger RNA was isolated according to established procedures (Sambrook et al., *Molecular Cloning: A Lab Manual* (Cold Spring Harbour Press, Cold Spring Harbour, (1989)) and cDNA generated using reverse transcriptase.

cDNA Synthesis

Oligonucleotides, corresponding to the extreme 5' and 3' ends of the preproricin gene were synthesized and used to PCR amplify the gene. Using the cDNA sequence for preproricin (Lamb et al., Eur. J. Biochem., 145:266–270, 1985), several oligonucleotide primers were designed to flank the start and stop codons of the preproricin open reading frame. The oligonucleotides were synthesized using an Applied Biosystems Model 392 DNA/RNA Synthesizer. First strand cDNA synthesis was primed using the oligonucleotide Ricin1729C. Three micrograms of total RNA was used as a template for oligo Ricin1729C (5'-ATAACTTGCTGCTCCTTTCA-3') (SEQ ID NO:127) primed synthesis of cDNA using Superscript II Reverse Transcriptase (BRL) following the manufacturer's protocol.

DNA Amplification and Cloning

The first strand cDNA synthesis reaction was used as template for DNA amplification by the polymerase chain reaction (PCR). The preproricin cDNA was amplified using the upstream primer Ricin-99 (5'-CCGGGAGGAAATACTATTGTAAT-3') (SEQ ID NO:128) and the downstream primer Ricin1729C with Vent DNA polymerase (New England Biolabs) using standard procedures (Sambrook et al., Molecular Cloning: A Laboratory Manual, Second Edition, (Cold Spring Harbor Laboratory Press, 1989)). Amplification was carried out in a Biometra thermal cycler (TRIO-Thermalcycler) using the following cycling parameters: denaturation 95° C. for 1 min., annealing 52° C. for 1 min., and extension 72° C. for 2 min., (33 cycles), followed by a final extension cycle at 72° C. for 10 min. The 1846 bp amplified product was fractionated on an agarose gel (Sambrook et al., Molecular Cloning: A Laboratory Manual, Second Edition, (Cold Spring Harbor Laboratory Press, 1989), and the DNA purified from the gel slice using Qiaex resin (Qiagen) following the manufacturer's protocol. The purified PCR fragment encoding the preproricin cDNA was then ligated (Sambrook et al., Molecular Cloning: A Laboratory Manual, Second Edition, (Cold Spring Harbor Laboratory Press, 1989)) into an Eco RV digested pBluescript II SK plasmid (Stratagene), and used to transform competent XL1-Blue cells (Stratagene). Positive clones were confirmed by restriction digestion of purified plasmid DNA. Plasmid DNA was extracted using a Qiaprep Spin Plasmid Miniprep Kit (Qiagen).

DNA Sequencing

The cloned PCR product containing the putative preproricin gene (pAP144) was confirmed by DNA sequencing of the entire cDNA clone. Sequencing was performed using an Applied Biosystems 373A Automated DNA Sequencer, and confirmed by double-stranded dideoxy sequencing by the Sanger method using the Sequenase kit (USB) (see WO 98/49311).

Production and Cloning of Linker Variants pAP144 cut with EcoRI was used as target for PCR pairs employing the Ricin109-Eco oligonucleotide (Ricin-109Eco primer: 5-GGAGGAATCCGGAGATGAAACCGGGAGGAAATACTATTGTAAT-3) (SEQ ID NO:129) and a mutagenic primer for the 5' half of the linker as well as the Ricin1729PstI primer (Ricin 1729-PstI: 5GTAGGCGCTGCAGATAACTTGCTGTCCTTTCAG-3) (SEQ ID NO:130) and a mutagenic primer for the 3' half of the linker. The cycling conditions used for the PCRs were 98 degrees C. for 2 min.; 98° C. 1 min., 52° C. 1 min., 72° C. 1 min. 15 sec. (30 cycles); 72 degrees C. 10 min.; 4 degrees C. soak. The PCR products were then digested by EcoRI and PstI respectively, electrophoresed on an agarose gel, and the bands purified by via glass wool spin columns. Triple ligations comprising the PCR product pairs (corresponding halves of the new linker) and pVL1393 vector digested with EcoRI and PstI were carried out. Recombinant clones were identified by restriction digests of plasmid miniprep DNA and the altered linkers confirmed by DNA sequencing. Note that all altered linker variants were cloned directly into the pVL1393 vector.

Isolation of Recombinant Baculoviruses

Insect cells *S. frugiperda* (Sf9), and *Trichoplusia* ni (Tn368 and BTI-TN-581-4 (High Five)) were maintained on EX-CELL 405 medium JRH Biosciences) supplemented with 10% total calf serum (Summers et al., A Manual of Methods of Baculovirus Vectors and Insect Cell Culture Procedures, (Texas Agricultural Experiment Station, 1987)). Two micrograms of recombinant pVL1393 DNA was co-transfected with 0.5 microgram of BaculoGold AcNPV DNA (Pharmingen) into $2\times10^6$ Tn368 insect cells following the manufacturer's protocol (Gruenwald et al., Baculovirus Expression Vector System: Procedures and Methods Manual, 2nd Edition, (San Diego, Calif., 1993)). On day 5 post-transfection, media were centrifuged and the supernatants tested in limiting dilution assays with Tn368 cells (Summers et al., A Manual of Methods of Baculovirus Vectors and Insect Cell Culture Procedures, (Texas Agricultural Experiment Station, 1987)). Recombinant viruses in the supernatants were then amplified by infecting Tn368 cells at a multiplicity of infection (moi) of 0.1, followed by collection of day 3 to 5 supernatants. A total of three rounds of amplification were performed for each recombinant following established procedures (Summers et al., A Manual of Methods of Baculovirus Vectors and Insect Cell Culture Procedures, (Texas Agricultural Experiment Station, 1987 and Gruenwald et al., Baculovirus Expression Vector System: Procedures and Methods Manual, 2nd Edition, (San Diego, Calif., 1993)).

Expression of Mutant Proricin

Recombinant baculoviruses were used to infect $1\times10^7$ Tn368 or Sf9 cells at an moi of 9 in EX-CELL 405 media (JRH Biosciences) with 25 mM α-lactose in spinner flasks. Media supernatants containing mutant proricins were collected 3 or 4 days post-infection.

Example 2

Harvesting and Affinity Column Purification of Pro-Ricin Variants

Protein samples were harvested three days post infection. The cells were removed by centrifuging the media at 8288 g for ten minutes using a GS3 (Sorvall) centrifuge rotor. The supernatant was further clarified by centrifuging at 25400 g using a SLA-1500 rotor (Sorvall) for 45 minutes. Protease inhibitor phenylmethylsulfonyl fluoride (Sigma) was slowly added to a final concentration of 1 mM. The samples were further prepared by adding α-lactose to a concentration of 20 mM (not including the previous lactose contained in the expression medium). The samples were concentrated to 700 mL using a Prep/Scale-TFF Cartridge (2.5 ft, 10K regenerated cellulose (Millipore)) and a Masterflex pump. The samples were then dialysed for 2 days in 1× Column Buffer (50 mM Tris, 100 mM NaCl, 0.02% NaN3, pH 7.5) using dialysis tubing (10 K MWCO, 32 mm flat width(Spectra/Por)). Subsequently, the samples were clarified by centrifuging at 25400 g using a SLA-1500 rotor (Sorvall) for 45 minutes.

Following centrifugation, the samples were degassed and applied at 4 degrees C. to a XK26/20 (Pharmacia) column (attached to a Pharmacia peristaltic pump, Pharmacia Single-path Monitor UV-1 Control and Optical Units, and Bromma LKB 2210 2-Channel Recorder) containing 20 mL α-Lactose Agarose Resin (Sigma). The column was washed for 3 hours with 1× Column buffer. Elution of proricin variant was performed by eluting with buffer (1× Column buffer (0.1% NaN3), 100 mM Lactose) until the baseline was again restored. The samples were concentrated using an Amicon 8050 concentrator (Amicon) with a YM10 76 mm membrane, utilizing argon gas to pressurize the chamber. The samples were further concentrated in Centricon 10 (Millipore) concentrators according to manufacturer's specifications.

Purification of Variant PAP-Protein by Gel Filtration Chromatography

In order to purify variant from processed material produced during fermentation, the protein was applied to a SUPERDEX 75 (16/60) column and SUPERDEX 200 (16/60) column (Pharmacia) connected in series equilibrated with 100 mM Tris, 200 mM NaCl, pH 7.5 containing 100 mM lactose and 1.0% β-mercaptoethanol (βME). The flow rate of the column was 0.15 mL/min and fractions were collected every 25 minutes. The UV (280 nm) trace was used to determine the approximate location of the purified PAP-protein and thus determine the samples for Western analysis.

Western Analysis of Column Fractions

Fractions eluted from the SUPERDEX columns (Pharmacia) were analyzed for purity using standard Western blotting techniques. An aliquot of 10 μL from each fraction was boiled in 1× sample buffer (62.6 mM Tris-Cl, pH 6.8, 4.4% βME, 2% sodium dodecyl sulfate (SDS), 5% glycerol (all from Sigma) and 0.002% bromophenol blue (Biorad)) for five minutes. Denatured samples were loaded on 12% Tris-Glycine Gels (Biorad) along with 50 ng of $RCA_{60}$ (Sigma) and 5 μL of kaleidoscope prestained standards (Biorad). Electrophoresis was carried out for ninety minutes at 100V in 25 mM Tris-Cl, pH 8.3, 0.1% SDS, and 192 mM glycine using the BioRad Mini Protean II cells (Biorad).

Following electrophoresis gels were equilibrated in transfer buffer (48 mM Tris, 39 mM glycine, 0.0375% SDS, and 20% Methanol) for a few minutes. PVDF Biorad membrane was presoaked for one minute in 100% methanol, rinsed in $ddH_2O$ and two minutes in transfer buffer. Whatman paper was soaked briefly in transfer buffer. Five pieces of Whatman paper, membrane, gel, and another five pieces of Whatman paper were arranged on the bottom cathode (anode) of the Pharmacia Novablot transfer apparatus (Pharmacia). Transfer was for one hour at constant current (2 $mA/cm^2$).

Transfer was confirmed by checking for the appearance of the prestained standards on the membrane. Non-specific sites on the membrane were blocked by incubating the blot for thirty minutes in 1× Phosphate Buffered Saline (1× PBS; 137 mM NaCl, 2.7 mM KCl, 8 mM $Na_2HPO_4$,1.5 mM $KH_2PO_4$, pH 7.4) with 5% skim milk powder Carnation). Primary antibody rabbit anti-ricin, (Sigma) was diluted 1:3000 in 1× PBS containing 0.1% Tween 20 (Sigma) and 2.5% skim milk and incubated with blot for forty five minutes on a orbital shaker (VWR). Non-specifically bound primary antibody was removed by washing the blot for ten minutes with 1× PBS containing 0.2% Tween 20. This was repeated four times. Secondary antibody donkey anti-rabbit (Amersham) was incubated with the blot under the same conditions as the primary antibody. Excess secondary antibody was washed as described above. Blots were developed with the ECL Western Blotting detection reagents according to the manufacturer's instructions. Blots were exposed to Medtec's Full Speed Blue Film (Medtec) or Amersham's ECL Hyperfilm (Amersham) for one second to five minutes. Film was developed in a KODAK Automatic Developer.

Determination of Lectin Binding Ability of Pro-Ricin Variant

An Immulon 2 plate (VWR) was coated with 100 μl per well of 10 μg/ml of asialofetuin and left overnight at 4° C. The plate was washed with 3×300 μL per well with $ddH_2O$ using an automated plate washer (BioRad). The plate was blocked for one hour at 37° C. by adding 300 μL per well of PBS containing 1% ovalbumin. The plate was washed again as above. Proricin variant PAP-protein was added to the plate in various dilutions in 1× Column Buffer, (50 mM Tris, 100 mM NaCl, pH 7.5). A standard curve of $RCA_{60}$ (Sigma) from 1–10 ng was also included. The plate was incubated for 1 h at 37° C. The plate was washed as above. Anti-ricin monoclonal antibody (Sigma) was diluted 1:3000 in 1× PBS containing 0.5% ovalburnin and 0.1% Tween-20, added at 100 μL per well and incubated for 1 h at 37° C. The plate was washed as above. Donkey anti-rabbit polyclonal antibody was diluted 1:3000 in 1× PBS containing 0.5% ovalburnin, 0.1% Tween-20, and added at 100 μL per well and incubated for 1 h at 37° C. The plate was given a final wash as described above. Substrate was added to plate at 100 μL per well (1 mg/mL o-phenylenediamine (in $H_2O$), 1 μL/mL $H_2O_2$) and after development 25 μL of stop solution (20% $H_2SO_4$) was added and the absorbance read (A490 nm–A630 nm) using a SPECTRA MAX 340 plate reader (Molecular Devices).

Determination of PAP-Protein Activity Using the Rabbit Reticulocyte Assay

Ricin samples were prepared for reduction.

A) $RCA_{60}$=3,500 ng/μL of $RCA_{60}$+997 μL 1× Endo buffer (25 mM Tris, 25 mM KC1, 5 mM $MGC1_2$, pH 7.6)

Reduction=95 μL of 10 ng/μL+5 μL β-mercaptoethanol

B) Ricin variants

Reduction=40 μL variant+2 μL β-mercaptoethanol

The ricin standard and the variants were incubated for 30 minutes at room temperature.

Ricin—Rabbit Reticulocyte Lysate Reaction

The required number of 0.5 mL tubes were labelled. (2 25 tubes for each sample, + and − aniline). To each of the sample tubes 20 μL of 1× endo buffer was added, and 30 μL of buffer was added to the controls. To the sample tubes either 10 μL of 10 ng/μL, Ricin or 10 μL of variant was added. Finally, 30 μL of rabbit reticulocyte lysate was added to all the tubes. The samples were incubated for 30 minutes at 30° C. using the thermal block. Samples were removed from the 0.5 mL tube and contents added into a 1.5 mL tube containing 1 mL of TRIZOL (Gibco). Samples were incubated for 15 minutes at room temperature. After the incubation, 200 μL of chloroform was added, and the sample was vortexed and spun at 12,000 g for 15 minutes at 4° C. The top aqueous layer from the samples was removed and contents added to a 1 mL tube containing 500 μL of isopropanol. Samples were incubated for 15 minutes at room temperature and then centrifuged at 12,000 for 15 minutes at 4° C. Supernatant was removed and the pellets were washed with 1 mL of 70% ethanol. Centrifugation at 12,000 g for 5 minutes at 4° C. pelleted the RNA. All but approximately 20 μL of the supernatant was removed and the RNA pellet was allowd to air dry. Pellets from the other samples (+aniline samples) were dissolved in 20 μL of DEPC treated $ddH_2O$. An 80 μL aliquot of 1 M aniline (distilled) with 2.8 M acetic acid was added to these RNA samples and transferred to a fresh 0.5 mL tube. The samples were incubated in the dark for 3 minutes at 60° C. RNA was precipitated by adding 100 μl, of 95% ethanol and 5 μL of 3M sodium acetate, pH 5.2 to each tube and centrifuging at 12,000 g for 30 minutes at 4° C. Pellets were washed with 1 mL 70% ethanol and centrifuged again at 12,000 g for 5 minutes at 4° C. to precipitate RNA. The supernatant was removed and air dried. These pellets were dissolved in 10 μL of 0.1× E buffer. To all samples, 10 μL of formamide loading dye was added. The RNA ladder (BRL) (8 μL of ladder+8 μL of loading dye) was also included. Samples were incubated for 2 minutes at 70° C. on the thermal block. Electrophoresis was carried out on the samples using 1.2% agarose, 50% formamide gels in 0.1× E buffer+0.2% SDS. The gel was run for 90 minutes at 75 volts. RNA was visualized by staining the gel in 1 μg/μL ethidium bromide in running buffer for 45 minutes. The gel was examined on a 302 nm UV box, photographed using the gel documentation system and saved to a computer disk.

Results:

Protein Expression Yields

Aliquots were taken at each stop of the harvesting/purification and tested. Yields of functional ricin variant were determined by ELISA. Typical results of an 3400 mL prep of infected *T. ni* cells are given below.

| Aliquot | μg PAP 304 |
|---|---|
| Before concentration and dialysis | 14,472 |
| after concentration and dialysis | 13,611 |
| alpha-Lactose agarose column flow through | 418 |
| alpha-Lactose agarose column elution | 8,682 |

Yield: 8,682/14,472 = 60%

Purification of PAP-Protein and Western Analysis of Column Fractions

Partially purified PAP-protein was applied to Superdex 75 and 200 (16/60) columns connected in series in order to remove the contaminating non-specifically processed PAP-protein. Eluted fractions were tested via Western analysis as described above and the fractions containing the most pure protein were pooled, concentrated and dialyzed against 1× PBS buffer and then sterilized by filtration (Millipore). Final purified PAP-protein has less than 1% processed variant.

The purified PAP-protein was tested for susceptibility to cleavage by the particular protease and for activation of the A chain of the proricin variant, (inhibition of protein synthesis). Typically, PAP-protein was incubated with and without protease for a specified time period and then electrophoresed and blotted. Cleaved PAP-protein will run as two 30 kDa proteins (B is slightly larger) under reducing (SDS-PAGE) conditions. Unprocessed PAP-protein, which contains the linker region, will migrate at 60 kDa.

Activation of PAP-Protein Variant with Specific Protease

Activation of protease treated PAP-protein is based on the method of *May* et al. (EMBO Journal. 8 301–8, 1989). Activation of ricin A chain upon cleavage of the intermediary linker results in catalytic depurination of the adenosine 4325 residue of 28S or 26S rRNA. This depurination renders the molecule susceptible to amine-catalyzed hydrolysis by aniline of the phosphodiester bond on either side of the modification site. The result is a diagnostic 390 base band. As such, reticulocyte ribosomes incubated with biochemically purified ricin A chain, released the characteristic RNA fragment upon aniline treatment of isolated rRNA (May, M. J. et al. Embo. Journal, 8:301–308 at 302–303 (1989)). It is on this basis that the assay allows for the determination of activity of a ricin A chain which has been cleaved from the intact unit containing a particular variant linker sequence.

Example 3

In Vitro Protease Digestion of Proricin Variants:

Affinity-purified proricin variant is treated with individual disease-specific proteases to confirm specific cleavage in the linker region. Ricin-like toxin variants are eluted from the lactose-agarose matrix in protease digestion buffer (50 mM NaCl, 50 mM Na-acetate, pH 5.5, 1 mM dithiothreitol) containing 100 mM lactose. Proricin substrate is then incubated at 37° C. for 60 minutes with a disease-specific protease. The cleavage products consisting ricin A and B chains are identified using SDS/PAGE (Sambrook et al., Molecular Cloning: a Laboratory Manual, 2nd. ed., Cold Spring Harbor Press, 1989), followed by Western blot analysis using anti-ricin antibodies (Sigma). FIG. 19 shows the cleavage products of an MMP-9 digestion of PAP323, PAP324 and PAP325.

Matrix metalloproteinases may be prepared substantially as described by Lark, M. W. et al. (*Proceedings of the 4th International Conference of the Inflammation Research Association* Abstract 145 (1988)) and Welch, A. R. et al. (Arch. Biochem. Biophys. 324:59–b 64 (1995)).

Urokinase plasminogen activator may be prepared substantially as described by Holmberg, L. et al. (Biochim Biophys Acta, 445:215–222, (1976)) and Someno, T. et al. (J. Biochem 97:1493–1500 (1985)).

Example 4

Cytotoxicity of Ricin and Ricin Variants on Cell Lines

Cell Lines

COS-I (African Green Monkey Kidney Cells)

This is an SV40 transformed cell line which was prepared from established simian cells CV-1. (Reference: Gluzman, Y. (1975) Cell, 23, 175–182)(ATCC CRL 1650).

HT-1080 Human Fibrosarcoma (ATCC CCL 121) This cell line was shown to produce active MMP-9 in tissue culture. (References: Moore et al. (1997) Gynecologic Oncology 65, 83–88.)

Cell Preparation

After washing with 1× PBS (0.137 M NaCl, 2.68 mM KCl, 8.10 mM $Na_2HPO_4$, 1.47 mM $KH_2PO_4$), cells in log phase growth were removed from plates with 1× trypsin/EDTA (Gibco/BRL). The cells were centrifuged at 1100 rpm for 3 min, resuspended in Dulbecco's Modified Eagle Medium containing 10% FBS and 1× pen/strep, and then counted using a haemocytometer. They were adjusted to a concentration of $5\times10^4$ cells·ml$^{-1}$. One hundred microliters per well of cells was added to wells 2B–2G through to wells 9B–9G of a Falcon 96 well tissue culture plate. A separate 96 well tissue culture plate was used for each sample of Ricin or Ricin variant. The plates were incubated at 37° C. with 5% $CO_2$ for 24 hours.

Toxin Preparation

The Ricin and Ricin variants were sterile filtered using a 0.22 μm filter (Millipore). The concentration of the sterile samples were then quantified by $A_{280}$ and confirmed by BCA measurements (Pierce). For the variants digested with the MMP-9 protease in vitro, the digests were carried out as described in the digestion procedure for each protease. The digests were then diluted in the 1000 ng·ml$^{-1}$ dilution and sterile filtered. Ricin and Ricin variants were serially diluted to the following concentrations: 1000 ng·ml$^{-1}$, 100 ng·ml$^{-1}$, 10 ng·ml$^{-1}$, 1 ng·ml$^{-1}$, 0.1 ng·ml$^{-1}$, 0.01 ng·ml$^{-1}$, 0.001 ng·ml$^{-1}$ with media containing 10% FBS and 1× pen/strep.

Application of Toxin or Variants to Plates

Columns 2 to 9 were labeled: control, 1000 ng·ml$^{-1}$, 100 ng·ml$^{-1}$, 10 ng·ml$^{-1}$, 1 ng·ml$^{-1}$, 0.1 ng·ml$^{-1}$, 0.01 ng·ml$^{-1}$, 0.001 ng·ml$^{-1}$ consecutively. The media was removed from all the sample wells with a multichannel pipettor. For each plate of variant and toxin, 50 μl of media was added to wells 2B to 2G as the control, and 50 μl of each sample dilution was added to the corresponding columns. The plates were incubated for one hour at 37° C. with 5% $CO_2$, then washed once and replaced with media, then incubated for 48 hours at 37° C. with 5% $CO_2$.

Sample Application

The whole amount of media (and/or toxin) was removed from each well with a multichannel pipettor, and replaced with 100 μl of the substrate mixture (Promega Cell Titer 96 Aqueous Non-Radioactive Cell Proliferation Assay Kit). The plates were incubated at 37° C. with 5% $CO_2$ for 2 to 4 hours, and subsequently read with a Spectramax 340 96 well plate reader at 490 nm. The $IC_{50}$ values were calculated using the GRAFIT software program.

Results

The results of the cytotoxicity assay are shown in Tables 1 to 4. In almost all cases the novel variants show preferential activation in the tumour cell line HT-1080 (human fibrosarcoma) as compared with the non-tumourogenic cell line COS-1 (immortalized cell line form the kidney of an African green monkey).

Example 5

Maximum Tolerable Dose Data

The protocol for the maximum tolerable dose (MTD) study involved three intravenous injections of variant, on days 1, 5 and 9, into the tail vein of either a Nude/SCID mouse. Three animals were used for each dose tested. The samples were diluted into saline solution containing 100 μg/mL Bovine Serum Albumin on the same day as the injection. Animals were observed for 14 days after dosing. Any surviving animals were euthanized after 14 days of study. The MTD value was defined as the highest dose of sample tested where all animals in the group survived. The results are presented in Table 5.

These results demonstrate that linkers of the invention in proricin variants decrease the toxicity of the recombinant proteins.

Example 6

In Vivo Studies (a) Protocol for A431 Animal Model Studies

Tumour growth was monitored daily by measuring tumour dimensions with calipers. The treatment initiation date was dependent on the rate of tumour growth. Four groups (4 mice per group) of mice develop tumours of the desired size (50 mm$^3$–100 mm$^3$). Such mice are weighed and treatment initiated. This treatment initiation date is considered as day 1, and the mice were given a bolus intravenous injection of variant on this day. Injections were administered through the lateral tail vein. The treatment groups are shown in Table 6.

All samples and buffer were made up in saline solution containing 100 μg/mL Bovine Serum Albumin.

(b) In Vivo Efficacy Studies

Figure 20:
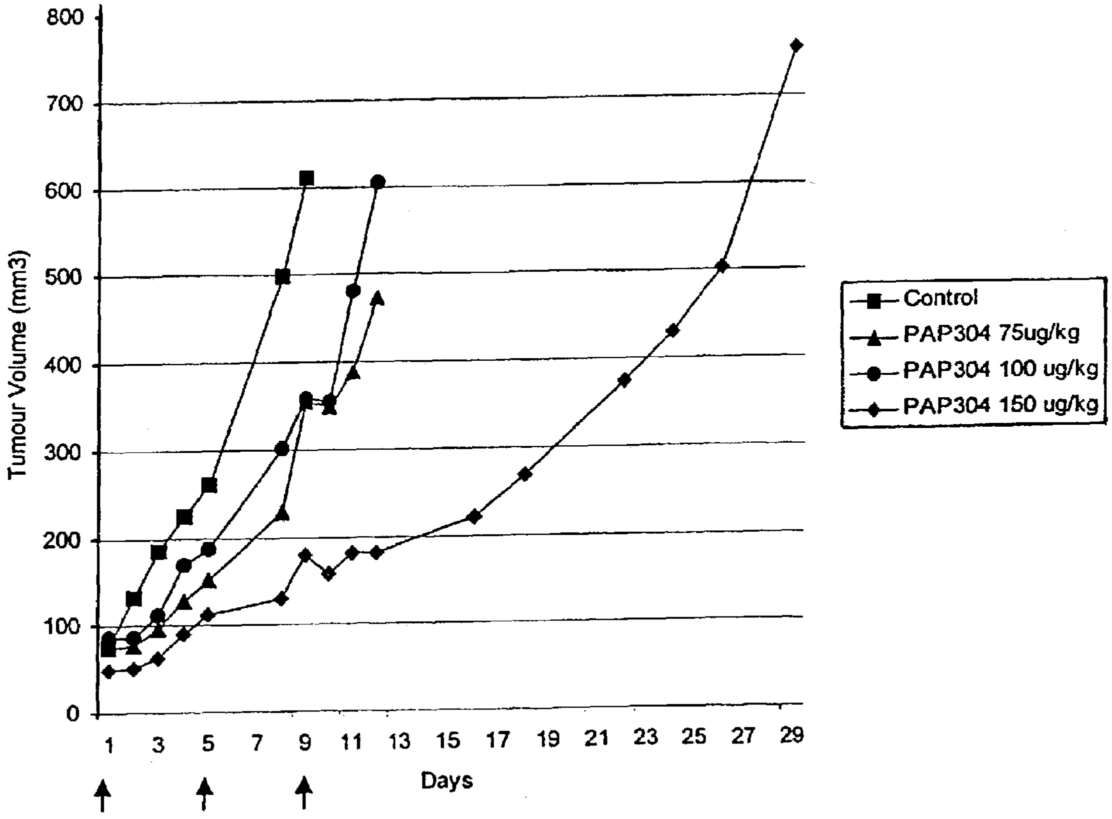
FIG. 20 is a graph showing the treatment of human tumour A431 with PAP304.
Figure 21:
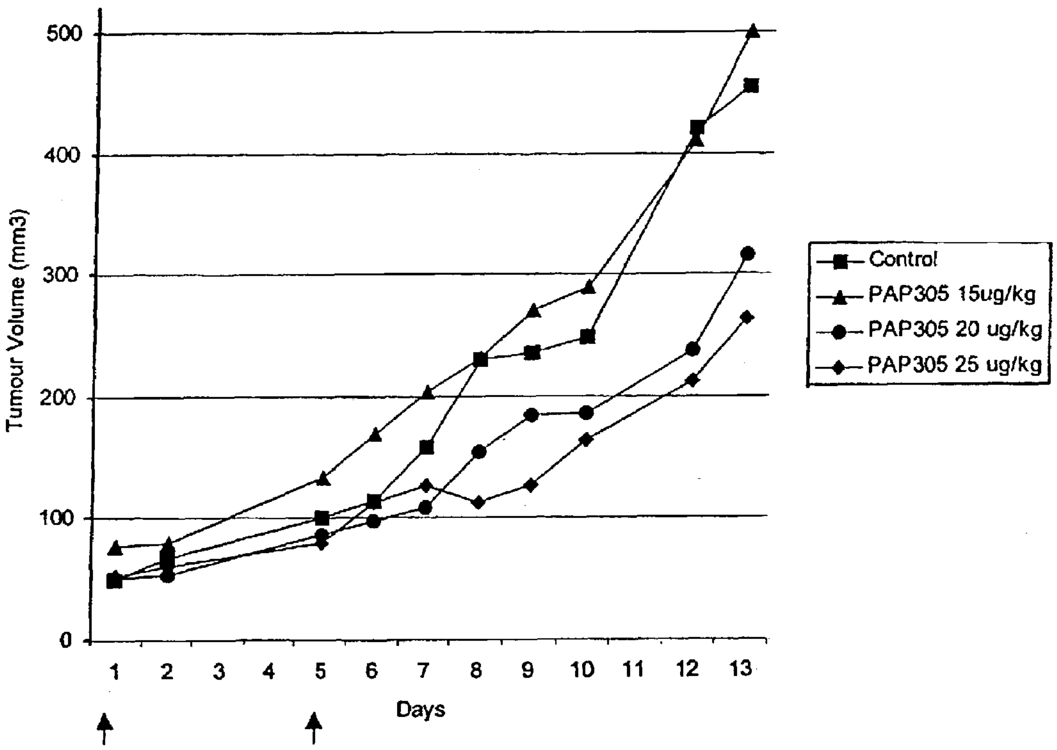
FIG. 21 is a graph showing the treatment of human tumour A431 with PAP305.

Subcutaneous A431 tumours were established in SCID mice. The tumours were treated with either PAP304 or PAP305 when the tumours reached 50 mm$^3$ on Days 1, 5 and 9. The results shown in FIGS. 20 and 21 demonstrate that the linker decreases the toxicity of the variant (as compared with ricin) and the variants PAP304 and PAP305 are activated at or near the A431 (human epithelial carcinoma) solid tumour in mice. A very exciting result is shown in FIG. 20. In this study, the variant PAP304 was able to slow down the growth of A431 solid tumour (17 day delay), without any signs of dose limiting toxicity (e.g., no weight loss or death).

Figure 22:
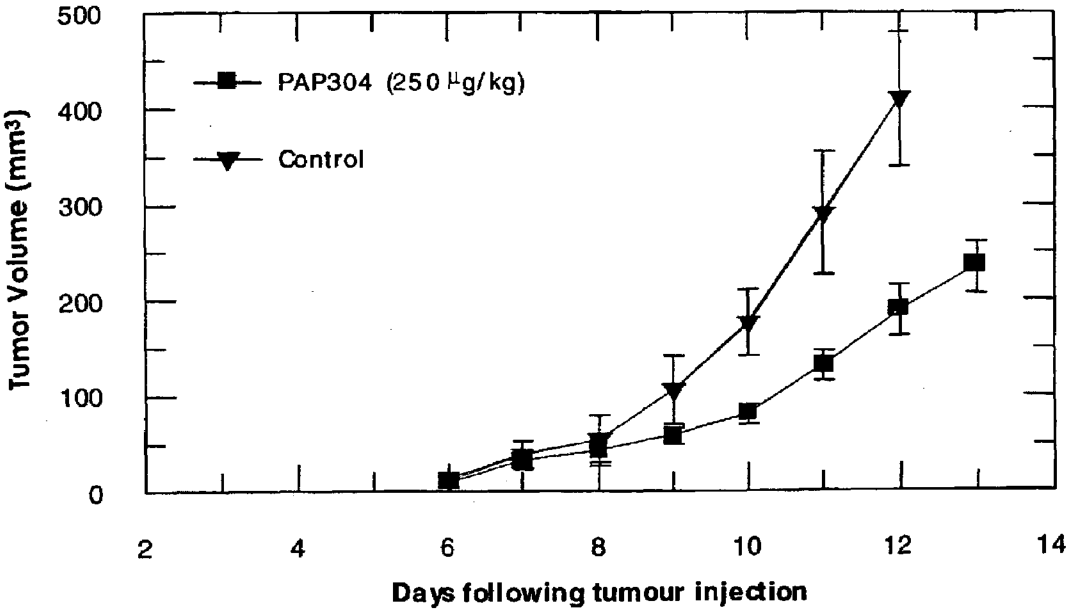
FIG. 22 is a graph showing a significant delay in tumor growht in the murine tumor model.

(c) Protocol and Efficacy for Testing PAP304 against P388 Murine Leukemia Tumour Model Mice were grouped according to body weight. Animals (n=4) were inoculated (Day=0) with 1×106 cells implanted subcutaneously in the flank of the BDF-1 mouse in a volume of 50 μL with a 28 g needle. P388 murine leukemia cells from the ATCC tumor repository were maintained as an ascitic fluid in the BDF-1 mouse which were passaged to new mice weekly. The cells used for experiment were used within passage 3–20. For the experiment, cells were rinsed with Hanks Balanced Salt Solution, counted on a heamocytometer and diluted with HBSS to a concentration of 20×106 cells/ml. PAP304 was injected intravenously on days 3, 6 and 9 after tumour injection. The results are shown in FIG. 22. A significant delay in tumor growht in the murine tumor model.

Having illustrated and described the principles of the invention in a preferred embodiment, it should be appreciated to those skilled in the art that the invention can be modified in arrangement and detail without departure from such principles. We claim all modifications coming within the scope of the following claims.

All publications, patents and patent applications referred to herein are incorporated by reference in their entirety to the same extent as if each individual publication, patent or patent application was specifically and individually indicated to be incorporated by reference in its entirety.

FULL CITATIONS FOR CERTAIN REFERENCES REFERRED TO IN THE SPECIFICATION

Bever Jr., C. T., Panitch, H. S., and Johnson, K. P. (1994) Neurology 44(4), 745–8. increased cathepsin B activity in peripheral blood mononuclear 5 cells of multiple sclerosis patients.

Cohen, P., Graves, H. C., Peehl, D. M., Kamarei, M., Giudice, L. C., and Rosenfeld, R. G. (1992) journal of Clinal Endocrinology and Metabolism 75(4), 1046–53. Prostate-specific antigen (PSA) is an insulin-like growth factor binding protein-3 protease found in seminal plasma.

Conover, C. A. and De Leon, D. D. (1994) J. Biol. Chem. 269(10), 7076–80. Acid activated insulin-like growth factor-binding protein-3 proteolysis in normal and transformed cells. Role of cathepsin D.

Cuzner, M. L., Opdenakker, G. Plasminogen activators and matrix metalloproteases, mediators of extracellular proteolysis in inflammatory demyelination of the central nervous system. J. Neuroimmunol 94(1–2):1–14 (1999).

Desreumaux, P., Huet, G., Zerimech, F., Gambiez, L., Balduyck, M., Baron, P., Degand, P., Cortot, A., Colombel, J. F., Janin, A. Acute inflammatory intestinal vascular lesions and in situ abnormalities of the plasminogen activation system in Crohn's disease. Eur. J. Gastroenterol Hepatol, 11(10): 1113–9 (1999).

Hansen, G., Schuster, A., Zubrod, C., and Wahn, V. (1995) Resp 62(3), 117–24. Alpha 1-proteinase inhibitor abrogates proteolytic and secretagogue activity of cystic fibrosis sputum.

Muller, H. L., Oh, Y., Gargosky, S. E., Lehrnbecher, T., Hintz, R. L., and Rosenfeld, R. G. (1993) journal of Clinical Endocrinology and Metabolism 77(5), 1113–9. Concentrations of insulin-like growth factor (IGF)-binding protein-3 (IGFBP-3), IGF, and IGFBP-3 protease activity in cerebrospinal fluid of children with leukemia, central nervous system tumor, or meningitis.

Pap, G., Eberhardt, R., Rocken, C., Nebelung, W., Neumann, H. W., Roessner, A. Expression of stromelysin and urokinase type plasminogen activator protein in resection specimens and biopsies at different stages of osteoarthritis of the knee. Pathol Res Pract 196(4):219–26 (2000).

Slot, O., Brunner, N., Locht, H., Oxholm, P., Stephens, R. W., Soluble urokinase plasminogen activator receptor in plasma of patients with inflammatory rheumatic disorders: increased concentrations in rheumatoid arthritis. Ann Rheum Dis, 58(8):488–92 (1999).

1) Cytotoxicity of Selected Variants

TABLE 1

| Selected Variants against COS-1 Cells - Target Protease MMP-9 | | | | | | | | |
|---|---|---|---|---|---|---|---|---|
| | Ricin | PAP220 | PAP301 | PAP302 | PAP303 | PAP304 | PAP305 | PAP308 |
| Linker Length (residues) | — | 23 | 23 | 16 | 15 | 8 | 12 | 12 |
| Reduction in toxicity relative to Ricin | 1X | 23X | 24X | 118X | 63X | 1220X | 145X | 89X |

TABLE 2

| Selected Variants against HT1080 Cells - Target Protease MMP-9 | | | | | | | | |
|---|---|---|---|---|---|---|---|---|
| | Ricin | PAP220 | PAP301 | PAP302 | PAP303 | PAP304 | PAP305 | PAP308 |
| Linker Length (residues) | — | 23 | 23 | 16 | 15 | 8 | 12 | 12 |

TABLE 2-continued

| Selected Variants against HT1080 Cells - Target Protease MMP-9 | | | | | | | | |
|---|---|---|---|---|---|---|---|---|
| | Ricin | PAP220 | PAP301 | PAP302 | PAP303 | PAP304 | PAP305 | PAP308 |
| Reduction in toxicity relative to Ricin | 1X | 4X | 5X | 24X | 12X | 137X | 38X | 21X |

2) Cytotoxicity Data from Selected Variants

TABLE 3

Selected Variants against COS-1 cells

| MMP9 Variants | | | | | | |
|---|---|---|---|---|---|---|
| | Ricin | PAP316 | PAP318 | PAP323 | PAP324 | PAP325 |
| Linker Length (residues) | — | 23 | 23 | 21 | 19 | 17 |
| Reduction in toxicity relative to Ricin | 1X | 39X | 100X | 65X | 67X | 82X |

| UPA Variants | | | | | | |
|---|---|---|---|---|---|---|
| | Ricin | PAP313 | PAP314 | PAP315 | PAP320 | PAP321 | PAP322 |
| Linker Length (residues) | — | 7 | 15 | 14 | 13 | 11 | 9 |
| Reduction in toxicity relative to Ricin | 1X | 110X | 52X | 75X | 55X | 1283X | 82X |

TABLE 4

Selected Variants against HT1080 Cells

| MMP9 Variants | | | | | | |
|---|---|---|---|---|---|---|
| | Ricin | PAP316 | PAP318 | PAP323 | PAP324 | PAP325 |
| Linker Length (residues) | — | 23 | 23 | 21 | 19 | 17 |
| Reduction in toxicity relative to Ricin | 1X | 13X | 51X | 15X | 14X | 20X |

| UPA Variants | | | | | | | |
|---|---|---|---|---|---|---|---|
| | Ricin | PAP313 | PAP314 | PAP315 | PAP320 | PAP321 | PAP322 |
| Linker Length (residues) | — | 7 | 15 | 14 | 13 | 11 | 9 |
| Reduction in toxicity relative to Ricin | 1X | 43X | 27X | 18X | 14X | 367X | 51X |

TABLE 5

Maximum Tolerable Dose of MMP9 Variants

| MMP9 Variant | Linker Size | In Vivo (μg/kg) |
|---|---|---|
| PAP301 | 23 | 8 |
| PAP302 | 16 | 40 |
| PAP303 | 15 | 10 |
| PAP304 | 8 | 150 |
| PAP305 | 12 | 20 |
| PAP308 | 12 | 30 |
| PAP309 | 23 | 20 |
| PAP316 | 23 | 20 |
| PAP318 | 23 | <20 |
| PAP323 | 21 | 15 |
| PAP324 | 19 | 20 |
| PAP325 | 17 | 20 |

(cf. Ricin-1.6 μg/kg and PAP220-13 μg/kg)

TABLE 6

| Group | Sample | Drug Dose (μg/kg) | Treatment (days) |
|---|---|---|---|
| 1 | Control-Buffer | 0 | 1, 5, and 9 |
| 2 | PAP304 | 75 | 1, 5, and 9 |
| 3 | PAP304 | 100 | 1, 5, and 9 |
| 4 | PAP304 | 150 | 1, 5, and 9 |

We claim:

1. A recombinant protein comprising an A chain of a ricin-like toxin, a B chain of a ricin-like toxin and a heterologous linker amino acid sequence, linking the A and B chains, wherein the linker sequence contains a cleavage recognition site for a specific protease and is selected from the group consisting of the amino acid sequence of PAP302 as shown in FIG. 2C (SEQ ID NO:14); the amino acid sequence of PAP303 as shown in FIG. 3C (SEQ ID NO:21): the amino acid sequence of PAP304 as shown in FIG. 4C (SEQ ID NO:28); the amino acid sequence of PAP305 as shown in FIG. 5C (SEQ ID NO:35); the amino acid sequence of PAP308 as shown in FIG. 6C (SEQ ID NO:42): the amino acid sequence of PAP313 as shown in FIG. 8C (SEQ ID NO:56); the amino acid sequence of PAP316 as shown in FIG. 11C (SEQ ID NO:77); the amino acid sequence of PAP323 as shown in FIG. 16C (SEQ ID NO:112); the amino acid sequence of PAP324 as shown in FIG. 17C (SEQ ID NO:119); and the amino acid sequence of PAP325 as shown in FIG. 18C (SEQ ID NO:126).

2. A protein according to claim 1 wherein the protease is associated with a cancer cell.

3. A protein according to claim 2 wherein the cancer cell is one found in T- and B cell lymphoproliferative diseases, ovarian cancer, pancreatic cancer, head and neck cancer, squamous cell carcinoma, gastrointestinal cancer, breast cancer, prostate, cancer or non small cell lung cancer.

4. A protein according to claim 1 wherein the protease is associated with an inflammatory cell.

5. A protein according to claim 4 wherein the cell is one found in rheumatoid arthritis, atherosclerotic cells, Crohn's disease, or central nervous system disease.

6. A recombinant protein of claim 1 wherein the A chain is ricin A chain, abrin toxin A chain, diphtheria toxin A chain, Domain III of *Pseudomonas* exotoxin, volkensin toxin A chain, cholera toxin A chain, modeccin toxin A chain, viscumin toxin A chain, or shiga toxin A chain.

7. A recombinant protein of claim 1 wherein the B chain is ricin B chain, abrin toxin B chain, diphtheria toxin B chain, Domain I/II of *Pseudomonas* exotoxin, volkensin toxin B chain, cholera toxin B chain, modeccin toxin B chain, viscumin toxin B chain, or shiga toxin B chain.

8. A pharmaceutical composition comprising a recombinant protein of claim 1 and a pharmaceutically acceptable carrier, diluent or excipient.

9. A linker protein having an amino acid sequence selected from the group consisting of: the amino acid sequence of PAP302 as shown in FIG. 2C (SEQ ID NO:14); the amino acid sequence of PAP303 as shown in FIG. 3C (SEQ ID NO:21); the amino acid sequence of PAP304 as shown in FIG. 4C (SEQ ID NO:28); the amino acid sequence of PAP305 as shown in FIG. 5C (SEQ ID NO:35); the amino acid sequence of PAP308 as shown in FIG. 6C (SEQ ID NO:42); the amino acid sequence of PAP313 as shown in FIG. 8C (SEQ ID NO:56); the amino acid sequence of PAP316 as shown in FIG. 11C (SEQ ID NO:77); the amino acid sequence of PAP323 as shown in FIG. 16C (SEQ ID NO: 112); the amino acid sequence of PAP324 as shown in FIG. 17C (SEQ ID NO:119); and the amino acid sequence of PAP325 as shown in FIG. 18C (SEQ ID NO:126).

10. A recombinant protein of claim 1 wherein the linker sequence has the amino acid sequence of PAP304 as shown in FIG. 4C (SEQ ID NO:28).

11. A recombinant protein of claim 1 wherein the linker sequence has the amino acid sequence of PAP313 as shown in FIG. 8C (SEQ ID NO:56).

* * * * *